United States Patent
Wagner et al.

(10) Patent No.: US 12,214,136 B2
(45) Date of Patent: Feb. 4, 2025

(54) ADJUSTABLE HEADGEAR TUBING FOR A PATIENT INTERFACE

(71) Applicant: RESMED PTY LTD, Bella Vista (AU)

(72) Inventors: Stewart Joseph Wagner, Hawkesbury (AU); Aaron Samuel Davidson, Sydney (AU); Gerard Michael Rummery, Woodford (AU); Adam Francis Barlow, Sydney (AU); Hugh Francis Stewart Thomas, Sydney (AU); Justin John Formica, Sydney (AU); Mira Aswani, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 74 days.

(21) Appl. No.: 18/166,017

(22) Filed: Feb. 8, 2023

(65) Prior Publication Data

US 2023/0241342 A1 Aug. 3, 2023

Related U.S. Application Data

(63) Continuation of application No. 17/780,804, filed as application No. PCT/AU2020/051286 on Nov. 27, 2020, now Pat. No. 11,666,724.

(30) Foreign Application Priority Data

Nov. 29, 2019 (AU) .............................. 2019904513
Feb. 21, 2020 (AU) .............................. 2020900503

(51) Int. Cl.
*A61M 16/06* (2006.01)
*A61M 16/08* (2006.01)

(52) U.S. Cl.
CPC .... *A61M 16/0683* (2013.01); *A61M 16/0622* (2014.02); *A61M 16/0672* (2014.02); *A61M 16/0875* (2013.01)

(58) Field of Classification Search
CPC .......... A61M 16/0622; A61M 16/0672; A61M 16/0683; A61M 16/0875; A61M 2016/0661
See application file for complete search history.

(56) References Cited

U.S. PATENT DOCUMENTS

| 4,231,359 A | 11/1980 | Martin |
| 4,782,832 A | 11/1988 | Trimble et al. |

(Continued)

FOREIGN PATENT DOCUMENTS

| JP | 2019-502492 A | 1/2019 |
| WO | WO 98/004310 A1 | 2/1998 |

(Continued)

OTHER PUBLICATIONS

"*Respiratory Physiology*", by John B. West, Lippincott Williams & Wilkins, 9th edition published 2012 (8 pages).

(Continued)

*Primary Examiner* — Valerie L Woodward
(74) *Attorney, Agent, or Firm* — Nixon & Vanderhye P.C.

(57) ABSTRACT

Aspects of the present technology comprise a positioning and stabilising structure to hold a seal-forming structure in a therapeutically effective position on a head of a patient. The seal-forming structure may be constructed and arranged to form a seal with a region of the patient's face surrounding an entrance to the patient's airways for sealed delivery of a flow of air at a therapeutic pressure of at least 4 cmH$_2$O with respect to ambient air pressure throughout the patient's respiratory cycle in use. The positioning and stabilising structure may comprise a front hoop arranged to contact, in use, at least a region of the patient's head superior to an otobasion superior of the patient's head and a rear strap. The positioning and stabilising structure may comprise an adjustment mechanism for adjustment of the front hoop and the rear strap relative to the patient's head, the adjustment (Continued)

mechanism being arranged in a single operation to adjust both the front hoop and rear strap to enable the positioning and stabilising structure to fit different size heads.

25 Claims, 62 Drawing Sheets

(56) References Cited

U.S. PATENT DOCUMENTS

| | | | |
|---|---|---|---|
| 4,944,310 A | 7/1990 | Sullivan | |
| 5,687,715 A | 11/1997 | Landis | |
| 6,422,238 B1 | 7/2002 | Lithgow | |
| 6,532,959 B1 | 3/2003 | Berthon-Jones | |
| 6,581,594 B1 | 6/2003 | Drew et al. | |
| 7,134,432 B2 * | 11/2006 | Olsen | A61M 16/049 128/200.26 |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 10,029,062 B2 | 7/2018 | Kwok | |
| 2004/0226566 A1 * | 11/2004 | Gunaratnam | A61M 16/0825 128/207.18 |
| 2005/0150499 A1 | 7/2005 | Bordewick | |
| 2006/0090760 A1 | 5/2006 | Gradon | |
| 2006/0118117 A1 * | 6/2006 | Berthon-Jones | A61M 16/0003 128/206.27 |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2010/0024811 A1 * | 2/2010 | Henry | A61M 16/0622 128/202.16 |
| 2015/0151070 A1 | 6/2015 | Capra et al. | |
| 2017/0319808 A1 | 11/2017 | Answine | |
| 2018/0207385 A1 | 7/2018 | Freestone | |
| 2019/0022343 A1 | 1/2019 | Kooij et al. | |
| 2019/0111227 A1 | 4/2019 | Veliss | |
| 2019/0151594 A1 | 5/2019 | Gunaratnam et al. | |
| 2022/0409841 A1 | 12/2022 | Wagner et al. | |
| 2024/0024607 A1 | 1/2024 | Kooij et al. | |

FOREIGN PATENT DOCUMENTS

| | | | |
|---|---|---|---|
| WO | WO 98/034665 A1 | 8/1998 | |
| WO | WO 2000/078381 A1 | 12/2000 | |
| WO | WO 2004/073778 A1 | 9/2004 | |
| WO | WO 2005/063328 A1 | 7/2005 | |
| WO | WO 2006/074513 A1 | 7/2006 | |
| WO | WO 2006/130903 A1 | 12/2006 | |
| WO | WO 2009/052560 A1 | 4/2009 | |
| WO | WO 2010/135785 A1 | 12/2010 | |
| WO | WO 2012/171072 A1 | 12/2012 | |
| WO | WO 2013/020167 A1 | 2/2013 | |
| WO | 2014/025267 A1 | 2/2014 | |
| WO | 2014/075141 A1 | 5/2014 | |
| WO | WO 2014/175753 A1 | 10/2014 | |
| WO | 2016/043603 A1 | 3/2016 | |
| WO | WO 2016/193859 A1 | 12/2016 | |
| WO | WO 2017/017573 A1 | 2/2017 | |
| WO | WO-2017124155 A1 * | 7/2017 | ............ A61M 16/06 |
| WO | 2017/158544 A1 | 9/2017 | |
| WO | 2019/003094 A1 | 1/2019 | |
| WO | WO 2019/119058 A1 | 6/2019 | |
| WO | WO 2019/185474 A1 | 10/2019 | |

OTHER PUBLICATIONS

International Preliminary Report on Patentability dated Nov. 17, 2021 issued in PCT/AU2020/051286 (51 pages).
International Search Report dated Mar. 15, 2021 issued in PCT/AU2020/051286 (15 pages).
Written Opinion of the International Searching Authority dated Mar. 15, 2021 issued in PCT/AU2020/051286 (9 pages).
Extended European Search Report dated Nov. 22, 2023 issued in European Application No. 20894269.8 (10 pages).
Office Action dated Jul. 16, 2024 issued in Japanese Application No. 2022-531567 with English translation (13 pages).

* cited by examiner

Copyright 2012 ResMed Limited

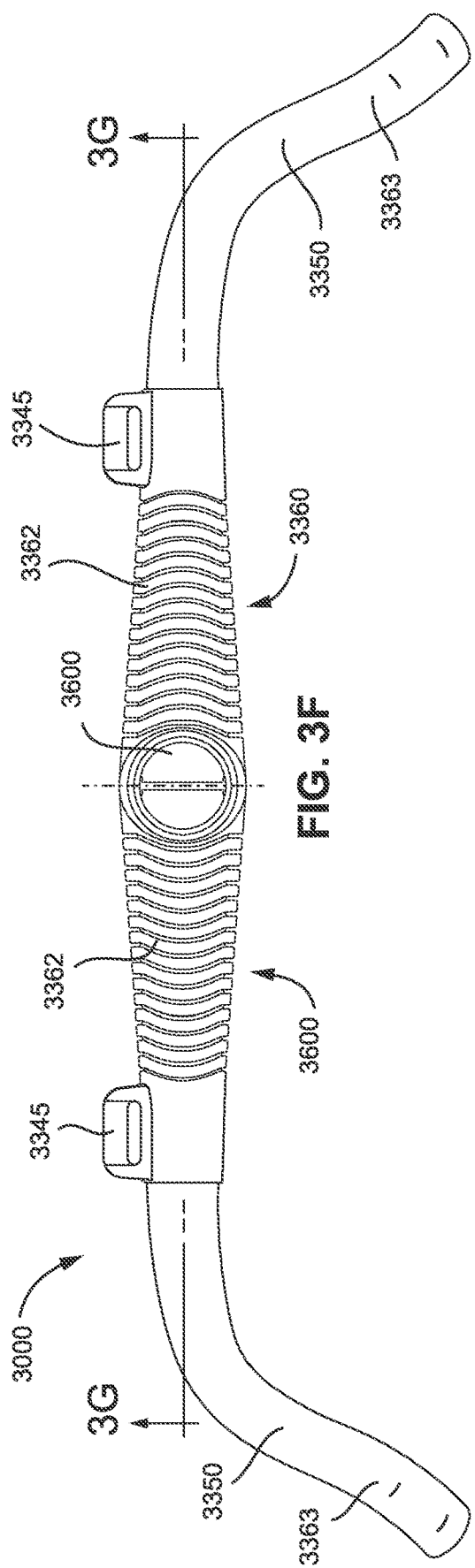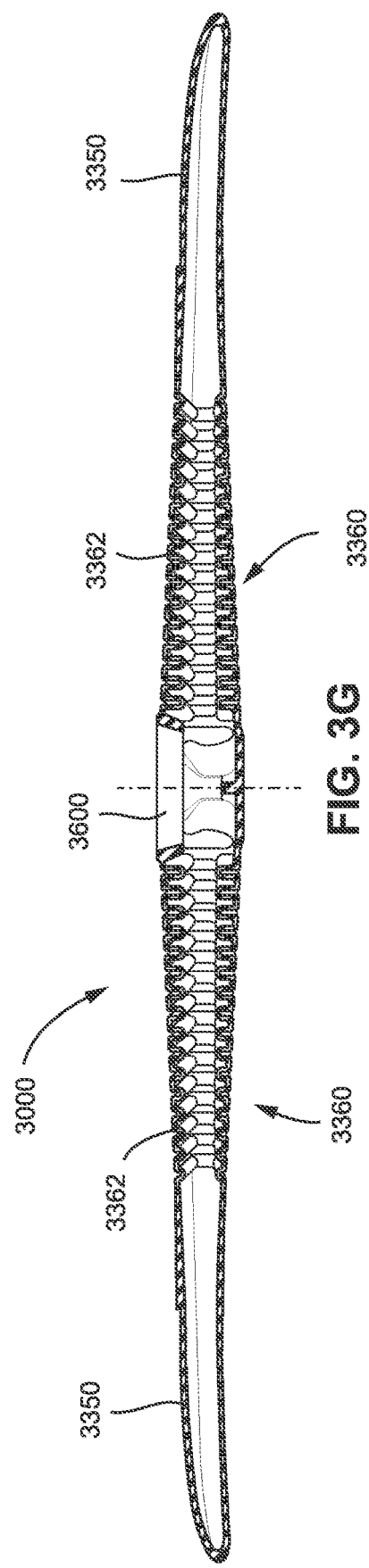
FIG. 3F
FIG. 3G

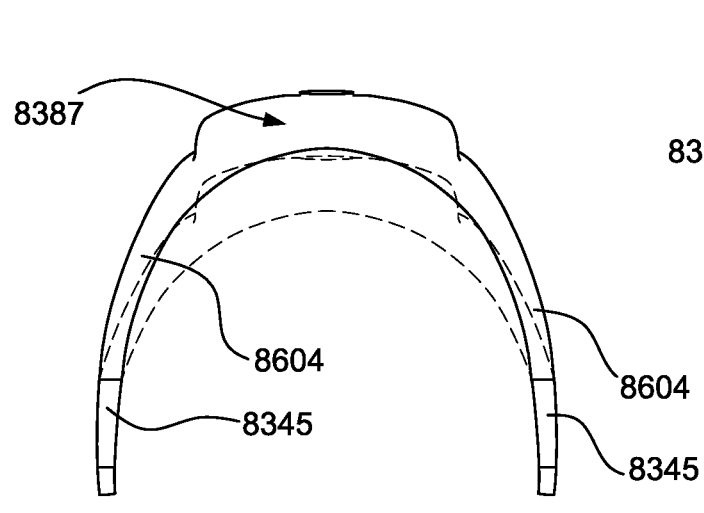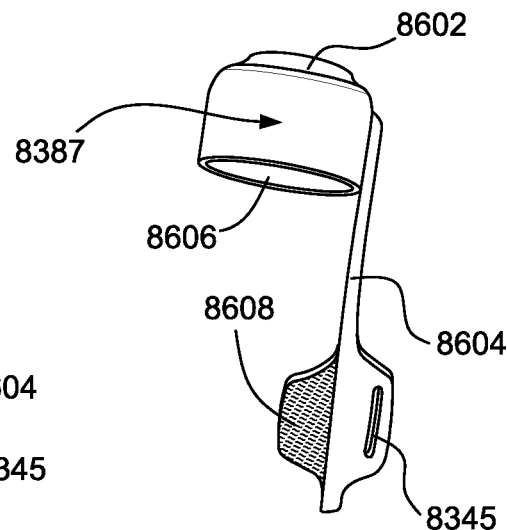
FIG. 21A-1
FIG. 21A-2
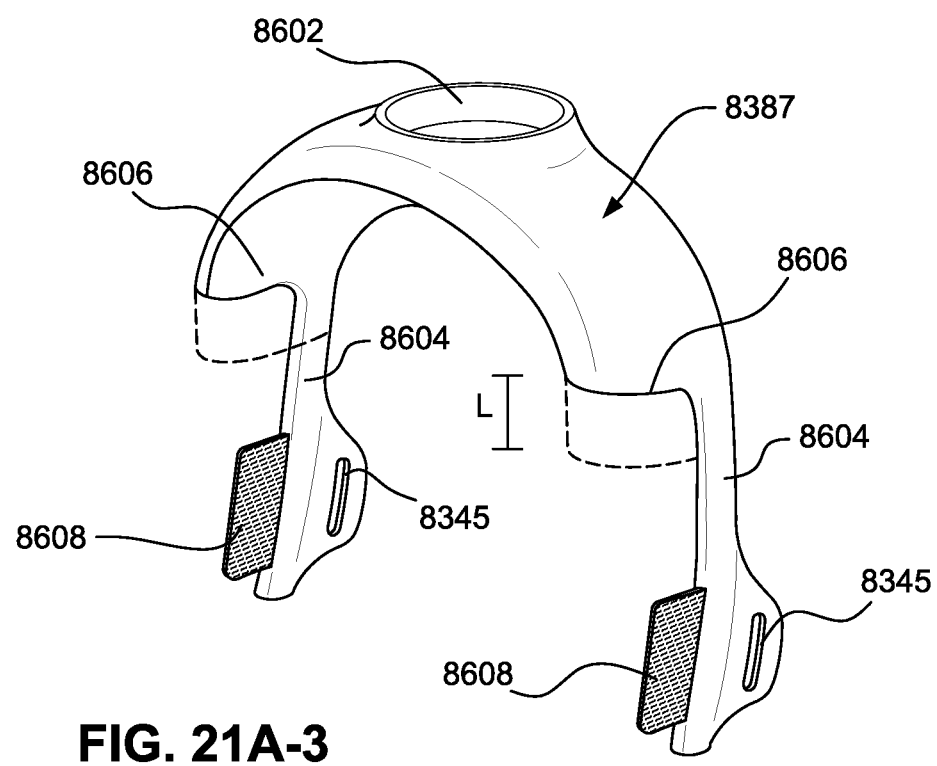
FIG. 21A-3

ADJUSTABLE HEADGEAR TUBING FOR A PATIENT INTERFACE

1 CROSS-REFERENCE TO RELATED APPLICATIONS

This application is a continuation of U.S. application Ser. No. 17/780,804, filed May 27, 2022, now allowed, which is the U.S. national phase of International Application No. PCT/AU2020/051286 filed Nov. 27, 2020 which designated the U.S. and claims priority to Australian Provisional Patent Application No. 2020900503, filed Feb. 21, 2020, and Australian Provisional Patent Application No. 2019904513, filed Nov. 29, 2019, the entire contents of each of which are hereby incorporated by reference.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE TECHNOLOGY

5.1 Field of the Technology

The present technology relates to one or more of the detection, diagnosis, treatment, prevention and amelioration of respiratory-related disorders. The present technology also relates to medical devices or apparatus, and their use.

Certain forms of the present technology relate to patient interfaces used in the treatment of respiratory, prevention and amelioration of respiratory-related disorders.

5.2 Description of the Related Art

5.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

5.2.2 Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

5.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier and a patient interface.

5.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

5.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks. An oro-nasal mask may include a compact full-face mask without a forehead support. Alternatively an oro-nasal mask may include a full-face mask that seals around the entrance of the mouth and nose, wherein the nose seal includes a cradle that seals below the lateral cartilage.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO 2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

5.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use. When designed to be worn on the patient's head, such harnesses may be referred to as headgear.

5.2.3.1.3 Pressurised Air Conduit

In one type of treatment system, a flow of pressurised air is provided to a patient interface through a conduit in an air circuit that fluidly connects to the patient interface so that, when the patient interface is positioned on the patient's face during use, the conduit extends out of the patient interface forwards away from the patient's face. This may sometimes be referred to as an "elephant trunk" style of interface.

Some patients find such interfaces to be unsightly and are consequently deterred from wearing them, reducing patient compliance. Additionally, conduits connecting to an interface at the front of a patient's face may sometimes be vulnerable to becoming tangled up in bed clothes.

5.2.3.1.4 Pressurised Air Conduit Used for Positioning/Stabilising the Seal-Forming Structure An alternative type of treatment system which seeks to address these problems comprises a patient interface in which a tube that delivers pressurised air to the patient's airways also functions as part of the headgear to position and stabilise the seal-forming portion of the patient interface to the appropriate part of the patient's face. This type of patient interface may be referred to as incorporating 'headgear tubing' or 'conduit headgear'. Such patient interfaces allow the conduit in the air circuit providing the flow of pressurised air from a respiratory pressure therapy device to connect to the patient interface in a position other than in front of the patient's face. One example of such a treatment system is disclosed in US Patent Publication No. US 2007/0246043, the contents of which are incorporated herein by reference, in which the conduit connects to a tube in the patient interface through a port positioned in use on top of the patient's head.

The Philips DreamWear™ nasal mask includes such headgear tubing. One problem with this mask is that the length of the headgear tubes cannot be adjusted. Consequently the DreamWear™ mask is supplied in different sizes to cater for different sized patient faces. However, this creates complexity and cost to manufacture the DreamWear™ mask and larger packaging. Additionally, the supply of discretely sized masks limits the extent to which differently sized patient heads can be accommodated, for example, if the patient's head size falls between or outside the mask sizes provided.

Patient interfaces incorporating headgear tubing may provide some advantages, for example avoiding a conduit connecting to the patient interface at the front of a patient's face, which may be unsightly and obtrusive. However, it is desirable for patient interfaces incorporating headgear tubing to be comfortable for a patient to wear over a prolonged duration when the patient is asleep while forming an effective seal with the patient's face.

5.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

5.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

6 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

An aspect of certain forms of the present technology is to provide methods and/or apparatus that improve the compliance of patients with respiratory therapy.

One form of the present technology comprises a patient interface for delivery of a supply of pressurised breathable gas to an entrance of a patient's airways.

Another aspect of one form of the present technology comprises a positioning and stabilising structure to hold a seal-forming structure in a therapeutically effective position on a head of a patient. The seal-forming structure may be constructed and arranged to form a seal with a region of the patient's face surrounding an entrance to the patient's airways for sealed delivery of a flow of air at a therapeutic pressure of at least 4 cmH$_2$O with respect to ambient air pressure throughout the patient's respiratory cycle in use. The positioning and stabilising structure may comprise at least one gas delivery tube to deliver the flow of air to the entrance of a patient's airways via the seal-forming structure.

Another aspect of one form of the present technology comprises a positioning and stabilising structure to hold a seal-forming structure in a therapeutically effective position on a head of a patient. The seal-forming structure may be constructed and arranged to form a seal with a region of the patient's face surrounding an entrance to the patient's airways for sealed delivery of a flow of air at a therapeutic pressure of at least 4 cmH$_2$O with respect to ambient air pressure throughout the patient's respiratory cycle in use. The positioning and stabilising structure may comprise at least one gas delivery tube to deliver the flow of air to the entrance of a patient's airways via the seal-forming structure. The at least one gas delivery tube may be constructed and arranged to contact, in use, at least a region of the patient's head superior to an otobasion superior of the patient's head. The positioning and stabilising structure may comprise an adjustment mechanism for adjustment of a length of the at least one gas delivery tube to enable the positioning and stabilising structure to fit different size heads. The positioning and stabilising structure may comprise a bias mechanism to impart a biasing force along at least a part of a length of the at least one gas delivery tube to urge the seal-forming structure towards the entrance of the patient's airways in use.

Another aspect of one form of the present technology comprises a patient interface comprising a plenum chamber that may be pressurized to a therapeutic pressure of at least 4 cmH$_2$O above ambient air pressure. The plenum chamber may include a plenum chamber inlet port sized and structured to receive a flow of air at the therapeutic pressure for breathing by a patient. The patient interface may comprise a seal-forming structure constructed and arranged to form a seal with a region of the patient's face surrounding an entrance to the patient's airways such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may comprise a positioning and stabilising structure to hold the seal-forming structure in a therapeutically effective position on the patient's head.

Another aspect of one form of the present technology comprises a patient interface comprising a plenum chamber pressurisable to a therapeutic pressure of at least 4 cmH$_2$O above ambient air pressure. The plenum chamber may include a plenum chamber inlet port sized and structured to receive a flow of air at the therapeutic pressure for breathing by a patient. The patient interface may comprise a seal-forming structure constructed and arranged to form a seal with a region of the patient's face surrounding an entrance to the patient's airways such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may comprise a connection port to fluidly connect, in use, with an air circuit connected to the flow of air. The connection port may be located, in use, proximal a top, side or rear portion of a patient's head. The patient interface may comprise a positioning and stabilising structure to hold the seal-forming structure in a therapeutically effective position on the patient's head. The positioning and stabilising structure may comprise at least one gas delivery tube to deliver a flow of air to the entrance of a patient's airways via the seal-forming structure. The at least one gas delivery tube may be constructed and arranged to contact, in use, at least a region of the patient's head superior to an otobasion superior of the patient's head. The positioning and stabilising structure may comprise an adjustment mechanism for adjustment of a length of the at least one gas delivery tube to enable the positioning and stabilising structure to fit different size heads. The positioning and stabilising structure may comprise a bias mechanism to impart a biasing force along at least a part of a length of the at least one gas delivery tube to urge the seal-forming structure towards the entrance of the patient's airways in use.

Another aspect of one form of the present technology comprises a positioning and stabilising structure to hold a seal-forming structure in a therapeutically effective position on a head of a patient. The seal-forming structure may be constructed and arranged to form a seal with a region of the patient's face surrounding an entrance to the patient's airways for sealed delivery of a flow of air at a therapeutic pressure of at least 4 cmH$_2$O with respect to ambient air pressure throughout the patient's respiratory cycle in use. The positioning and stabilising structure may comprise at least one tie. The at least one tie may be configured to contact the patient's head in use. The at least one tie may comprise at least one gas delivery tube to deliver the flow of air to the entrance of a patient's airways via the seal-forming structure. The at least one gas delivery tube may be constructed and arranged to overlie, in use, at least a region of the patient's head superior to an otobasion superior of the patient's head. The positioning and stabilising structure may comprise an adjustment mechanism for adjustment of the at least one tie to enable the positioning and stabilising structure to fit different size heads. The positioning and stabilising structure may be configured such that, in use, the adjustment mechanism is positioned out of contact with a patient's face.

Another aspect of one form of the present technology comprises a patient interface comprising a plenum chamber pressurisable to a therapeutic pressure of at least 4 cmH$_2$O above ambient air pressure. The plenum chamber may include a plenum chamber inlet port sized and structured to receive a flow of air at the therapeutic pressure for breathing by a patient. The patient interface may comprise a seal-forming structure constructed and arranged to form a seal with a region of the patient's face surrounding an entrance to the patient's airways such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may comprise a connection port to fluidly connect, in use, with an air circuit connected to the flow of air. The connection port may be located, in use, proximal a top, side or rear portion of a patient's head. The patient interface may comprise a positioning and stabilising structure to hold the seal-forming structure in a therapeutically effective position on the patient's head. The positioning and stabilising structure may comprise at least one tie. The at least one tie may be configured to contact the patient's head in use. The at least one tie may comprise at least one gas delivery tube to deliver the flow of air to the entrance of a patient's airways via the seal-forming structure. The at least one gas delivery tube may be constructed and arranged to overlie, in use, at least a region of the patient's head superior to an otobasion superior of the patient's head. The positioning and stabilising structure may comprise an adjustment mechanism for adjustment of the at least one tie to enable the positioning and stabilising structure to fit different size heads. The positioning and stabilising structure may be configured such that, in use, the adjustment mechanism is positioned out of contact with a patient's face.

Another aspect of one form of the present technology comprises a patient interface comprising a plenum chamber pressurisable to a therapeutic pressure of at least 4 cmH$_2$O above ambient air pressure. The plenum chamber may include a plenum chamber inlet port sized and structured to receive a flow of air at the therapeutic pressure for breathing by a patient. The patient interface may comprise a seal-forming structure constructed and arranged to form a seal with a region of the patient's face surrounding an entrance to the patient's airways such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may comprise a positioning and stabilising structure to hold the seal-forming structure in a therapeutically effective position on the patient's head. The positioning and stabilising structure may comprise a first tube portion constructed and arranged to overlay a region of the patient's head superior to an otobasion superior of the patient's head in use. The positioning and stabilising structure may comprise a tie portion to overlay or lie inferior to the occipital bone of the patient's head in use. The patient interface may comprise a vent structure to allow a continuous flow of gases exhaled by the patient from an interior of the plenum chamber to ambient, said vent structure being sized and shaped to maintain the therapeutic pressure in the plenum chamber in use. The first tube portion may be configured to conduct at least a portion of the flow of air for breathing by the patient. The first tube portion may be configured to be in tension in use. The first tube portion may include a lengthwise adjustment mechanism.

Another aspect of one form of the present technology comprises a positioning and stabilising structure to hold a seal-forming structure in a therapeutically effective position on a head of a patient. The seal-forming structure may be constructed and arranged to form a seal with a region of the patient's face surrounding an entrance to the patient's airways for sealed delivery of a flow of air at a therapeutic pressure of at least 4 cmH$_2$O with respect to ambient air pressure throughout the patient's respiratory cycle in use. The positioning and stabilising structure may comprise a first conduit portion constructed and arranged to overlay a region of the patient's head superior to an otobasion superior of the patient's head in use. The positioning and stabilising structure may comprise a tie portion to overlay or lie inferior to the occipital bone of the patient's head in use. The first conduit portion may be configured to conduct at least a portion of the flow of air for breathing by the patient. The first conduit portion may be configured to be in tension in use. The first conduit portion may include a lengthwise adjustment mechanism.

Another aspect of one form of the present technology comprises a patient interface comprising a plenum chamber pressurisable to a therapeutic pressure of at least 4 cmH$_2$O above ambient air pressure. The plenum chamber may include a plenum chamber inlet port sized and structured to receive a flow of air at the therapeutic pressure for breathing by a patient. The patient interface may comprise a seal-forming structure constructed and arranged to form a seal with a region of the patient's face surrounding an entrance to the patient's airways such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may comprise a positioning and stabilising structure to provide an elastic force to hold a seal-forming structure in a therapeutically effective position on a patient's head for sealed delivery of the flow of air at the therapeutic pressure. The positioning and stabilising structure may comprise a tie. The tie may be constructed and arranged so that at least a portion of the tie overlies a region of the patient's head superior to an otobasion superior of the patient's head in use. The tie may comprise a length-adjustable gas delivery tube to deliver the flow of air to the entrance of a patient's airways via the seal-forming structure. The gas delivery tube may be configured to contact a portion of the patient's head in use. The positioning and stabilising structure may comprise a bias mechanism to impart a biasing force upon the length-adjustable gas delivery tube to urge the seal forming structure towards the entrance of the patient's airways in use.

Another aspect of one form of the present technology comprises a positioning and stabilising structure to hold a seal-forming structure in a therapeutically effective position on a head of a patient. The seal-forming structure may be constructed and arranged to form a seal with a region of the patient's face surrounding an entrance to the patient's airways for sealed delivery of a flow of air at a therapeutic pressure of at least 4 cmH$_2$O with respect to ambient air pressure throughout the patient's respiratory cycle in use. The positioning and stabilising structure may comprise a tie. The tie may be constructed and arranged so that at least a portion of the tie overlies a region of the patient's head superior to an otobasion superior of the patient's head in use. The tie may comprise a length-adjustable gas delivery tube to deliver the flow of air to the entrance of a patient's airways via the seal-forming structure. The gas delivery tube may be configured to contact a portion of the patient's head in use. The positioning and stabilising structure may comprise a bias mechanism to impart a biasing force upon the length-adjustable gas delivery tube to urge the seal forming structure towards the entrance of the patient's airways in use.

Another aspect of one form of the present technology comprises an inflatable positioning and stabilising structure to maintain a seal at an entrance of the patient's airways formed by a seal-forming structure of a patient interface for sealed delivery of a flow of air at a continuously positive pressure with respect to ambient air pressure and configured to maintain a therapy pressure in a range of about 4 cmH$_2$O to about 30 cmH$_2$O above ambient air pressure in use, throughout the patient's respiratory cycle, while the patient is sleeping, to ameliorate sleep disordered breathing. The positioning and stabilising structure may comprise at least one gas delivery tube to deliver the flow of air to the entrance of a patient's airways via the seal-forming structure. The positioning and stabilising structure may also comprise an adjustment mechanism to enable dimensional adjustment of the positioning and stabilising structure. The positioning and stabilising structure may also comprise a bias mechanism to impart a biasing force upon the adjustment mechanism and urge the seal-forming structure towards the entrance of the patient's airways.

Another aspect of one form of the present technology comprises a patient interface for delivery of a supply of pressurised air at a continuously positive pressure with respect to ambient air pressure to an entrance of a patient's airways, the patient interface being configured to maintain a therapy pressure in a range of about 4 cmH$_2$O to about 30 cmH$_2$O above ambient air pressure in use, throughout the patient's respiratory cycle, while the patient is sleeping, to ameliorate sleep disordered breathing. The patient interface may comprise a connection port to fluidly connect, in use, with an air circuit connected to the supply of pressurised air, the connection port being located, in use, proximal a top, side or rear portion of a patient's head. The patient interface may also comprise a seal-forming structure to seal with an area surrounding the entrance to the patient's airways. The patient interface may also comprise an inflatable positioning and stabilising structure to maintain the seal formed by the seal-forming structure. The positioning and stabilising structure may comprise at least one gas delivery tube to deliver the flow of air to the entrance of a patient's airways via the seal-forming structure.

Another aspect of a related form of the present technology comprises a patient interface comprising a positioning and stabilising structure comprising an adjustment mechanism to enable dimensional adjustment of the positioning and stabilising structure.

Another aspect of a related form of the present technology comprises a patient interface comprising a bias mechanism to impart a biasing force upon the adjustment mechanism and urge the seal-forming structure towards the entrance of the patient's airways.

Another aspect of one form of the present technology comprises an inflatable positioning and stabilising structure to maintain a seal at an entrance of the patient's airways formed by a seal-forming structure of a patient interface for sealed delivery of a flow of air at a continuously positive pressure with respect to ambient air pressure and configured to maintain a therapy pressure in a range of about 4 cmH$_2$O to about 30 cmH$_2$O above ambient air pressure in use, throughout the patient's respiratory cycle, while the patient is sleeping, to ameliorate sleep disordered breathing. The positioning and stabilising structure may comprise at least one gas delivery tube to deliver the flow of air to the entrance of a patient's airways via the seal-forming structure. The positioning and stabilising structure may also comprise an adjustment mechanism to enable dimensional adjustment of the positioning and stabilising structure. The positioning and stabilising structure may be configured such that, in use, the adjustment mechanism is positioned out of contact with a patient's cheek region.

Another aspect of one form of the present technology comprises a patient interface for delivery of a supply of pressurised air at a continuously positive pressure with respect to ambient air pressure to an entrance of a patient's airways, the patient interface being configured to maintain a therapy pressure in a range of about 4 cmH$_2$O to about 30 cmH$_2$O above ambient air pressure in use, throughout the patient's respiratory cycle, while the patient is sleeping, to ameliorate sleep disordered breathing. The patient interface may comprise a positioning and stabilising structure. The positioning and stabilising structure may comprise at least one gas delivery tube to deliver the flow of air to the entrance of a patient's airways via the seal-forming structure. The positioning and stabilising structure may also comprise an adjustment mechanism to enable dimensional adjustment of the positioning and stabilising structure. The positioning and stabilising structure may be configured such that, in use, the adjustment mechanism is positioned out of contact with a patient's cheek region.

Another aspect of one form of the present technology comprises a positioning and stabilising structure to hold a seal-forming structure in a therapeutically effective position on a head of a patient, the seal-forming structure being constructed and arranged to form a seal with a region of the patient's face surrounding an entrance to the patient's airways for sealed delivery of a flow of air at a therapeutic pressure of at least 4 cmH2O with respect to ambient air pressure throughout the patient's respiratory cycle in use. The positioning and stabilising structure may comprise a front hoop extending, in use, across the patient's cheek regions and arranged to contact, in use, regions of the patient's head superior to an otobasion superior of the patient's head. The positioning and stabilising structure may also comprise a rear strap configured, in use, to pass around the back of the patient's head. The positioning and stabilising structure may also comprise an adjustment mechanism for adjustment of the front hoop and the rear strap relative to the patient's head. The adjustment mechanism may be arranged in a single operation to adjust both the front hoop and rear strap to enable the positioning and stabilising structure to fit different size heads.

In some examples, the adjustment mechanism may comprise one or more tube insert members configured to be selectably fluidly connected to the gas delivery tube to alter the length of the gas delivery tube.

In some examples, a) a link member connects two sections of the front hoop; b) the adjustment mechanism is operable to adjust a length of the link member between the two hoop sections; c) adjustment of the length adjusts both the front hoop and rear strap simultaneously; d) adjustment of the length of the link between the two sections of the front hoop adjusts an effective length of the front hoop by adjusting an allowable distance between the two sections of the front hoop; e) adjustment of the length of the link causes a corresponding adjustment to the effective length of the rear strap; f) the link forms part of the rear strap; g) opposite end regions of the rear strap are connected to, or adjacent, respective ones of the two sections of the front hoop; h) the adjustment mechanism is selected from a group consisting of a rack and pinion, a draw string, and a releasable mechanical coupling; i) the adjustment mechanism is configured to allow adjustment of the link member; j) the adjustment mechanism enables the length of the link to be adjusted through a continuous range of lengths; and/or k) the front hoop and/or the rear strap include the link member.

In some examples, a) there is at least one gas delivery tube to deliver the flow of air to the entrance of the patient's airways via the seal-forming structure; b) the front hoop includes a lower portion of the at least one gas delivery tube; c) the positioning and stabilising structure includes a de-coupling mechanism for decoupling positional adjustment of an upper portion of the at one gas delivery tube from movement of the seal-forming structure away from the patient's face in use to enable positional adjustment of the upper portion of the gas delivery tubes on the patient's head; d) the adjustment mechanism is located anterior to the decoupling structure, in use; e) the upper portions are bendable and include corrugations and/or concertinas to enable positional adjustment of the upper portion of the at least one tube on the patient's head, in use; and/or f) at least one swivel including a connection port configured to connect to an air circuit; g) the at least one swivel is configured to allow relative rotation between the upper portion of the at least one gas delivery tube and the air circuit connected to the connection port.

In some examples, a) the de-coupling structure may be fluidly connected, in use, with the air circuit connected to a supply of pressurised air; b) the de-coupling structure may be located, in use, proximal a top, side, or rear portion of a patient's head; c) two gas delivery tubes may fluidly connected between the de-coupling structure and the seal-forming structure; d) lower portions of each gas delivery tube may extend, in use, across one of the patient's cheek regions; e) the two gas delivery tubes may be on different sides of the patient's head; f) the lower portions of the two gas delivery tubes at least partially form part of the front hoop; g) each of the respective lower portions of the gas delivery tubes comprises a respective one of the two sections of the front hoop; h) the de-coupling structure is located, in use, on top of the patient's head; i) the adjustment mechanism is located, in use, on the top of the patient's head adjacent the de-coupling structure; and/or j) the de-coupling structure is y-shaped or v-shaped.

In some examples: a) the at least one swivel includes a first swivel and a second swivel configured to rotate relative to the first swivel; b) the first swivel rotates about a first axis, and the second swivel rotates about a second axis perpendicular to the first axis; c) the first swivel is rotatable independently of the second swivel; and/or d) the at least one swivel rotates about a swivel axis, the swivel axis oriented substantially parallel to an axis along the bendable portion.

In some examples, a) the adjustment mechanism incorporates one or more cables connected to both the hoop and rear strap and a controller to translate the one or more cables to induce adjustment of the hoop and rear strap; b) the controller includes a rotatable dial; c) the adjustment mechanism comprises a plurality of cables, and a rate of translation of the plurality of cables is uniform; and/or d) the adjustment mechanism comprises a plurality of cables, and a rate of translation of the plurality of cables is non uniform.

In some forms, a) the one or more cables are formed as a drawstring threaded through the front hoop and/or the rear strap; b) the adjustment mechanism includes a release button configured to be engaged by the user in order to adjust a length of the drawstring; c) the drawstring is threaded through an opening; d) the release button is configured to change the diameter of the opening from a small diameter to a large diameter; e) the opening configured to engage the drawstring in the small diameter and provide a frictional force to the drawstring; f) a control unit controls the adjustment mechanism; g) the control unit is operated directly by at least one button; and/or h) the control unit is operated indirectly by a remote device.

In some examples, a) the adjustment mechanism is positioned superior to the otobasion superior of the patient's head, in use; and/or b) an angle of the rear strap to the front hoop is adjustable under operation of the adjustment mechanism.

Another aspect of one form of the present technology comprises a positioning and stabilising structure to hold a seal-forming structure in a therapeutically effective position on a head of a patient, the seal-forming structure being constructed and arranged to form a seal with a region of the patient's face surrounding an entrance to the patient's airways for sealed delivery of a flow of air at a therapeutic pressure of at least 4 cmH2O with respect to ambient air pressure throughout the patient's respiratory cycle in use, the positioning and stabilising structure comprising. The positioning and stabilising structure may comprise a front hoop extending, in use, across the patient's cheek regions and arranged to contact, in use, regions of the patient's head superior to an otobasion superior of the patient's head. The front hoop may comprise lower portions of two gas delivery tubes fluidly connected to the seal-forming structure. Each lower portion of the gas delivery tube may extend, in use, across one of the patient's cheek regions, the two gas delivery tubes may be on different sides of the patient's head. The front hoop may also comprise a link connecting the two gas delivery tubes between the lower portions and upper portions of the two gas delivery tubes. The positioning and stabilising structure may also comprise a rear strap configured, in use, to pass around the back of the patient's head. The positioning and stabilising structure may also comprise a de-coupling mechanism for decoupling positional adjustment of the upper portions of the gas delivery tubes from movement of the seal-forming structure away from the patient's face in use to enable positional adjustment of the upper portions of the gas delivery tubes on the patient's head.

In some examples, a) the upper portions are bendable and include corrugations and/or concertinas on the upper portions to enable positional adjustment of the upper portions of the two gas delivery tubes on the patient's head in use; b) at least one swivel includes a connection port to connect to an air circuit; c) the at least one swivel is configured to allow relative rotation between the upper portions and the air circuit; d) the upper portions are positioned superior to an otobasion superior of the patient's head in use; d) the de-coupling structure is Y-shaped or V-shaped; and/or e) a chin strap extends, in use, across the patient's cheek regions and is arranged to contact, in use, regions of the patient's head inferior to an otobasion inferior of the patient's head.

In some examples: a) at least one swivel includes a first swivel and a second swivel configured to rotate relative to the first swivel; b) the first swivel rotates about a first axis, and the second swivel rotates about a second axis perpendicular to the first axis; c) the first swivel is rotatable independently of the second swivel; d) the de-coupling structure includes a tube connector coupled to the two gas delivery tubes, which diverge from the tube connector; e) the first swivel is directly connected to the tube connector; f) the tube connector is non-rotatable relative to the two gas delivery tubes; g) the first swivel is rotatable relative to the tube connector; and/or h) the at least one swivel rotates about a swivel axis, the swivel axis is oriented substantially parallel to an axis along the upper portions.

In some examples: a) there is an adjustment mechanism for adjustment of the front hoop and the rear strap relative to the patient's head; b) the adjustment mechanism is arranged in a single operation to adjust both the front hoop and the rear strap to enable the positioning and stabilising structure to fit different sized heads; c) the adjustment mechanism is operable to adjust a length of the link member between the lower portions; and/or d) adjustment of the length adjusts both the front hoop and the rear straps simultaneously.

Another aspect of one form of the present technology comprises a patient interface comprising a plenum chamber pressurisable to a therapeutic pressure of at least 4 cmH2O above ambient air pressure, said plenum chamber including a plenum chamber inlet port sized and structured to receive a flow of air at the therapeutic pressure for breathing by a patient. The patient interface may comprise a seal-forming structure constructed and arranged to form a seal with a region of the patient's face surrounding an entrance to the patient's airways such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may also comprise a connection port to fluidly connect, in use, with an air circuit connected to the flow of air. The connection port may be located, in use, proximal a top, side or rear portion of a patient's head. The patient interface may also comprise a positioning and stabilising structure. The positioning and stabilising structure may comprise a front hoop extending, in use, across the patient's cheek regions and arranged to contact, in use, regions of the patient's head superior to an otobasion superior of the patient's head. The positioning and stabilising structure may also comprise a rear strap configured, in use, to pass around the back of the patient's head. The positioning and stabilising structure may also comprise an adjustment mechanism for adjustment of the front hoop and the rear strap relative to the patient's head. The adjustment mechanism may be arranged in a single operation to adjust both the front hoop and rear strap to enable the positioning and stabilising structure to fit different size heads.

Another aspect of one form of the present technology comprises a patient interface comprising a plenum chamber pressurisable to a therapeutic pressure of at least 4 cmH2O above ambient air pressure. The plenum chamber may include a plenum chamber inlet port sized and structured to receive a flow of air at the therapeutic pressure for breathing by a patient. The patient interface may also comprise a seal-forming structure constructed and arranged to form a seal with a region of the patient's face surrounding an entrance to the patient's airways such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. A front hoop extends, in use, across the patient's cheek regions and arranged to contact, in use, regions of the patient's head superior to an otobasion superior of the patient's head. The front hoop may comprise lower portions of two gas delivery tubes fluidly connected to the seal-forming structure. Each lower portion of the gas delivery tube may extend, in use, across one of the patient's cheek regions. The two gas delivery tubes may be on different sides of the patient's head. The front hoop may also comprise a link connecting the two gas delivery tubes between the lower portions and upper portions of the two gas delivery tubes. The patient interface may also comprise a rear strap configured, in use, to pass around the back of the patient's head. The patient interface may also comprise a de-coupling mechanism for decoupling positional adjustment of the upper portions of the gas delivery tubes from movement of the seal forming structure away from the patient's face in use to enable positional adjustment of the upper portions of the gas delivery tubes on the patient's head.

In some examples, a system for treating a respiratory disorder includes a patient interface of either of the previous two aspects, an air circuit, and a source of air at a positive pressure with respect to the ambient air pressure.

Another aspect of one form of the present technology comprises a positioning and stabilising structure to hold a seal-forming structure in a therapeutically effective position on a head of a patient, the seal-forming structure being constructed and arranged to form a seal with a region of the patient's face surrounding an entrance to the patient's airways for sealed delivery of a flow of air at a therapeutic pressure of at least 4 cmH2O with respect to ambient air pressure throughout the patient's respiratory cycle in use. The positioning and stabilising structure may comprise at least one hoop extending, in use, across the patient's cheek regions and arranged to contact, in use, regions of the patient's head superior to an otobasion superior of the patient's head. The at least one hoop may comprise at least one gas delivery tube to deliver the flow of air to the entrance of a patient's airways via the seal-forming structure. The at least one gas delivery tube being constructed and arranged to overlie, in use, at least a region of the patient's head superior to an otobasion superior of the patient's head. The positioning and stabilising structure may also comprise an adjustment mechanism for adjustment of the at least one hoop to enable the positioning and stabilising structure to fit different size heads. The adjustment mechanism may comprise one or more tube insert members configured to be selectably fluidly connected to the gas delivery tube to alter the length of the gas delivery tube.

Another aspect of one form of the present technology comprises a positioning and stabilising structure to hold a seal-forming structure in a therapeutically effective position on a head of a patient, the seal-forming structure being constructed and arranged to form a seal with a region of the patient's face surrounding an entrance to the patient's airways for sealed delivery of a flow of air at a therapeutic pressure of at least 4 cmH2O with respect to ambient air pressure throughout the patient's respiratory cycle in use. The positioning and stabilising structure may comprise at least one hoop extending, in use, across the patient's cheek regions and arranged to contact, in use, regions of the patient's head superior to an otobasion superior of the patient's head. The at least one hoop may comprise at least one gas delivery tube to deliver the flow of air to the entrance of a patient's airways via the seal-forming structure. The at least one gas delivery tube being constructed and arranged to overlie, in use, at least a region of the patient's head superior to an otobasion superior of the patient's head. The positioning and stabilising structure may also comprise an adjustment mechanism for adjustment of the at least one hoop to enable the positioning and stabilising structure to fit different size heads. The adjustment mechanism may comprise a stretchable section of the gas delivery tube and one or more insert members configured to be selectably connected to the gas delivery tube to alter the length of the stretchable section of the gas delivery tube.

Another aspect of one form of the present technology comprises a positioning and stabilising structure to hold a seal-forming structure in a therapeutically effective position on a head of a patient, the seal-forming structure being constructed and arranged to form a seal with a region of the patient's face surrounding an entrance to the patient's airways for sealed delivery of a flow of air at a therapeutic pressure of at least 4 cmH2O with respect to ambient air pressure throughout the patient's respiratory cycle in use. The positioning and stabilising structure may comprise at least one hoop extending, in use, across the patient's cheek regions and arranged to contact, in use, regions of the patient's head superior to an otobasion superior of the patient's head. The at least one hoop may comprise at least one gas delivery tube to deliver the flow of air to the entrance of a patient's airways via the seal-forming structure. The at least one gas delivery tube being constructed and arranged to overlie, in use, at least a region of the patient's head superior to an otobasion superior of the patient's head. The positioning and stabilising structure may comprise a rear strap configured, in use, to pass around the back of the patient's head. The positioning and stabilising structure may also comprise an adjustment mechanism for adjustment of the at least one hoop to enable the positioning and stabilising structure to fit different size heads. The adjustment mechanism may comprise one or more insert members configured to be selectably connected to the gas delivery tube to alter the length of the gas delivery tube. At least one of the inserts includes a coupling to connect the rear strap to the gas delivery tube.

Another aspect of one form of the present technology comprises a positioning and stabilising structure to hold a seal-forming structure in a therapeutically effective position on a head of a patient, the seal-forming structure being constructed and arranged to form a seal with a region of the patient's face surrounding an entrance to the patient's airways for sealed delivery of a flow of air at a therapeutic pressure of at least 4 cmH2O with respect to ambient air pressure throughout the patient's respiratory cycle in use. The positioning and stabilising structure may comprise at least one hoop extending, in use, across the patient's cheek regions and arranged to contact, in use, regions of the patient's head superior to an otobasion superior of the patient's head. The at least one hoop may comprise at least one gas delivery tube to deliver the flow of air to the entrance of a patient's airways via the seal-forming structure. The at least one gas delivery tube being constructed and arranged to overlie, in use, at least a region of the patient's head superior to an otobasion superior of the patient's head. The positioning and stabilising structure may comprise an adjustment mechanism for adjustment of the at least one hoop to enable the positioning and stabilising structure to fit different size heads. The adjustment mechanism may comprise one or more inflatable portions.

Another aspect of certain forms of the present technology is a system for treating a respiratory disorder comprising a patient interface according to any one or more of the other aspects of the present technology, an air circuit and a source of air at positive pressure.

Another aspect of one form of the present technology is a patient interface that is moulded or otherwise constructed with a perimeter shape which is complementary to that of an intended wearer.

Another aspect of certain forms of the present technology is a patient interface comprising a seal-forming structure configured to leave the patient's mouth uncovered in use.

Another aspect of certain forms of the present technology is a patient interface comprising a seal-forming structure configured so that no part of the seal-forming structure enters the mouth in use.

Another aspect of certain forms of the present technology is a patient interface comprising a seal-forming structure configured so that the seal-forming structure does not extend internally of the patient's airways.

Another aspect of certain forms of the present technology is a patient interface comprising a seal-forming structure configured so that the seal-forming structure does not extend below a mental protuberance region in use.

Another aspect of certain forms of the present technology is a patient interface constructed and arranged to leave a patient's eyes uncovered in use.

Another aspect of certain forms of the present technology is a patient interface constructed and arranged to allow a patient to breathe ambient air in the event of a power failure.

Another aspect of certain forms of the present technology is a patient interface comprising a seal forming structure configured to form a seal on an underside of a patient's nose without contacting a nasal bridge region of the patient's nose.

Another aspect of certain forms of the present technology is a patient interface comprising a vent and a plenum chamber, wherein the patient interface is constructed and arranged so that gases from an interior of the plenum chamber may pass to ambient via the vent.

Another aspect of certain forms of the present technology is a patient interface constructed and arranged so that a patient may lie comfortably in a side or lateral sleeping position, in use of the patient interface.

Another aspect of certain forms of the present technology is a patient interface constructed and arranged so that a patient may lie comfortably in a supine sleeping position, in use of the patient interface.

Another aspect of certain forms of the present technology is a patient interface constructed and arranged so that a patient may lie comfortably in a prone sleeping position, in use of the patient interface.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7 BRIEF DESCRIPTION OF THE DRAWINGS

The present technology is illustrated by way of example, and not by way of limitation, in the figures of the accompanying drawings, in which like reference numerals refer to similar elements including:

7.1 Treatment Systems

FIG. 1A shows a system including a patient 1000 wearing a patient interface 3000, in the form of a nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown.

7.2 Respiratory System and Facial Anatomy

Figure 2A:
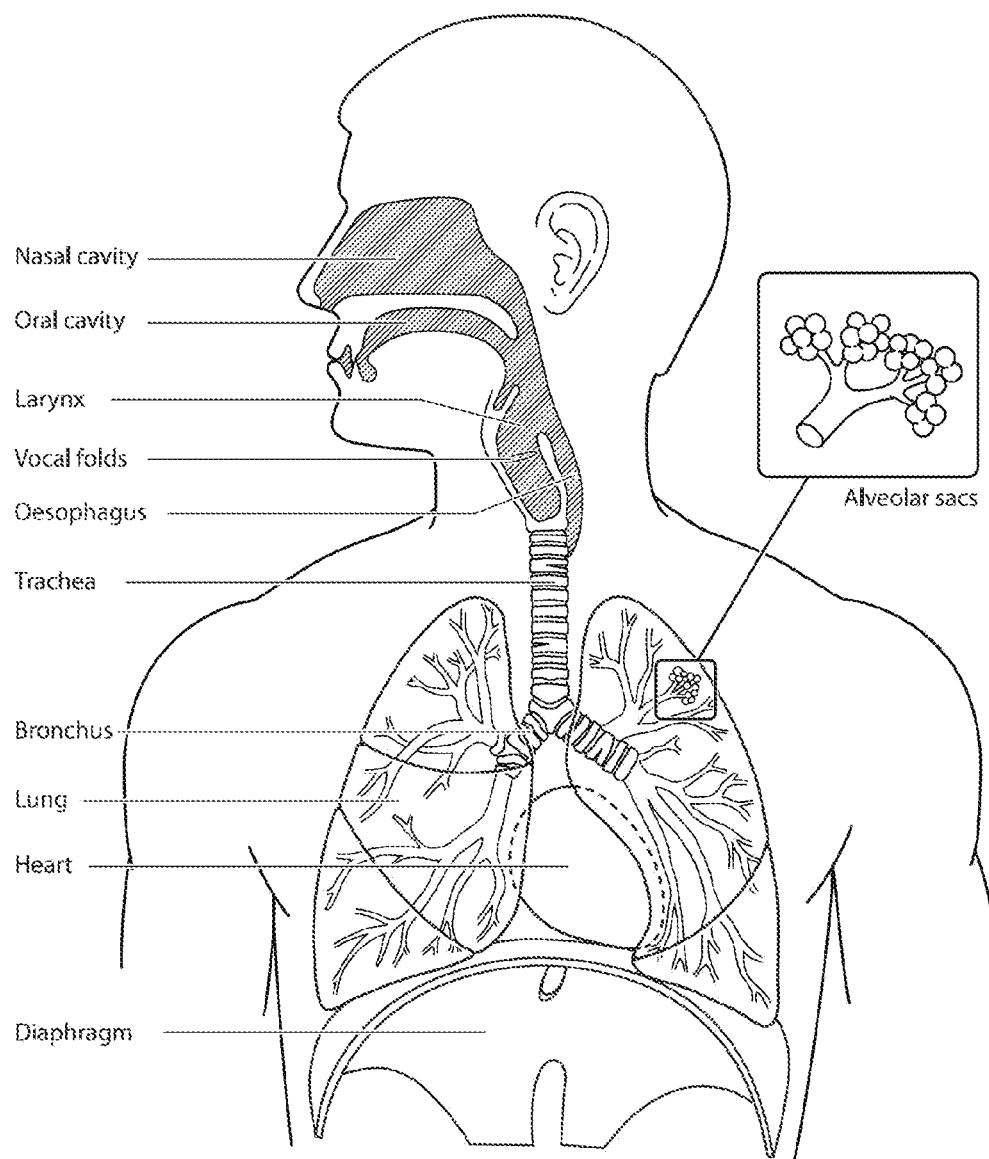

FIG. 2A shows an overview of a human respiratory system including the nasal and oral cavities, the larynx, vocal folds, oesophagus, trachea, bronchus, lung, alveolar sacs, heart and diaphragm.

Figure 2B:
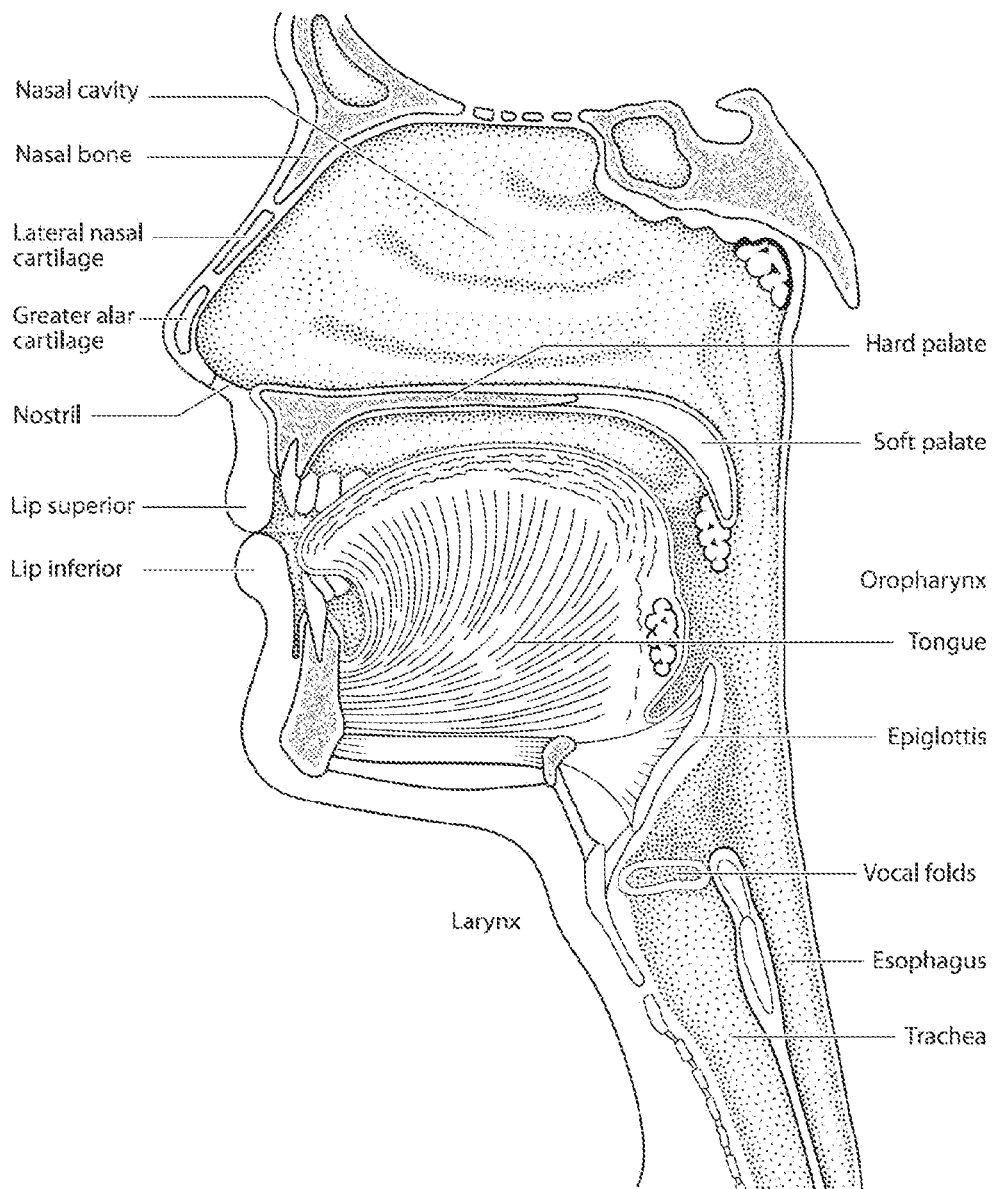

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
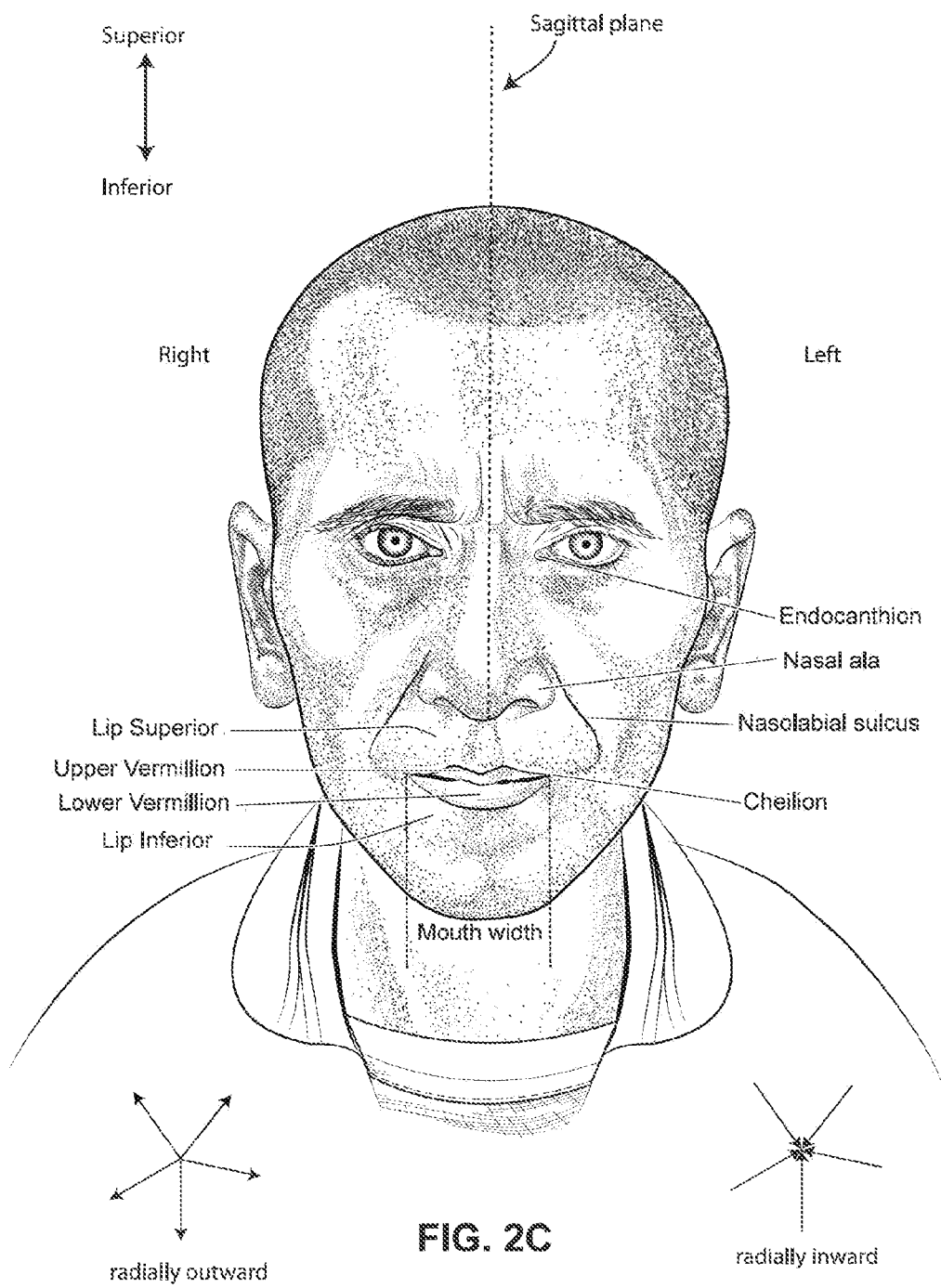

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
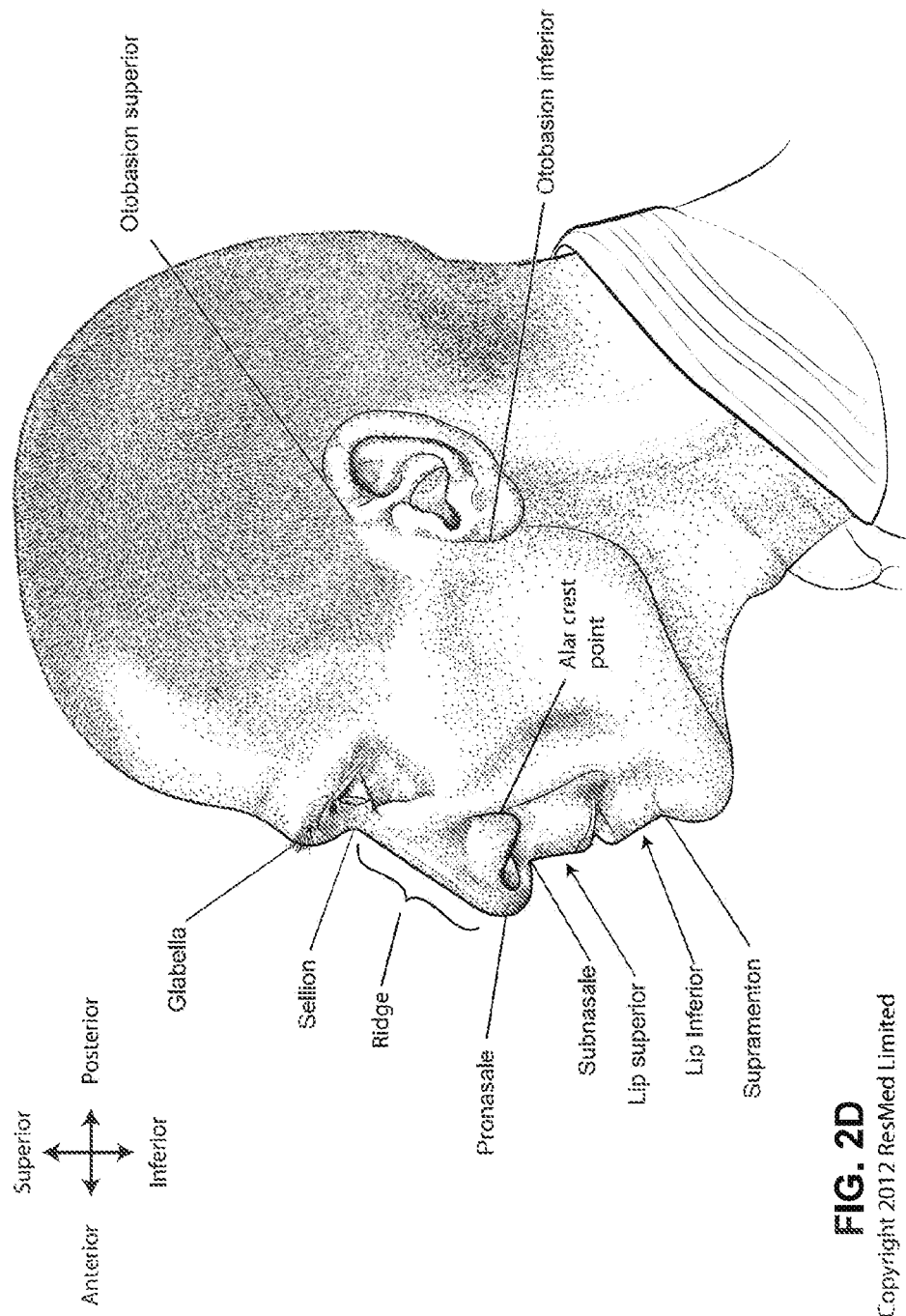

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
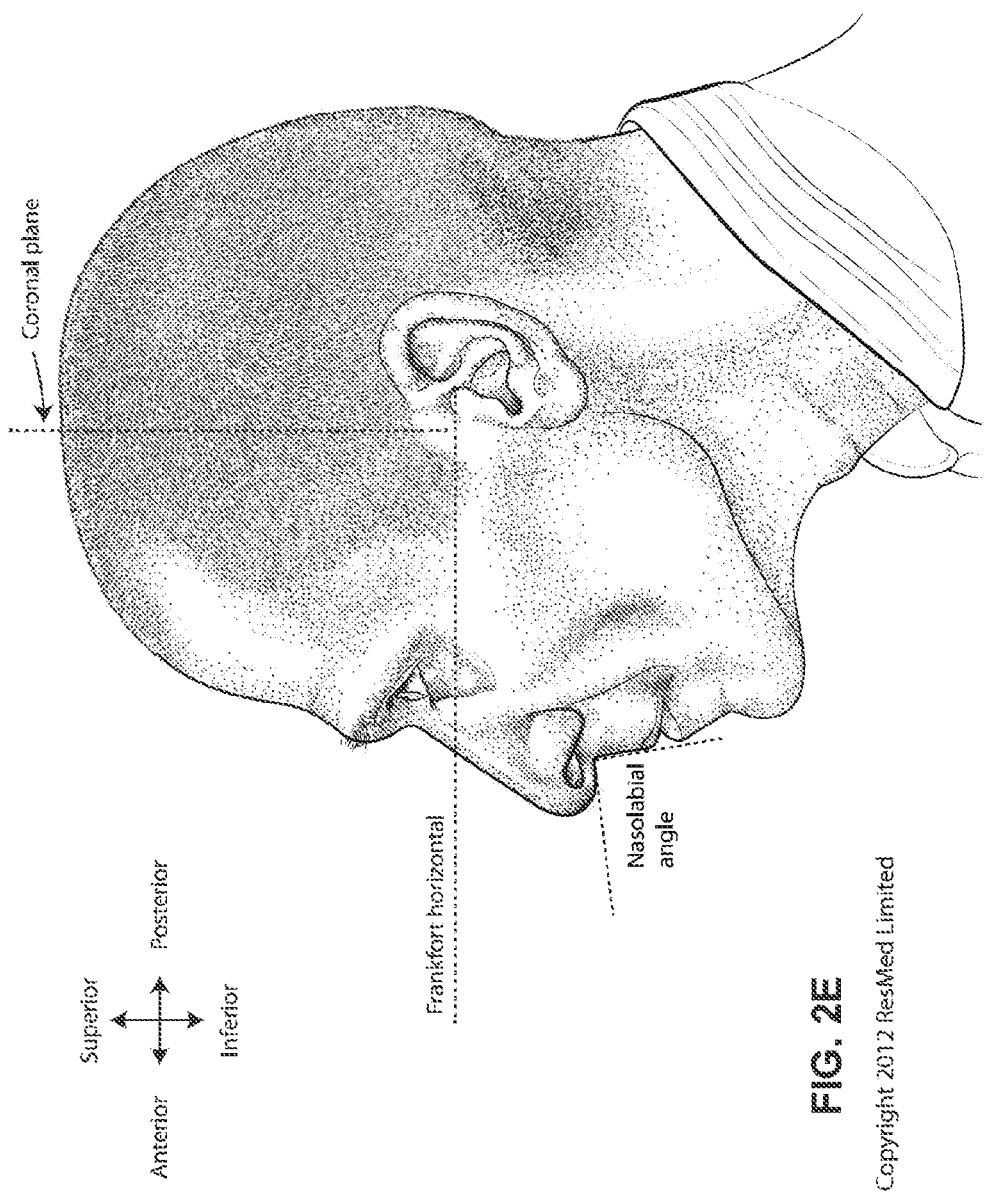

FIG. 2E is a further side view of a head. The approximate locations of the Frankfort horizontal and nasolabial angle are indicated. The coronal plane is also indicated.

Figure 2F:
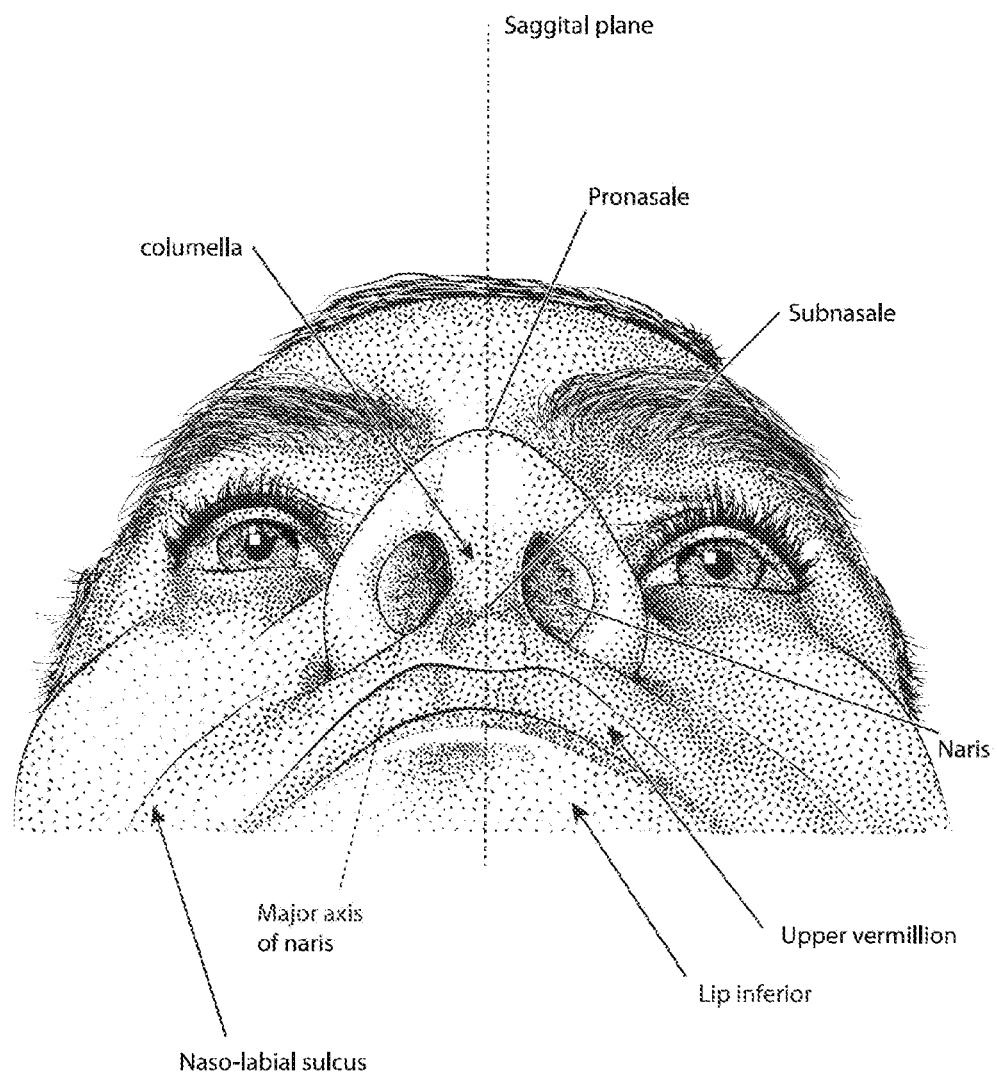

FIG. 2F shows a base view of a nose with several features identified including naso-labial sulcus, lip inferior, upper Vermilion, naris, subnasale, columella, pronasale, the major axis of a naris and the sagittal plane.

7.3 Patient Interface

FIGS. 3A, 3B, 3C, 3D and 3E show patient interfaces 3000 comprising positioning and stabilising structures 3300 in accordance with certain forms of the present technology.

Figure 3A:
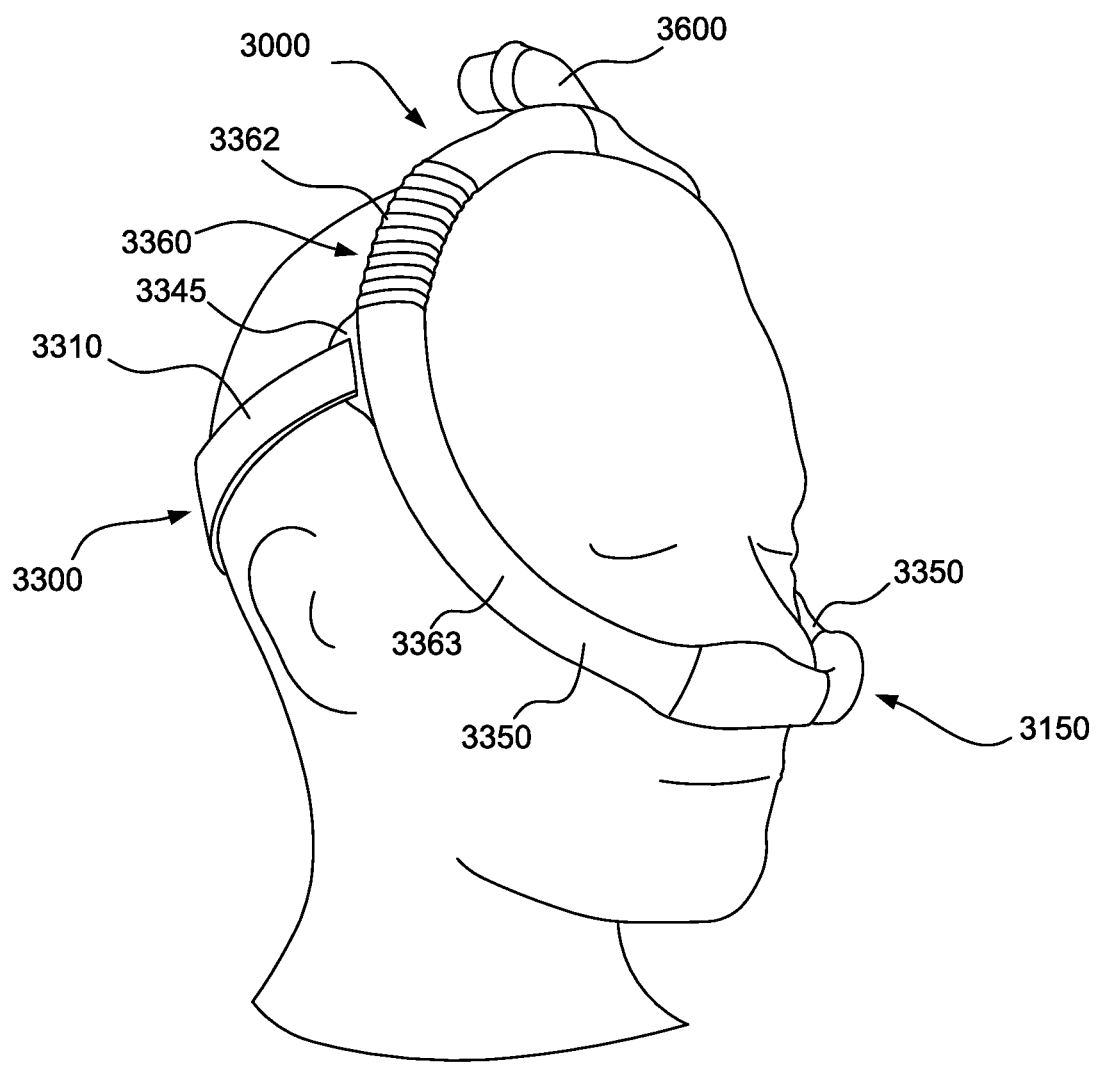
Figure 3B:
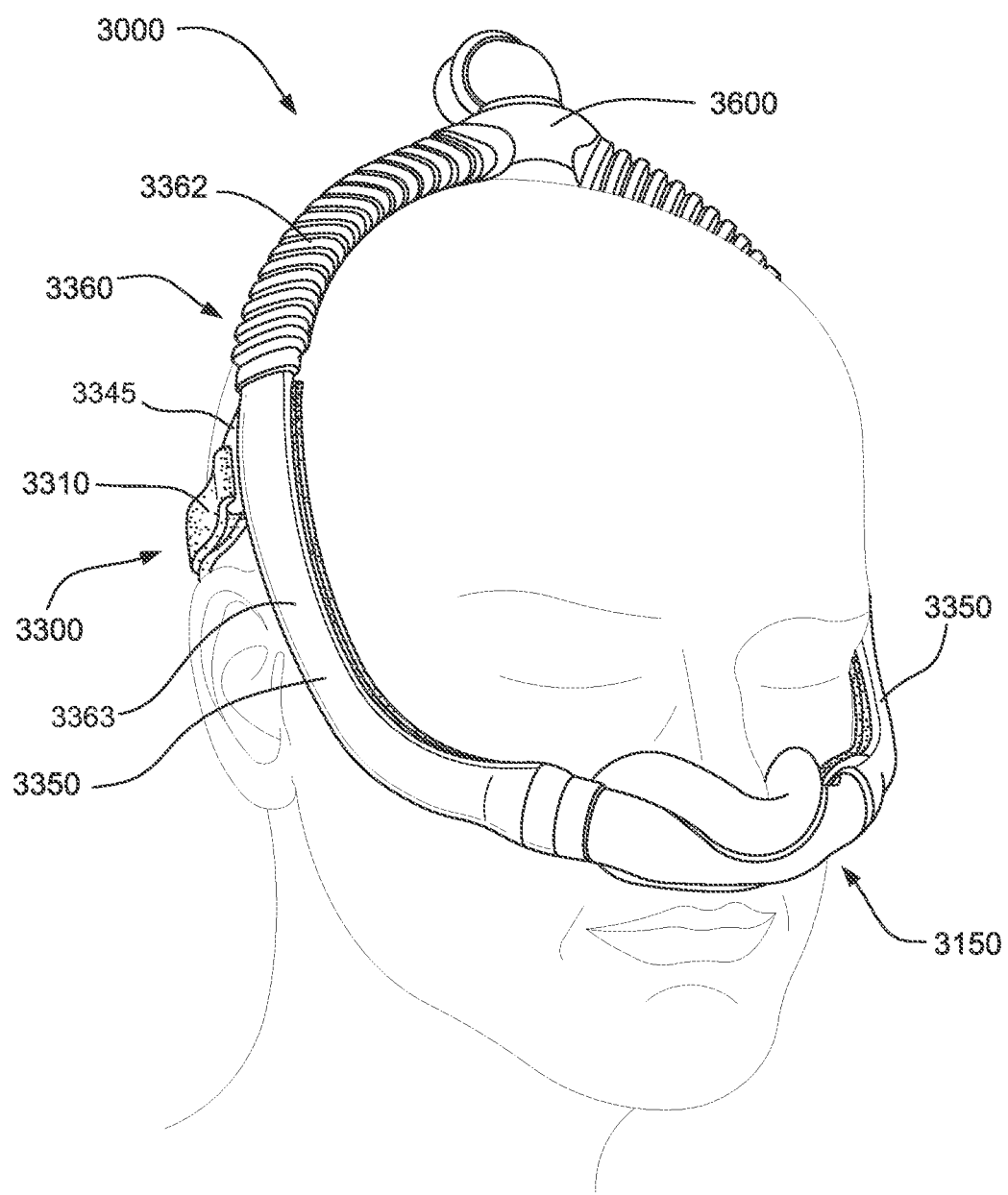
Figure 3C:
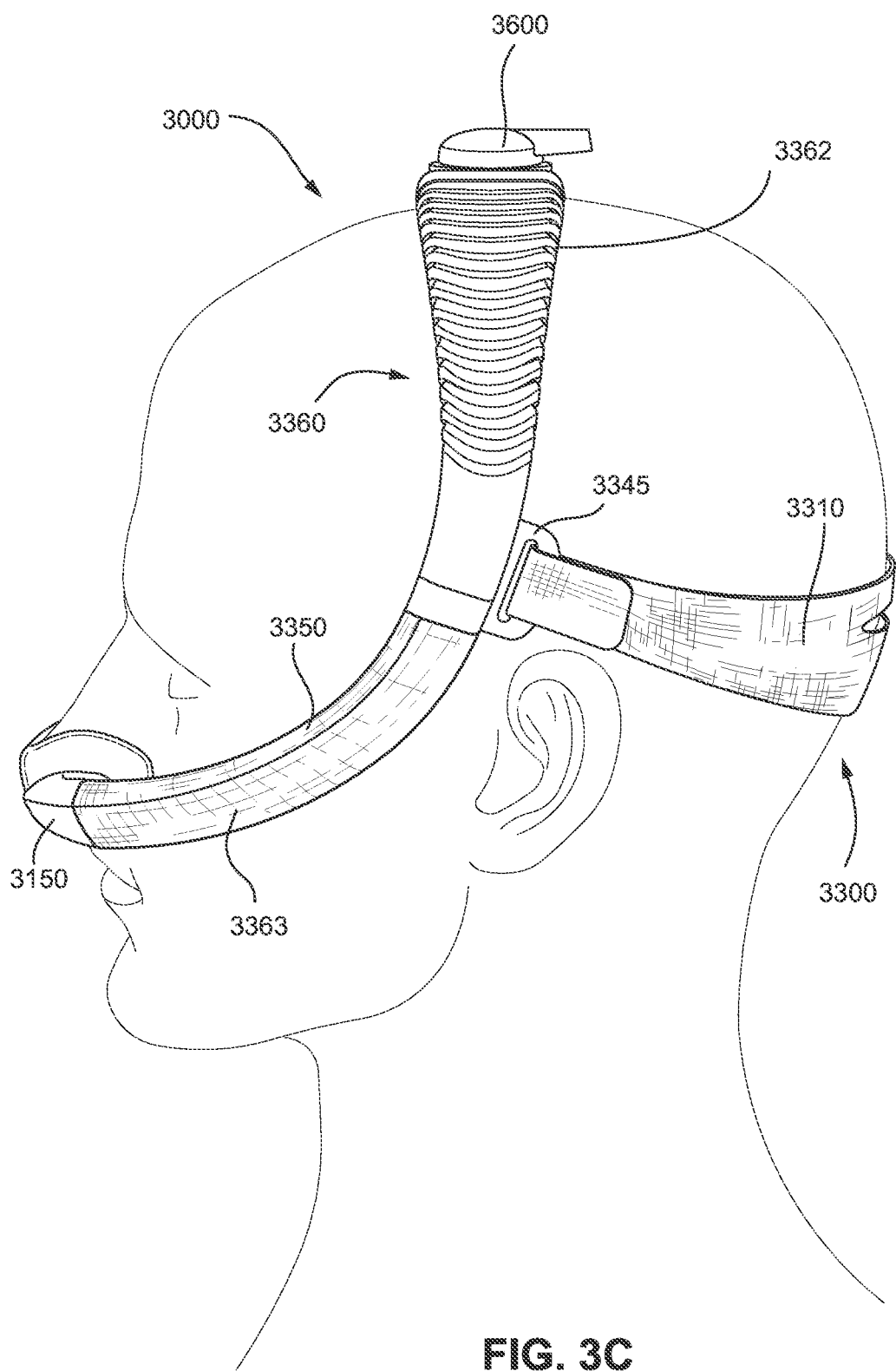
Figure 3D:
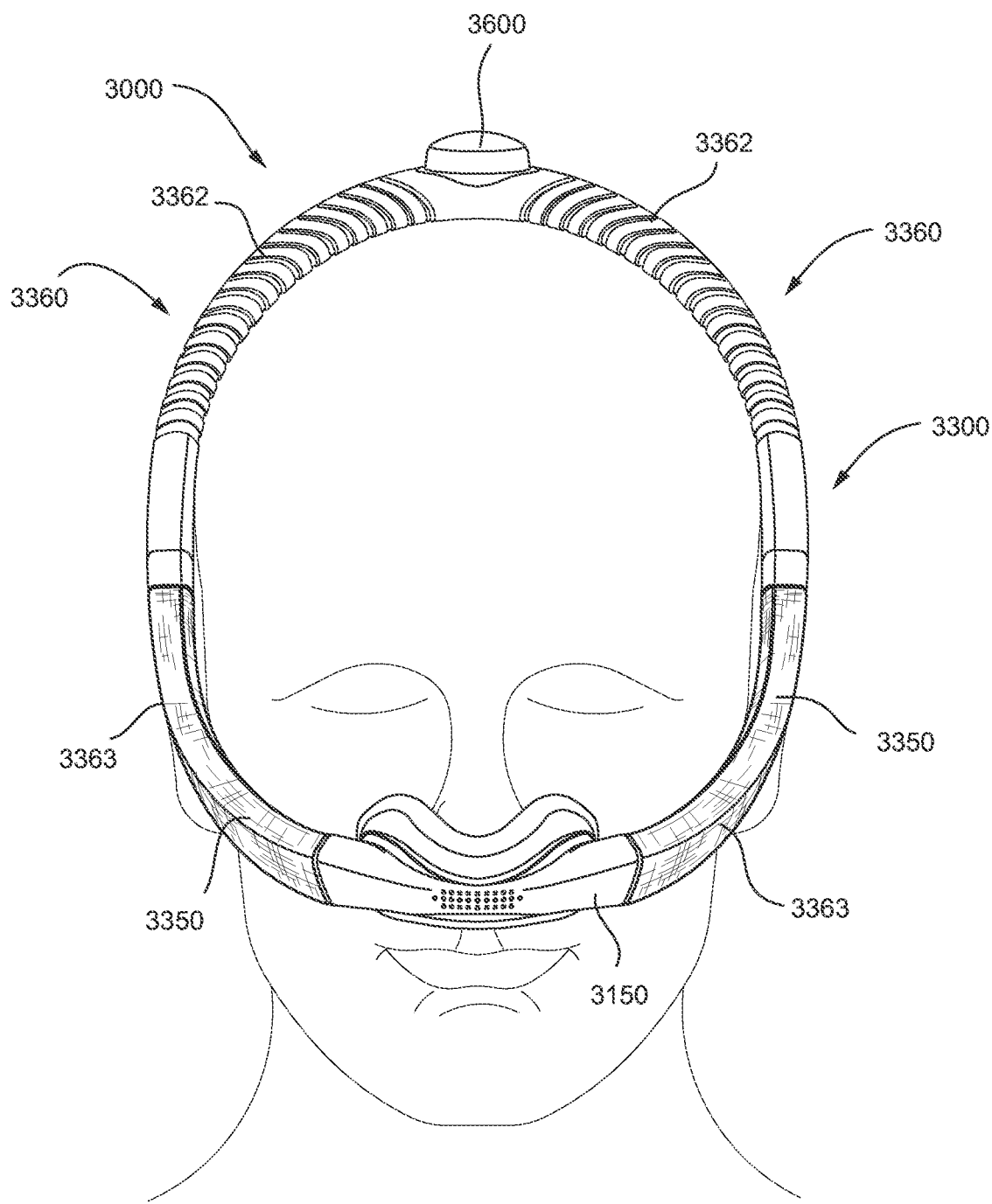
Figure 3E:
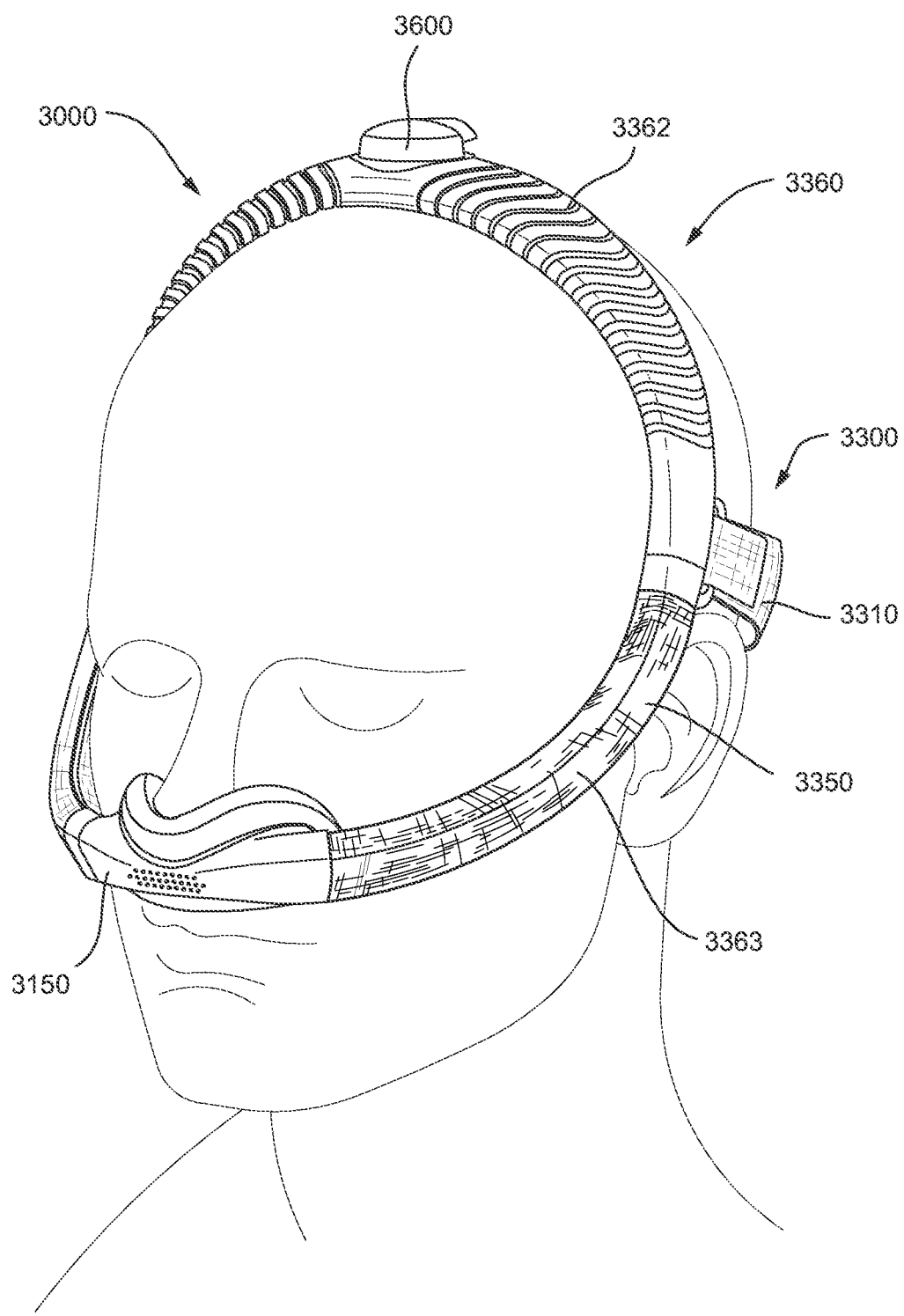

FIG. 3F shows a plan view of the patient interface 3000 shown in FIGS. 3C, 3D and 3E.

FIG. 3G shows in cross-section a portion of the patient interface 3000 shown in FIG. 3F.

Figure 3H:
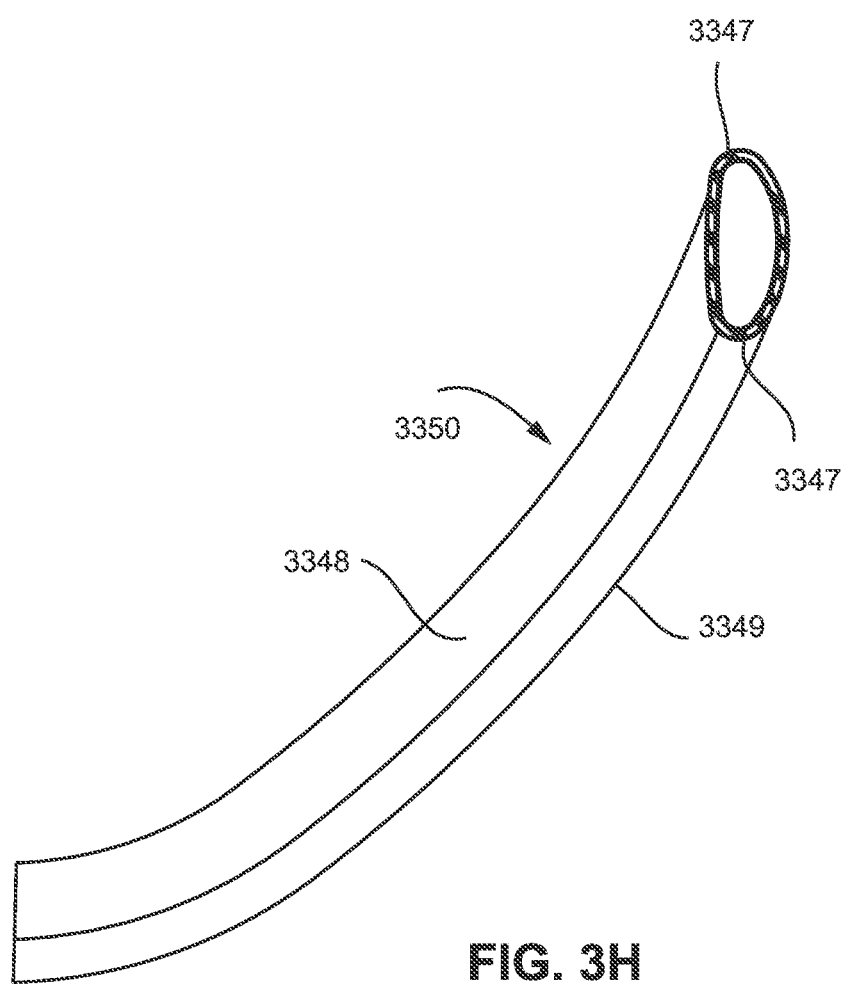

FIG. 3H shows a longitudinal section of a headgear tube 3350 of a patient interface 3000.

Figure 3I:
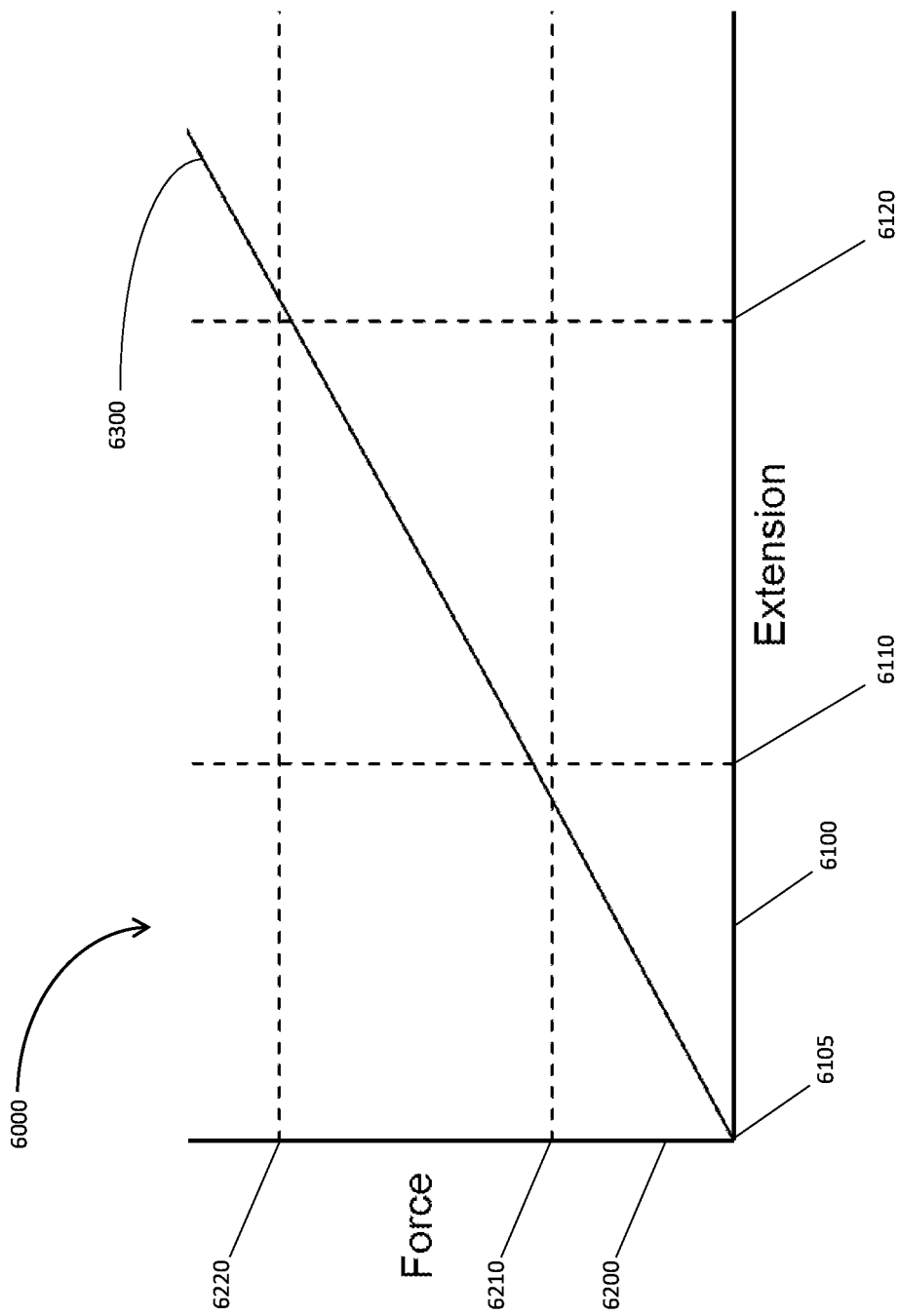

FIG. 3I shows a plot of an exemplary force-extension characteristic of a headgear tube 3350 of a patient interface 3000.

Figure 3J:
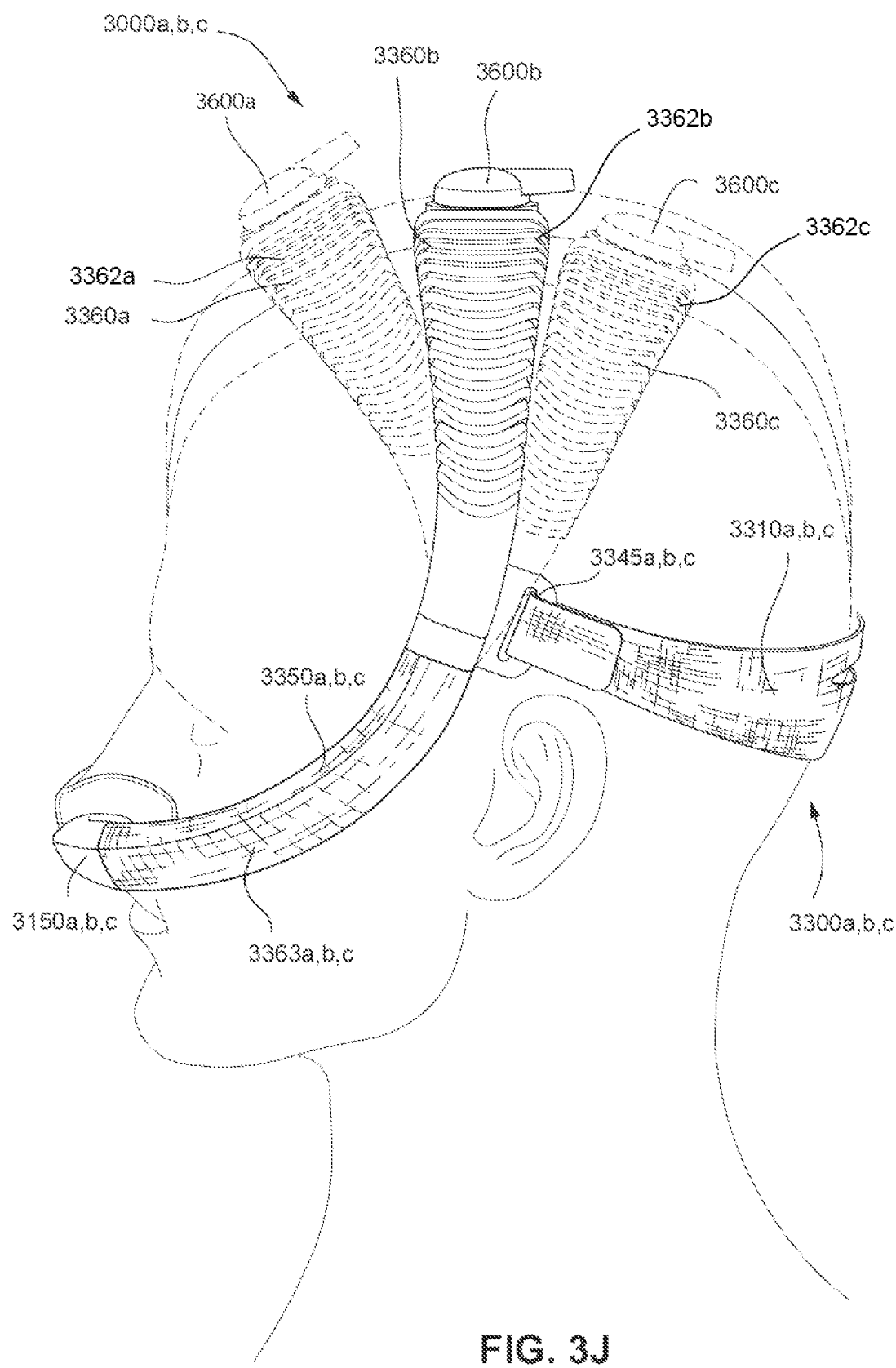

FIG. 3J shows a side view of the patient interface shown in FIGS. 3C, 3D and 3E worn by a patient with a connection port 3600 in a central position and, in phantom, in forward and rearward positions.

Figure 3K:
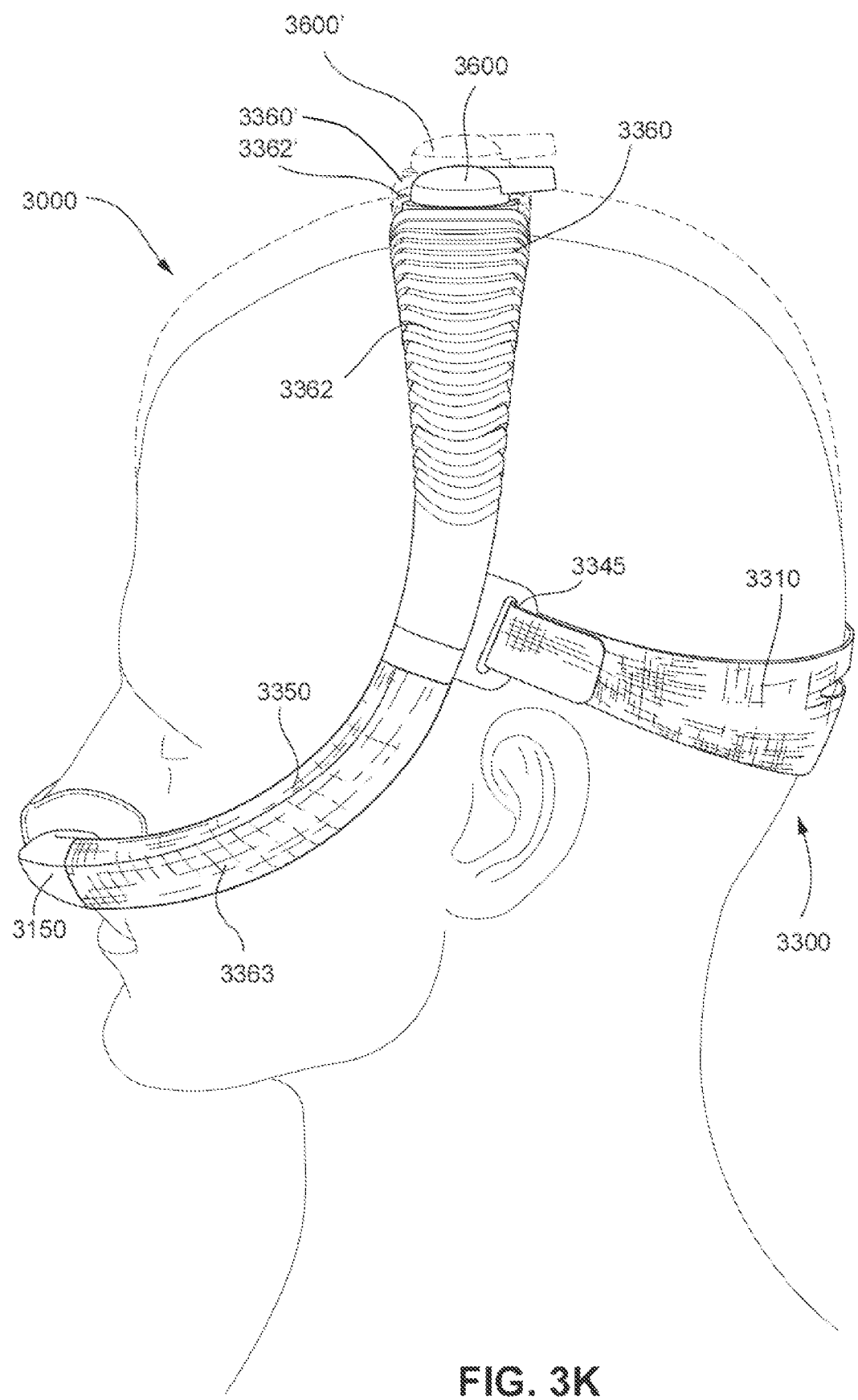

FIG. 3K shows a side view of the patient interface shown in FIGS. 3C, 3D and 3E worn by a patient with one head size and, in phantom, a patient with a larger head size.

Figure 3L:
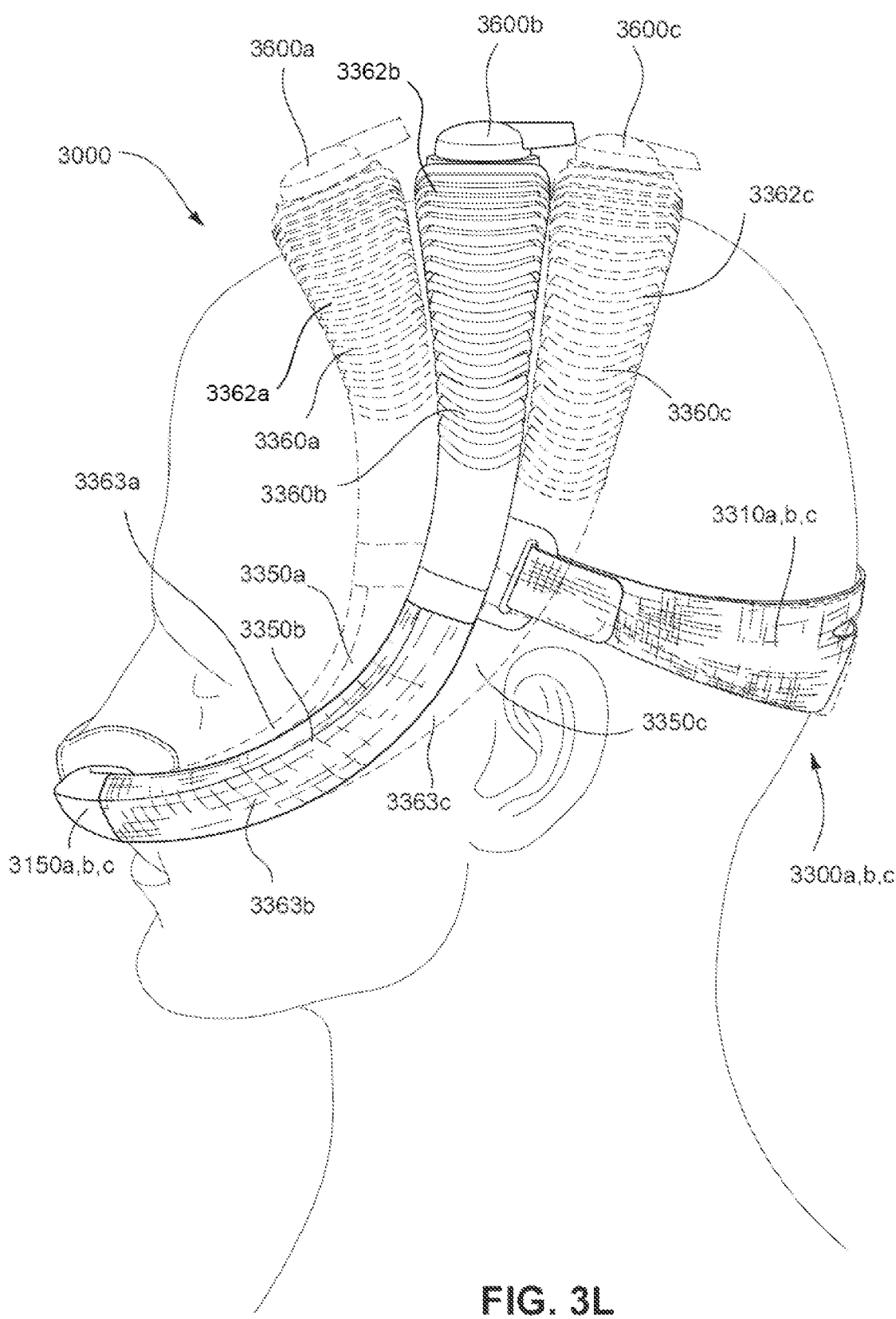

FIG. 3L shows a side view of the patient interface shown in FIGS. 3C, 3D and 3E worn by a patient with an adjustment mechanism 3360 positioned centrally and, in phantom, forwardly and rearwardly.

FIGS. 4A, 4B, 4C, 4D and 4E show cushion assemblies 3150 of a patient interface 3000 according to certain forms of the present technology.

Figure 5:
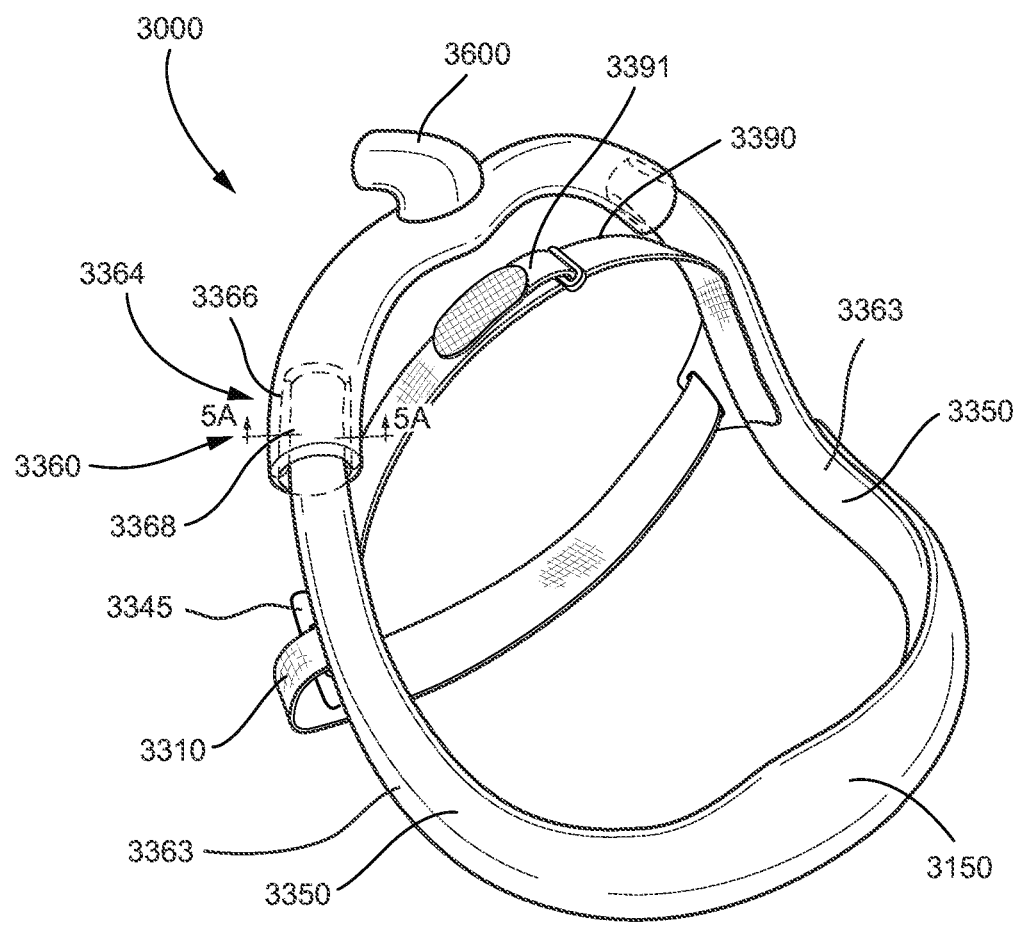

FIG. 5 shows a patient interface 3000 comprising a positioning and stabilising structure 3300 having a fold portion 3364 and a strap 3390 in accordance with one form of the present technology.

Figure 5A:
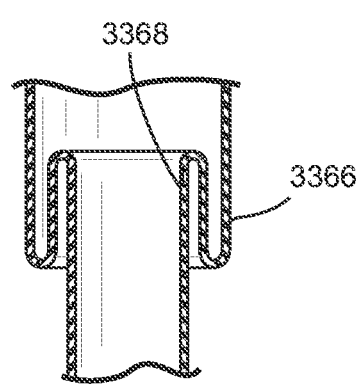
Figure 5B:
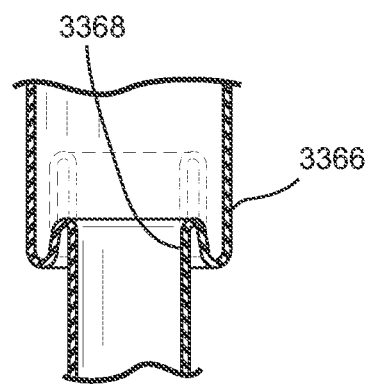

FIGS. 5A and 5B show in cross-section the fold portion 3364 of the patient interface 3000 of FIG. 5 with rolling fold portion 3366 folded over adjacent tube portion 3368 to varying degrees.

Figure 6:
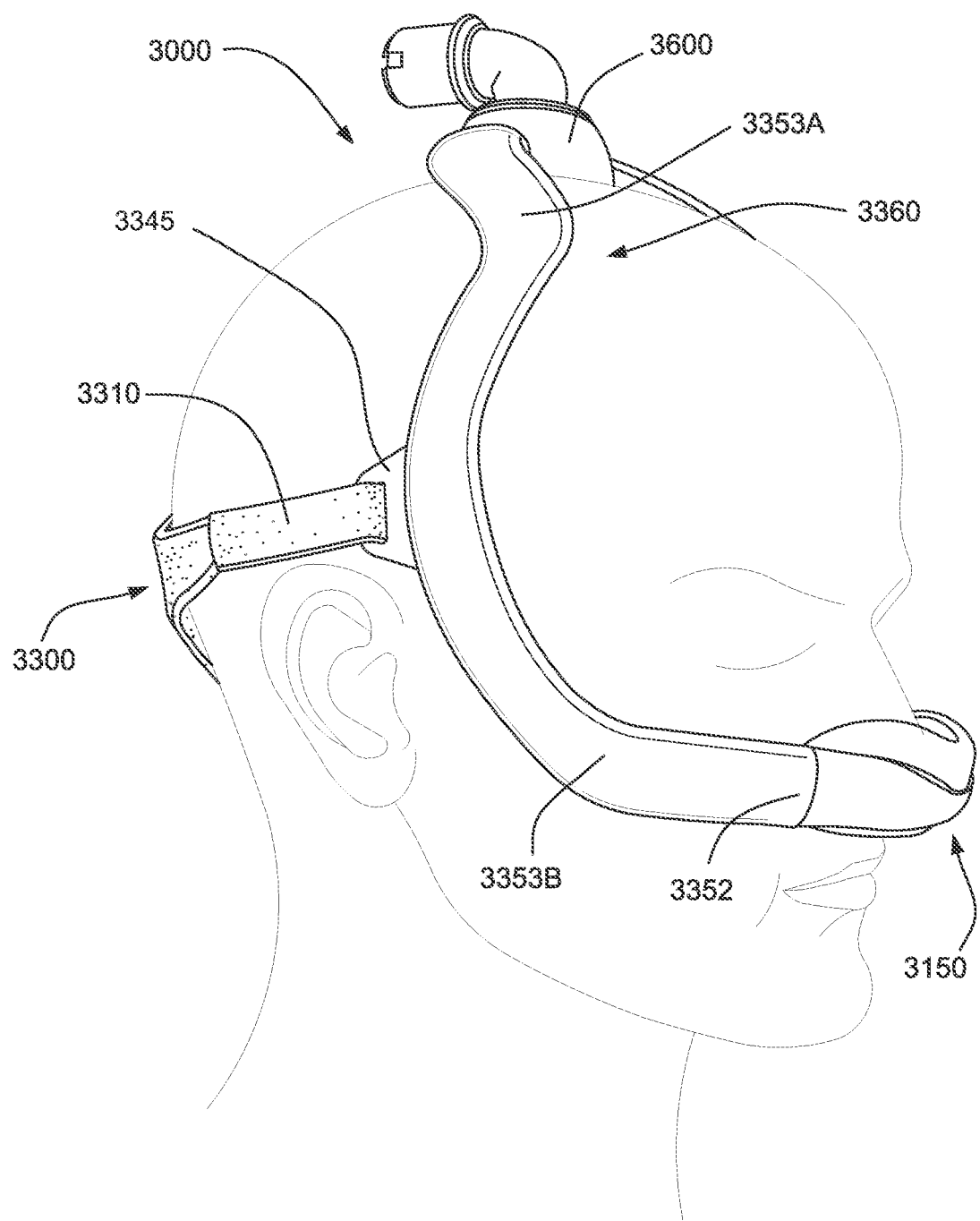

FIG. 6 shows a patient interface 3000 comprising a positioning and stabilising structure 3300 comprising flexible tubes 3350 in accordance with one form of the present technology.

Figure 7A:
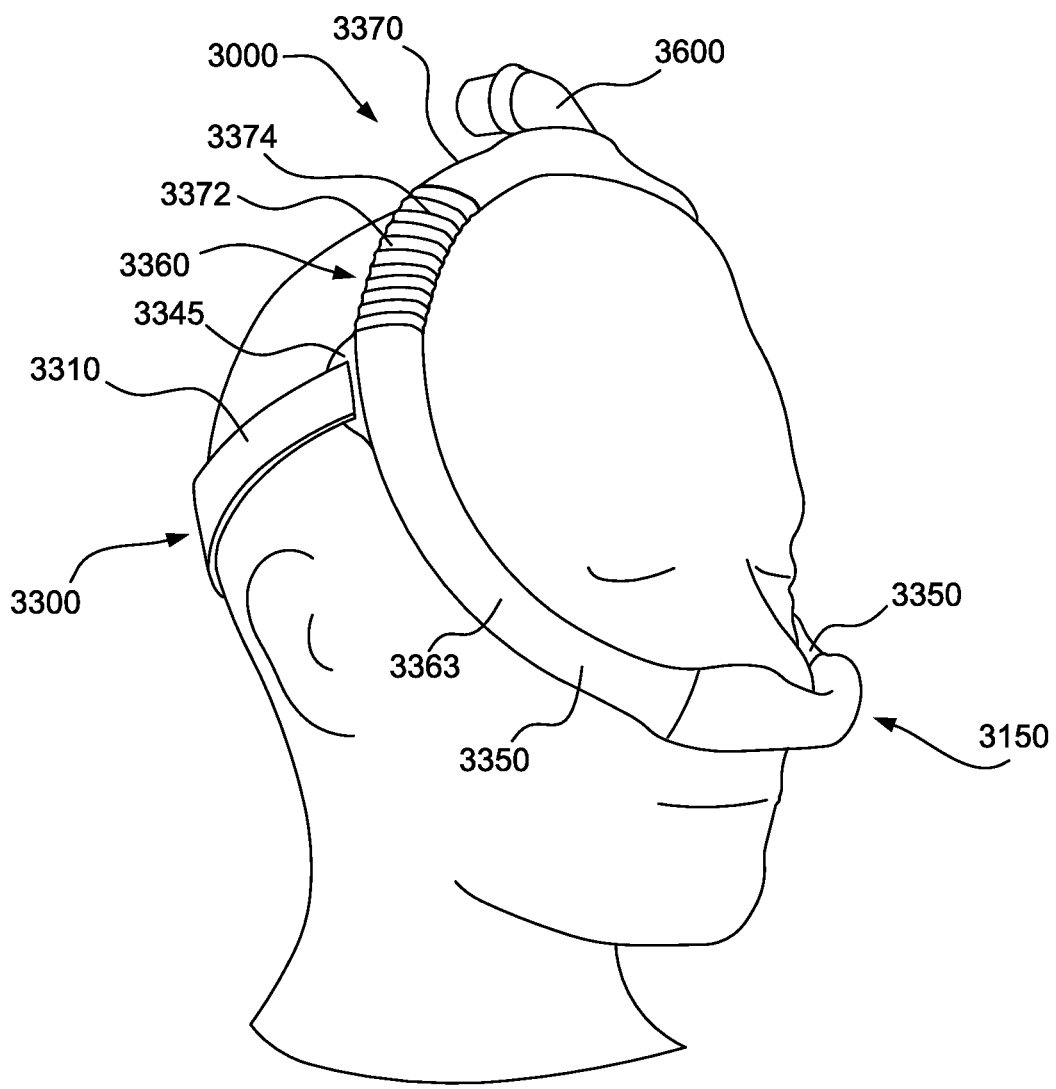
Figure 7B:
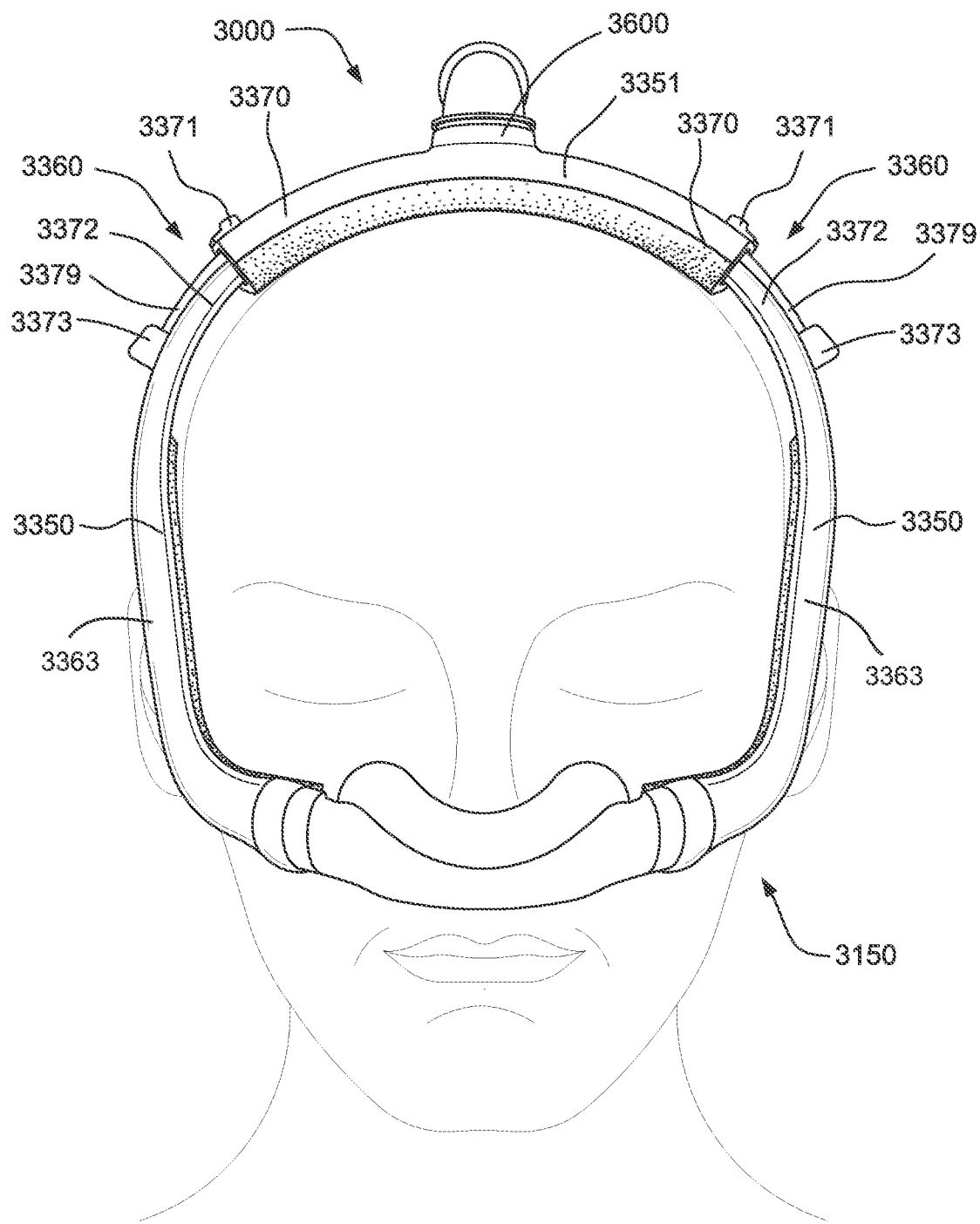
Figure 7C:
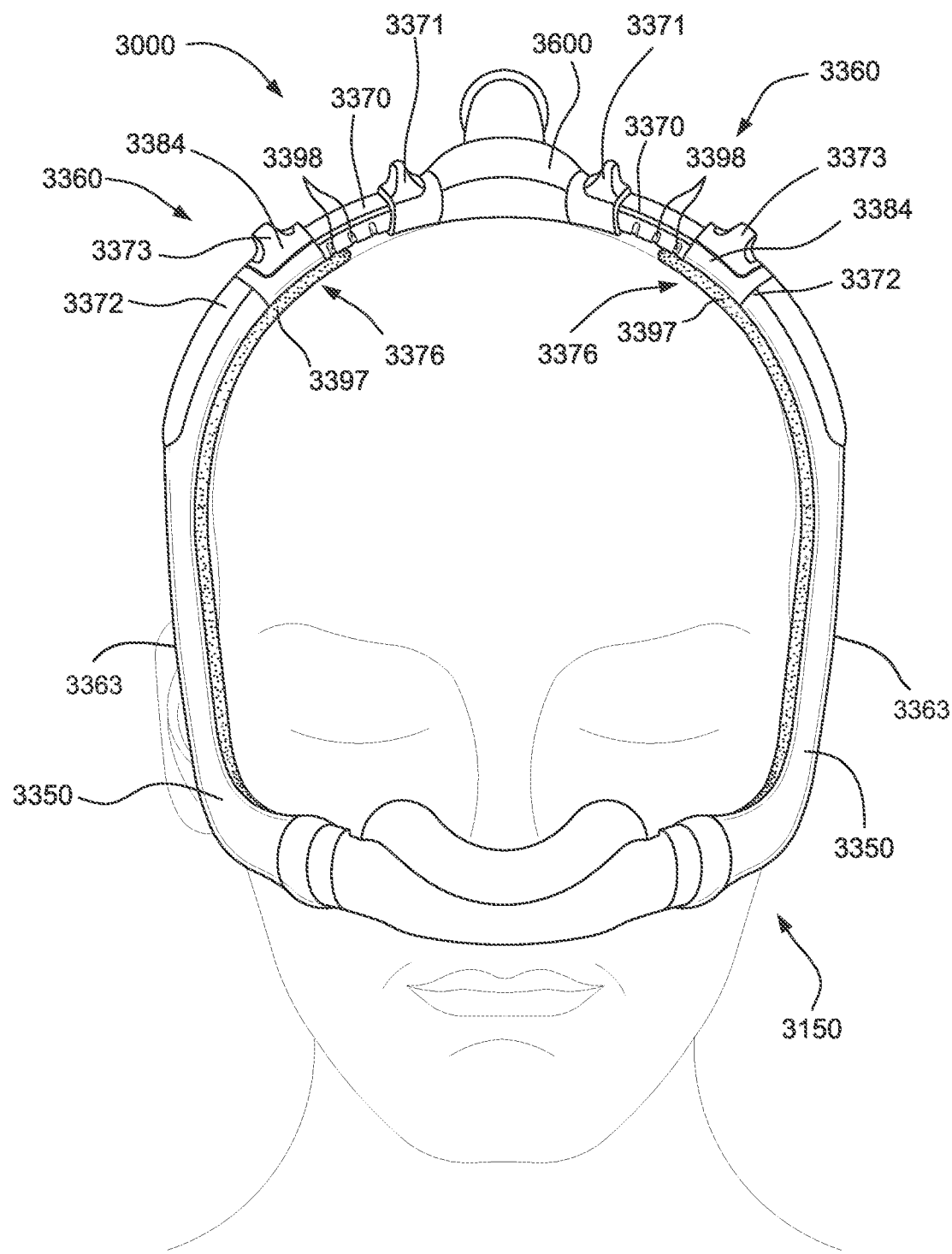

FIGS. 7A, 7B and 7C show patient interfaces 3000 comprising a positioning and stabilising structure 3300 having first and second tube portions 3370 and 3372 in accordance with certain forms of the present technology.

Figure 8:
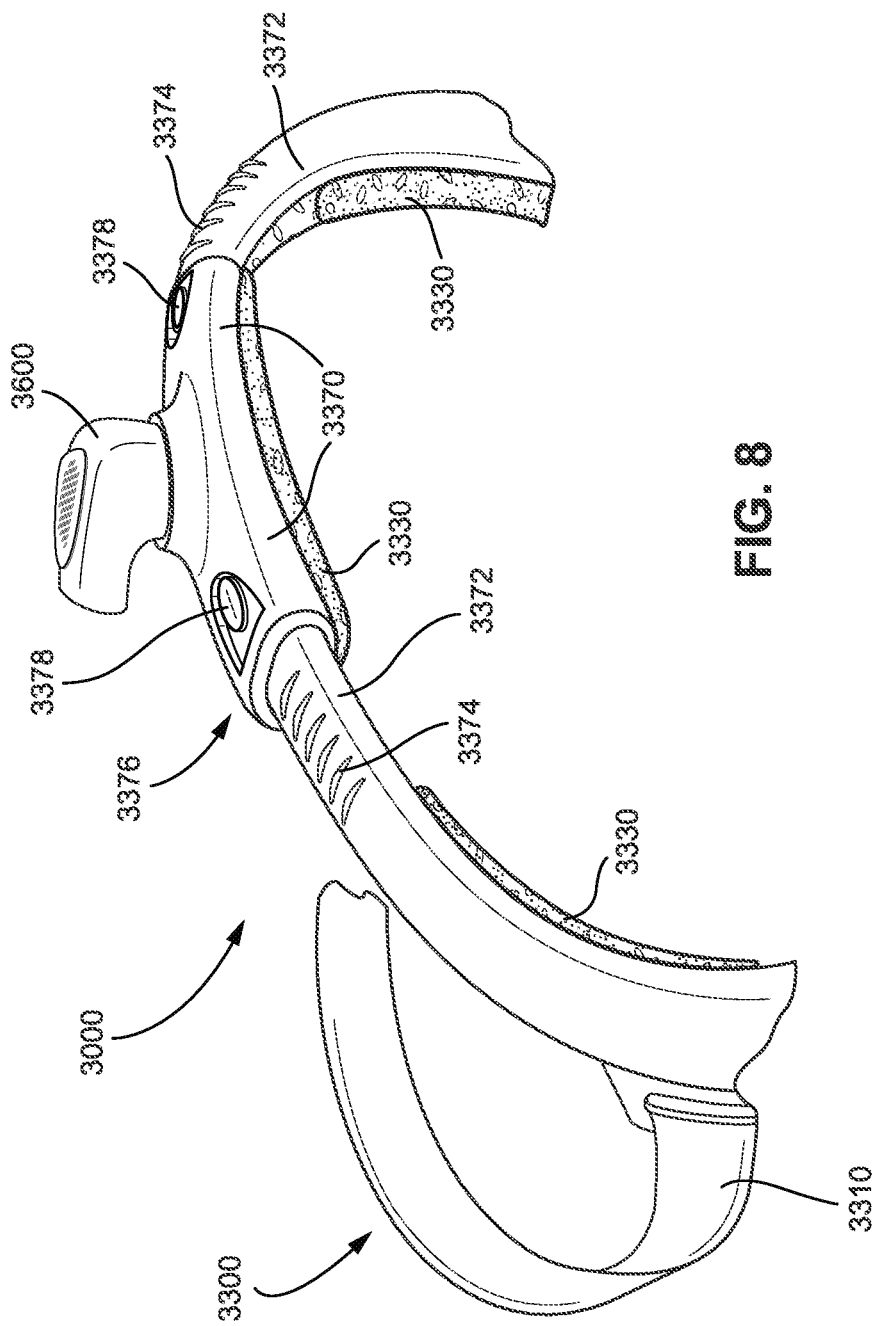

FIG. 8 shows part of a patient interface 3000 comprising a positioning and stabilising structure 3300 having discretely adjustable first and second tube portions 3370 and 3372 in accordance with one form of the present technology.

Figure 9:
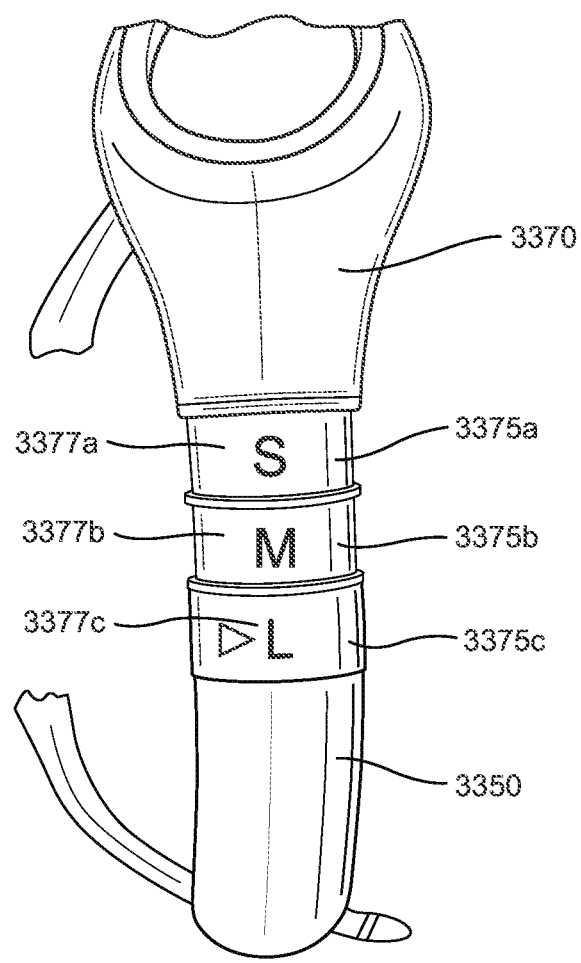

FIG. 9 shows part of a patient interface comprising a positioning and stabilising structure 3300 having first and second tube portions 3370 and 3372 in accordance with one form of the present technology.

Figure 10A:
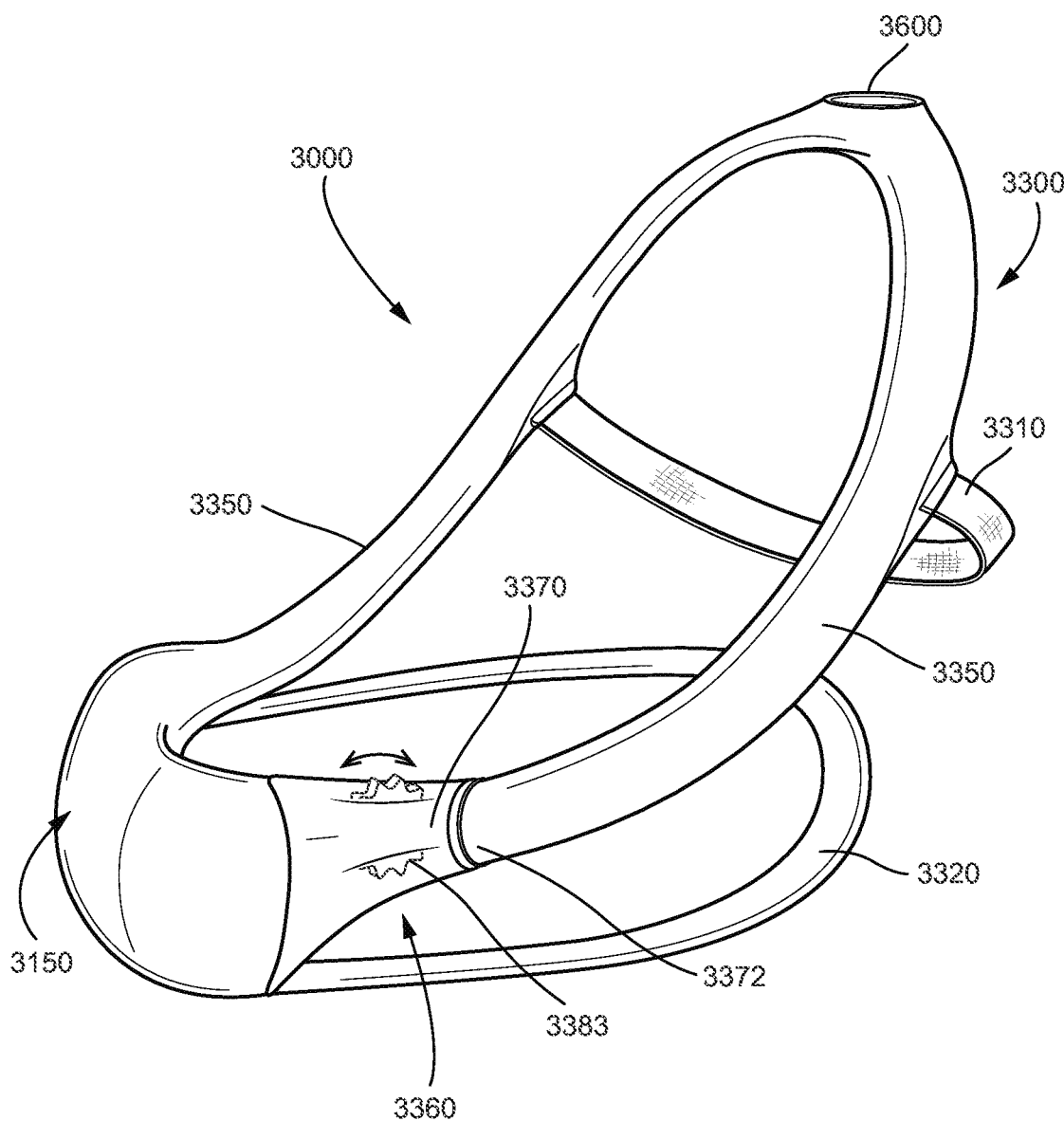

FIG. 10A shows a patient interface 3000 comprising a positioning and stabilising structure 3300 having an adjustment mechanism 3360 in accordance with one form of the present technology.

Figure 10B:
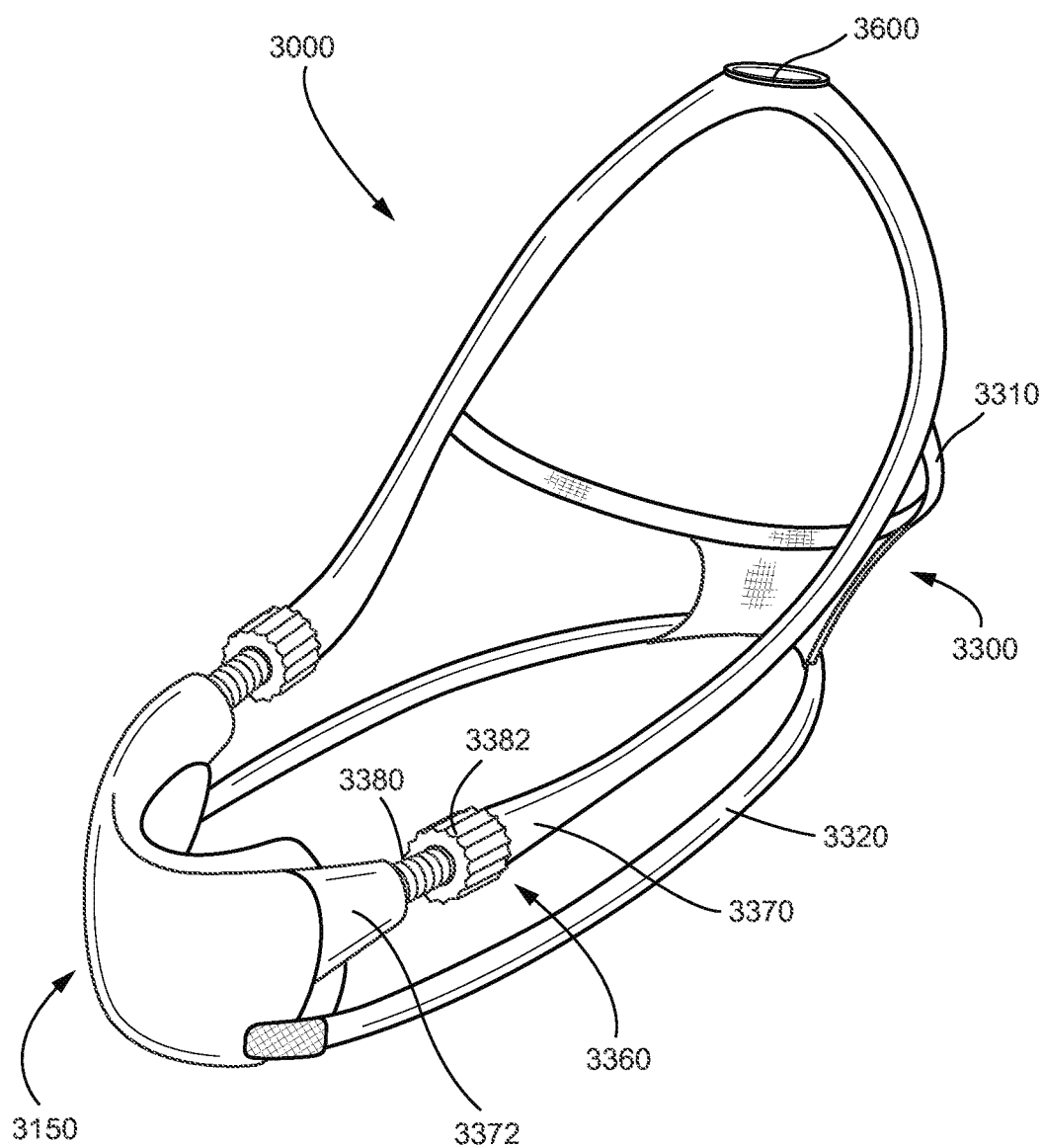
Figure 11:
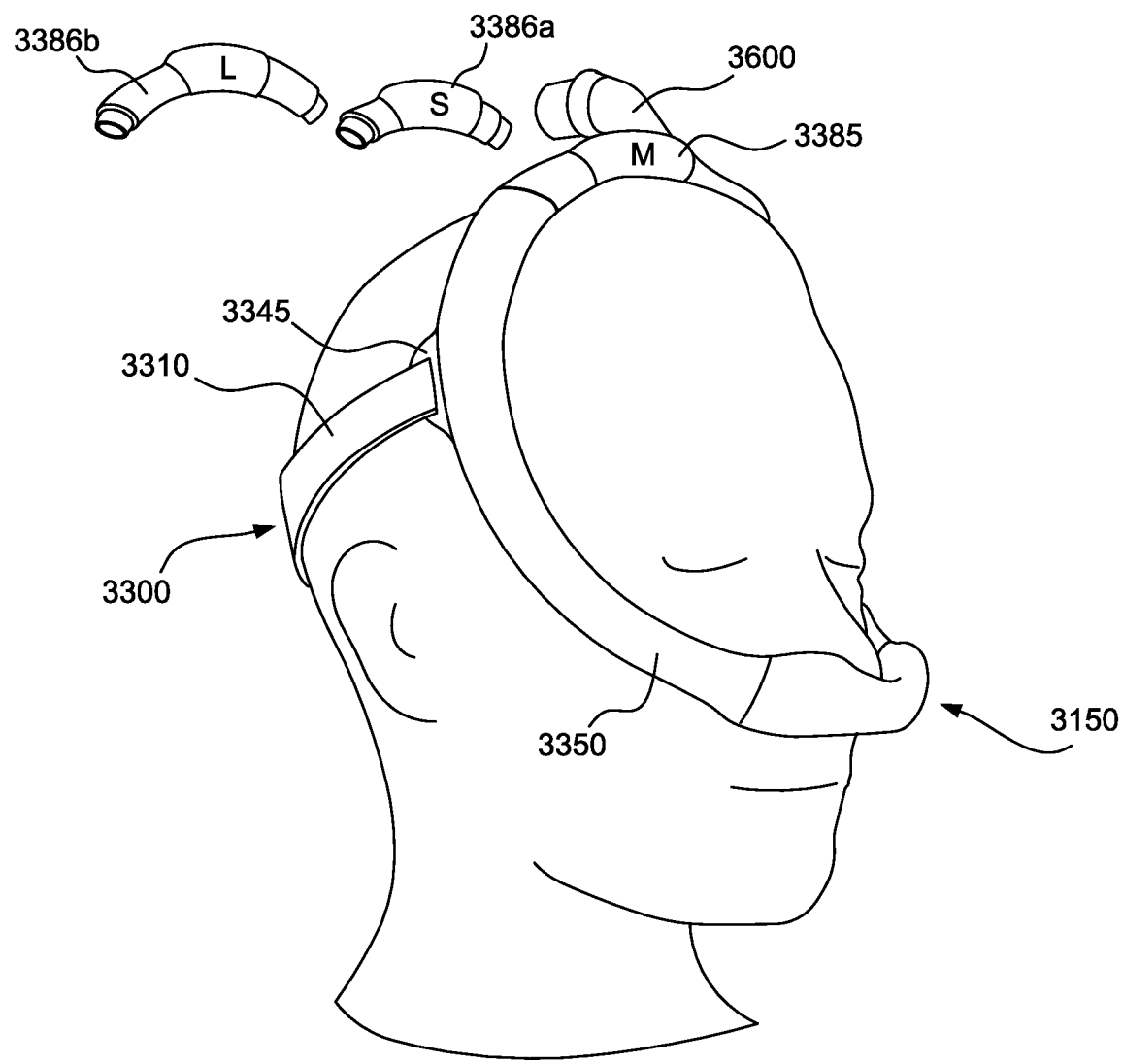

FIG. 10B shows a patient interface 3000 comprising a positioning and stabilising structure 3300 having threaded tube sections 3380 and 3382 in accordance with one form of the present technology FIG. 11 shows a patient interface 3000 comprising a positioning and stabilising structure 3300 having replaceable tube portions 3385 and 3386 in accordance with one form of the present technology.

Figure 12:
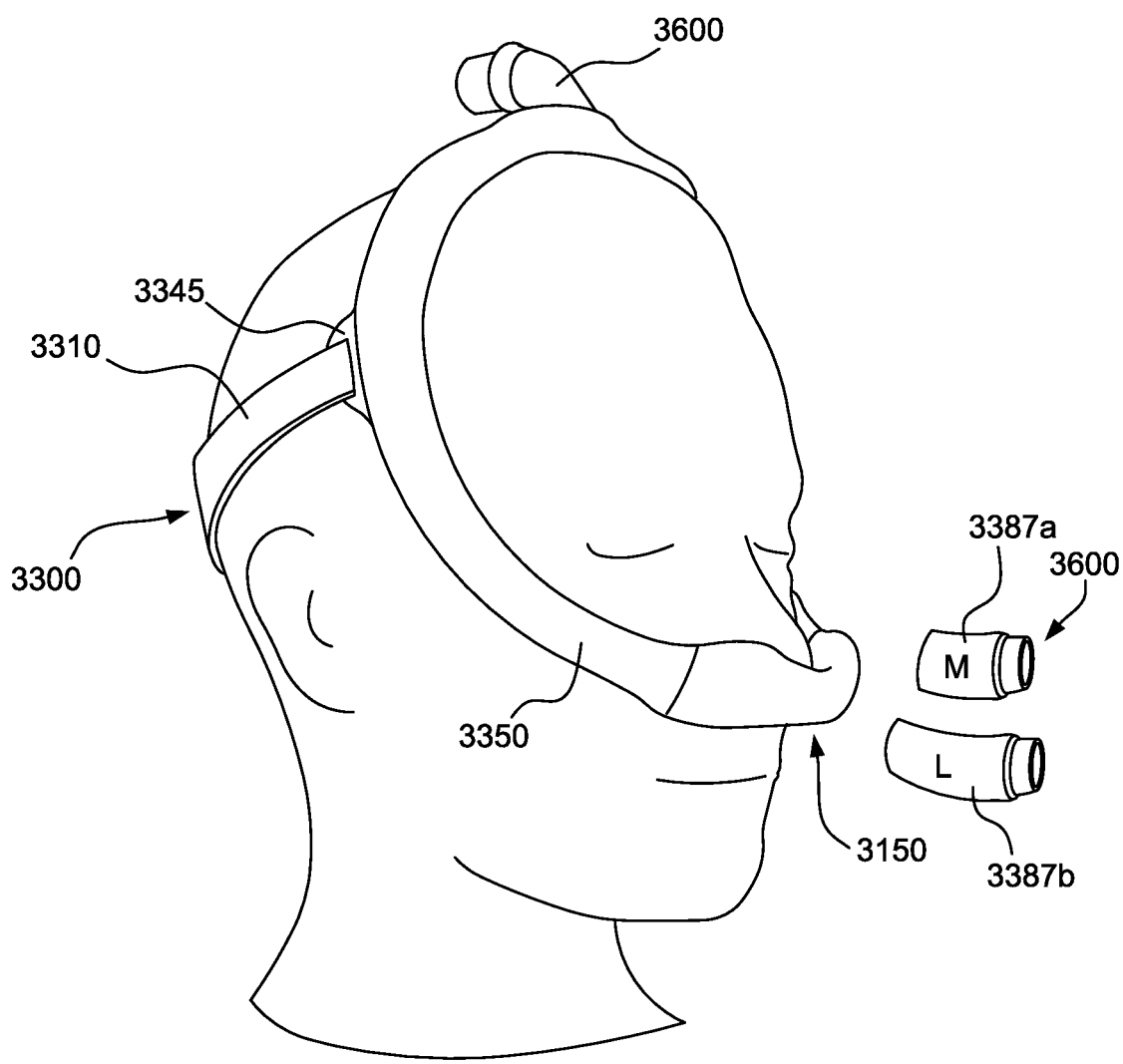

FIG. 12 shows a patient interface 3000 comprising a positioning and stabilising structure 3300 having insertable tube portions 3387 in accordance with one form of the present technology.

Figure 13:
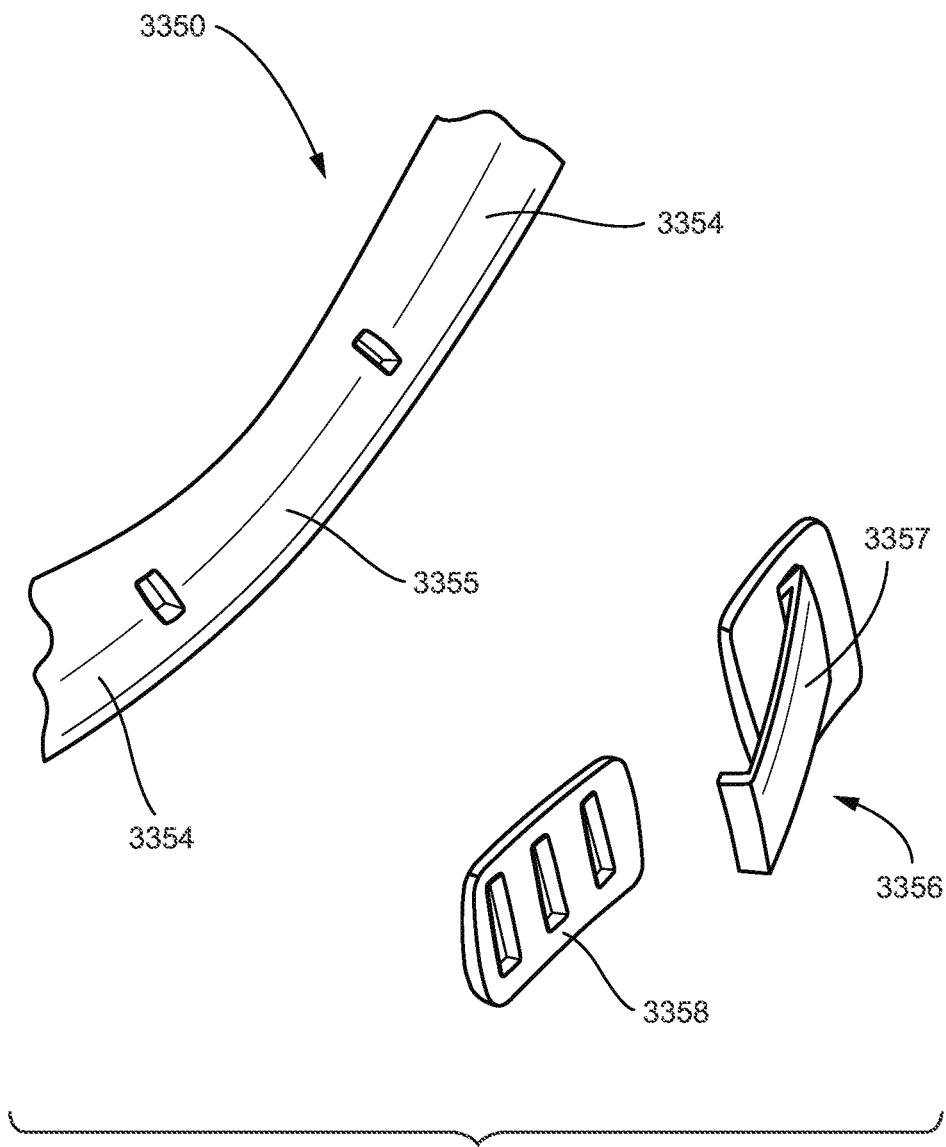

FIG. 13 shows part of a tube 3350 for a patient interface comprising a stretchable tube section 3355 in accordance with one form of the present technology.

Figure 14:
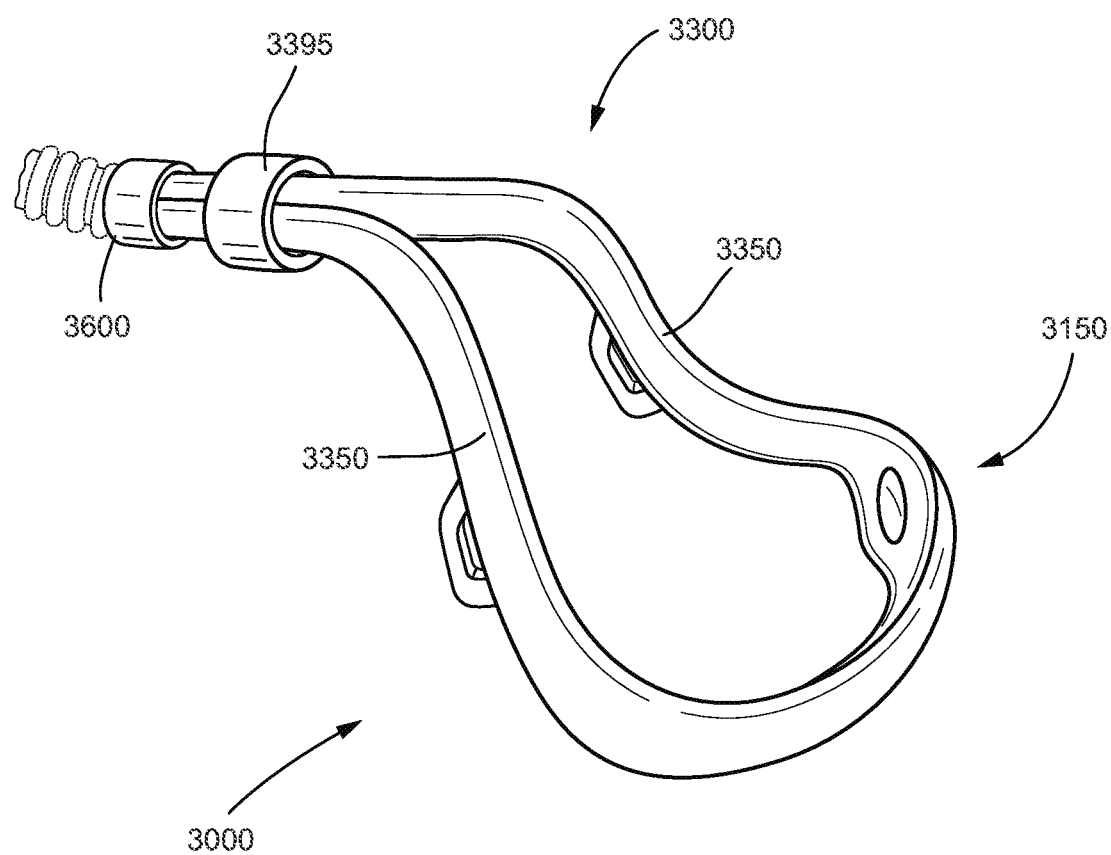

FIG. 14 shows a patient interface 3000 comprising a positioning and stabilising structure 3300 having band 3395 in accordance with one form of the present technology.

Figure 15:
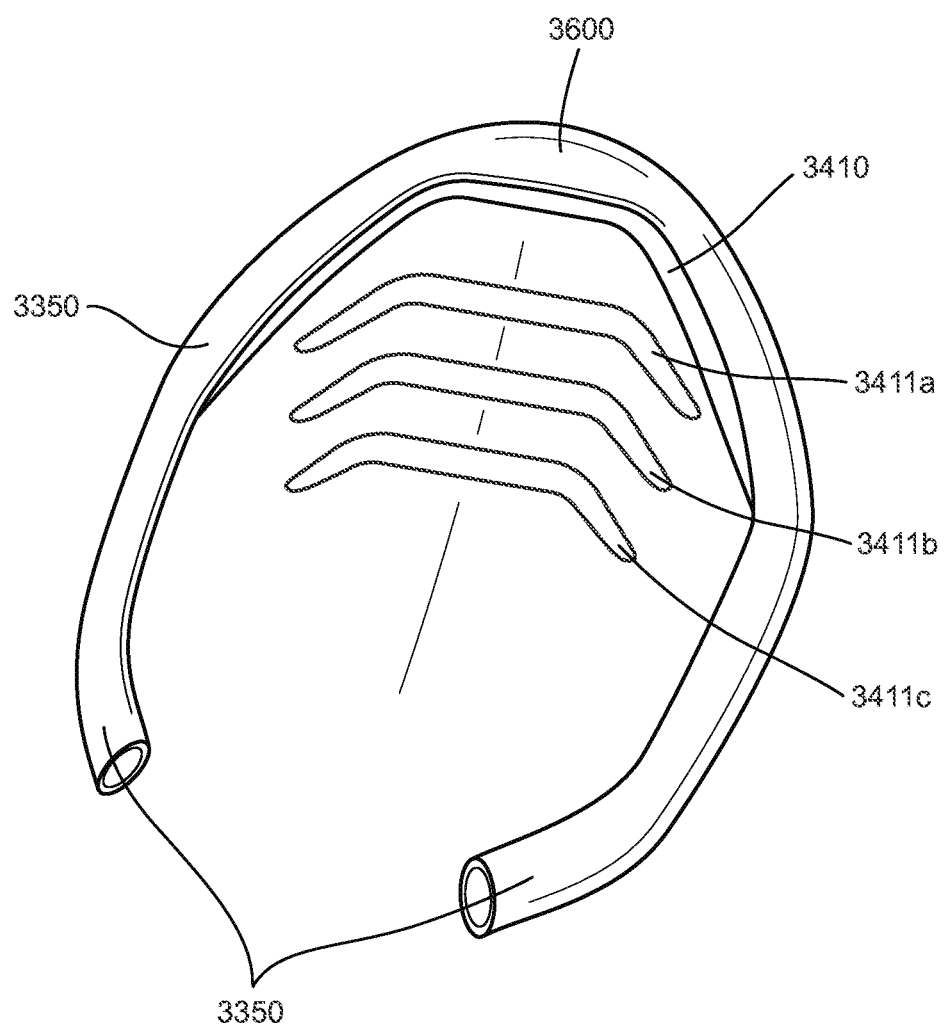

FIG. 15 shows a part of a patient interface comprising replaceable loop insert members 3410 and 3411 in accordance with one form of the present technology.

Figure 16:
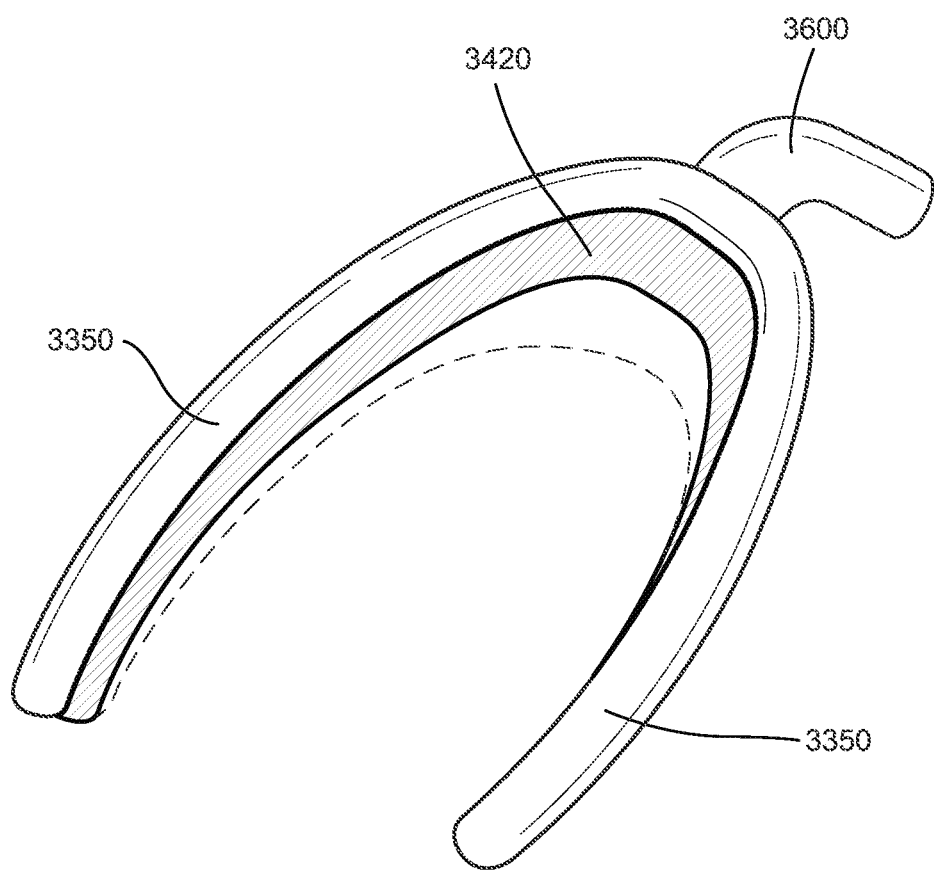

FIG. 16 shows a part of a patient interface comprising an inflatable loop insert member 3420 in accordance with one form of the present technology.

Figure 17:
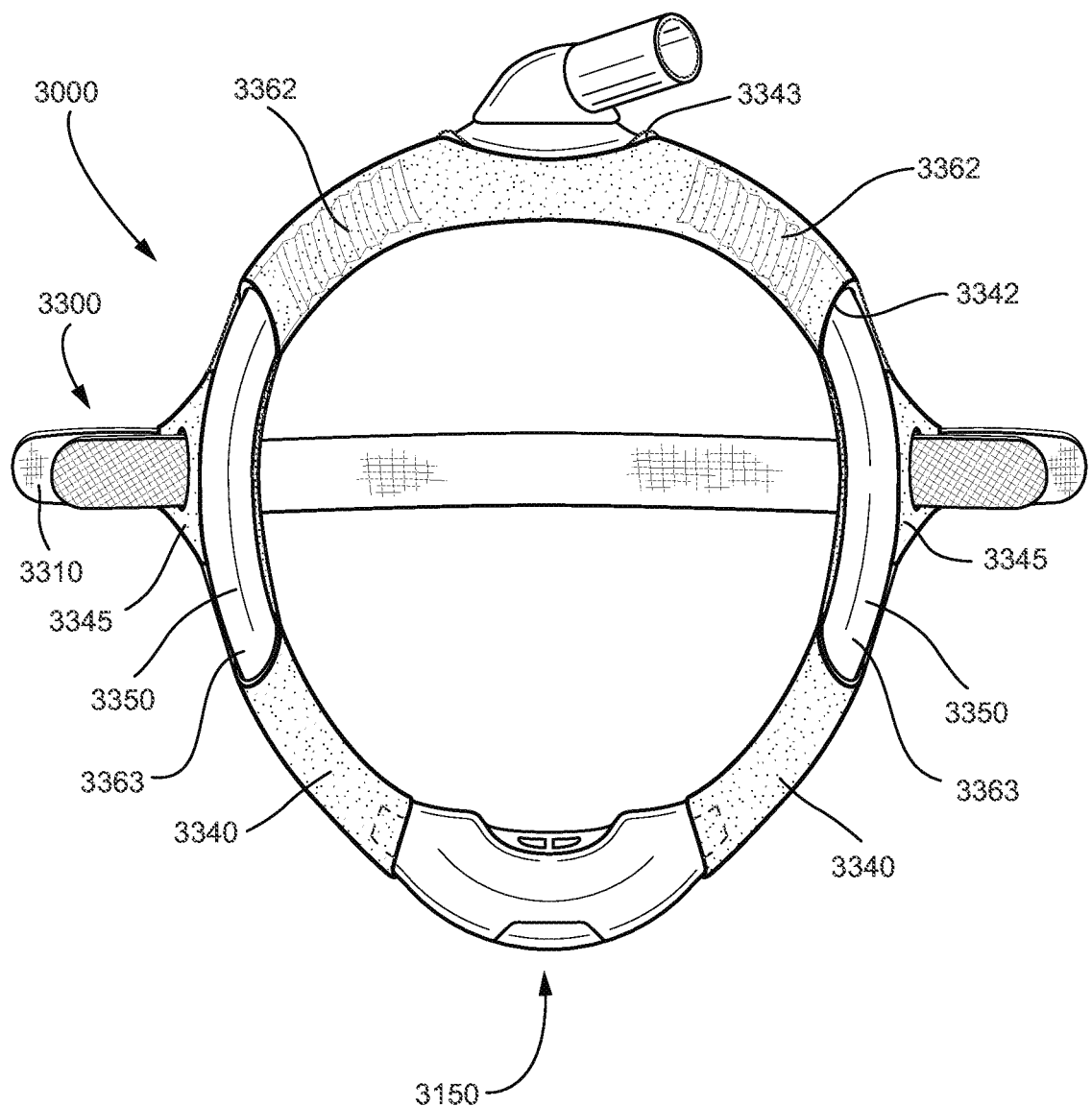

FIG. 17 shows a patient interface 3000 comprising a positioning and stabilising structure 3300 having concertina tube sections 3362 and an elastic sleeve 3340 in accordance with one form of the present technology.

7.4 RPT Device

Figure 18:
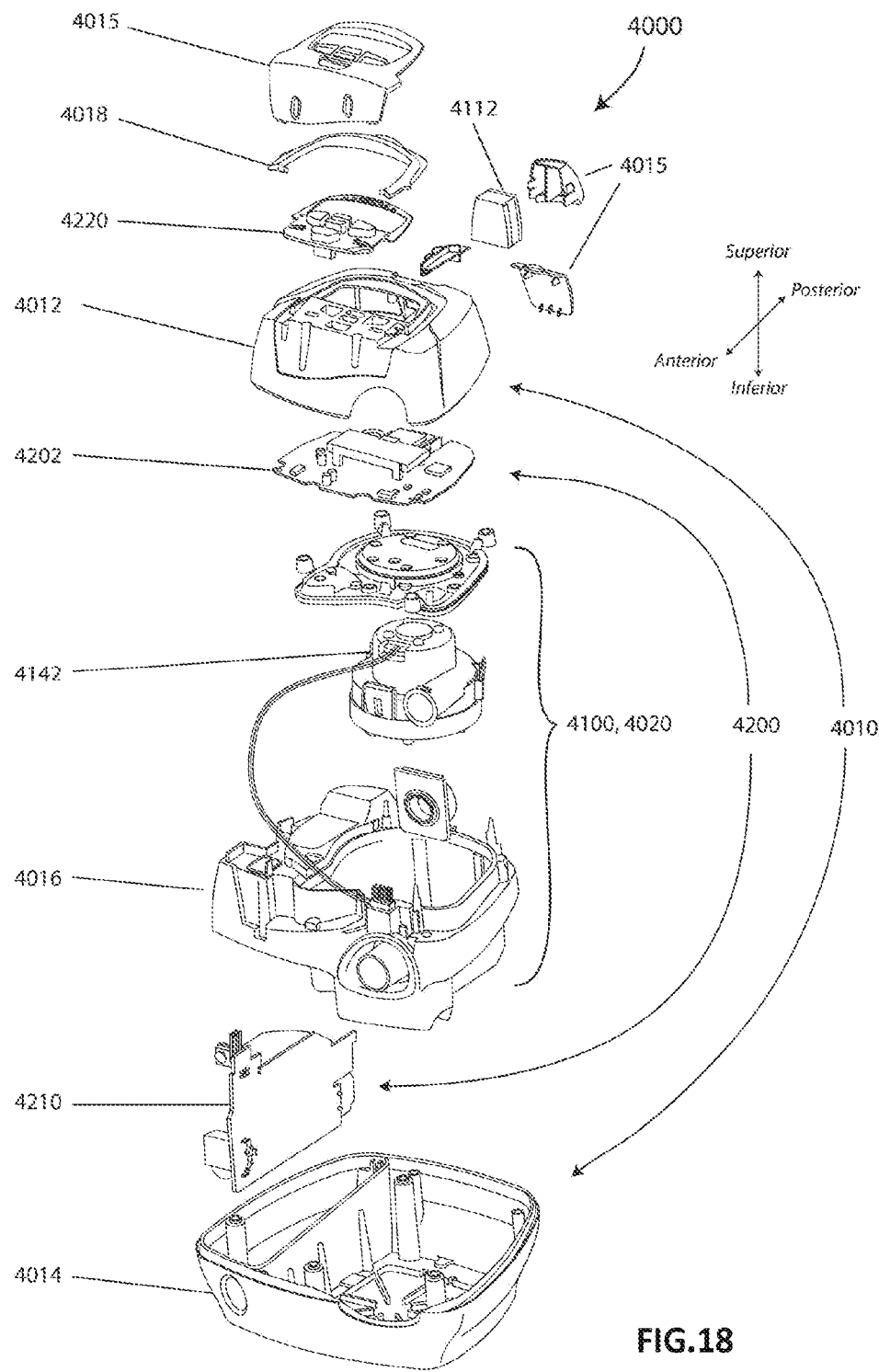

FIG. 18 shows an RPT device in accordance with one form of the present technology.

7.5 Humidifier

Figure 19A:
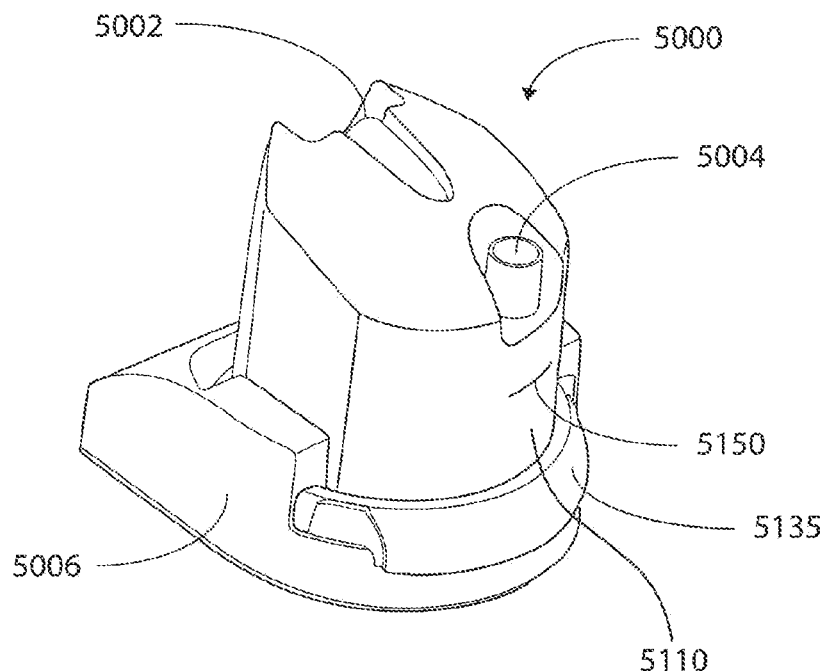

FIG. 19A shows an isometric view of a humidifier in accordance with one form of the present technology.

Figure 19B:
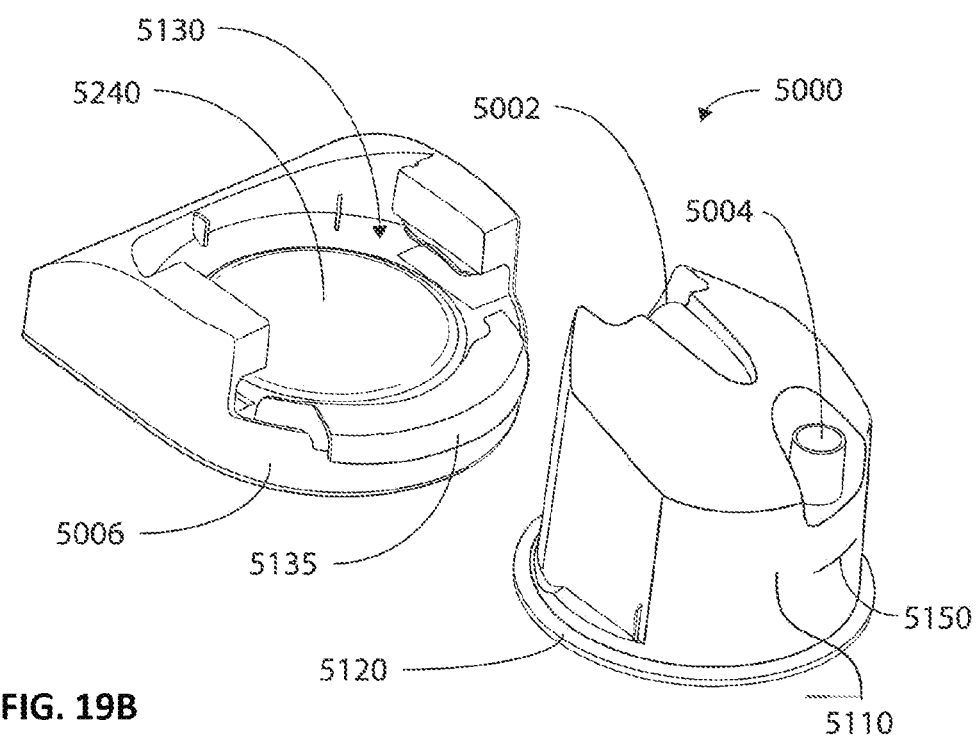

FIG. 19B shows an isometric view of a humidifier in accordance with one form of the present technology, showing a humidifier reservoir 5110 removed from the humidifier reservoir dock 5130.

7.6 Insert Member

Figure 20A:
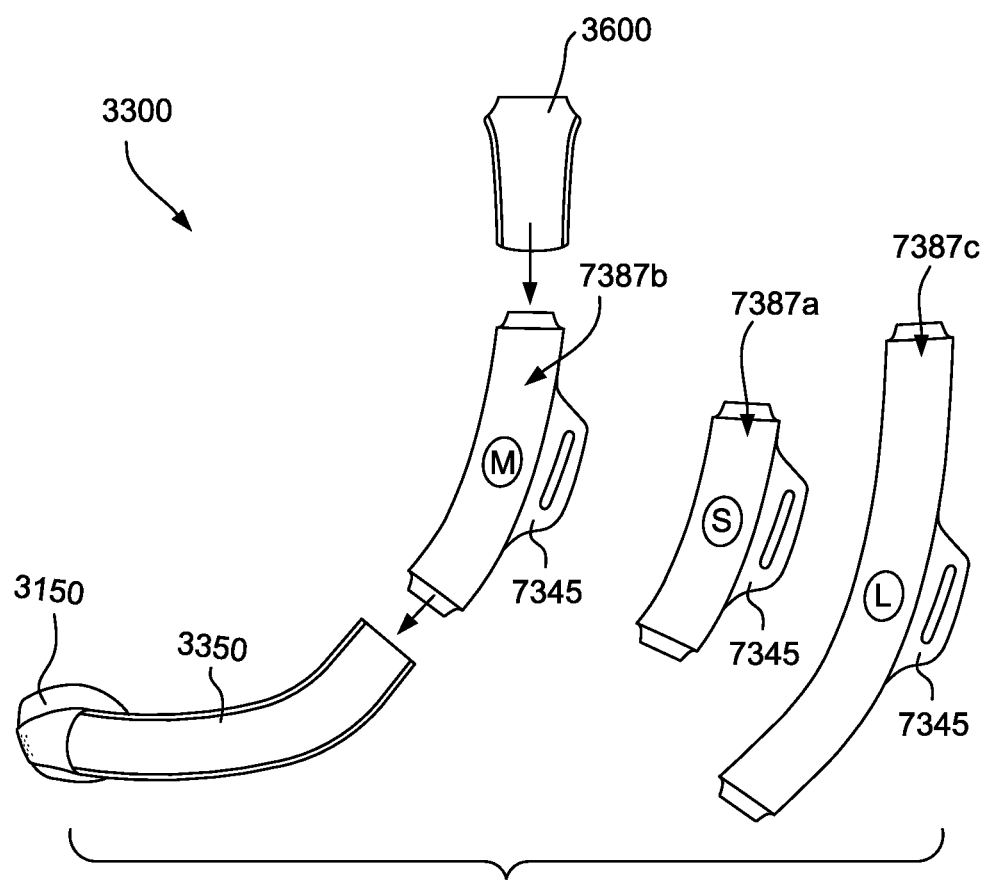
Figure 20B:
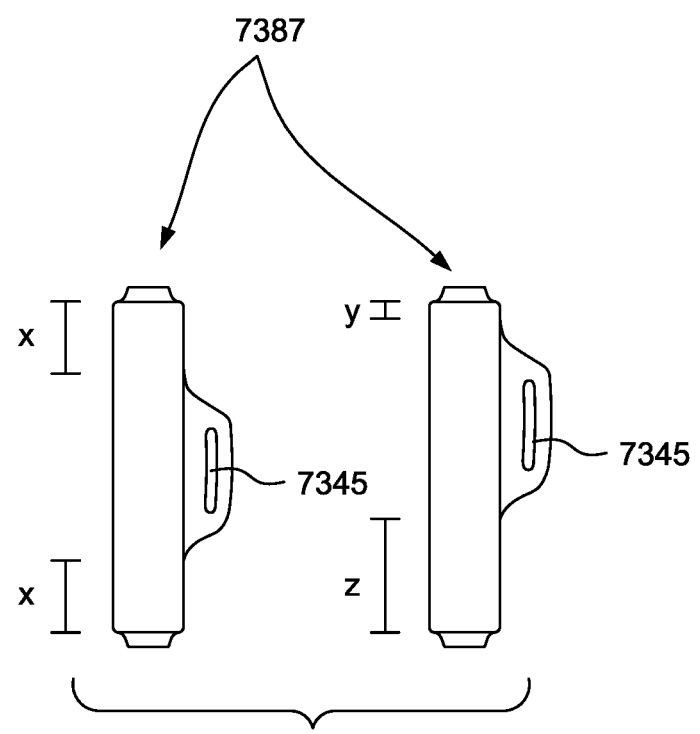

FIGS. 20A and 20B shows a positioning and stabilising structure 3300 comprising having tube insert members 7387 in accordance with one form of the present technology.

Figure 27A:
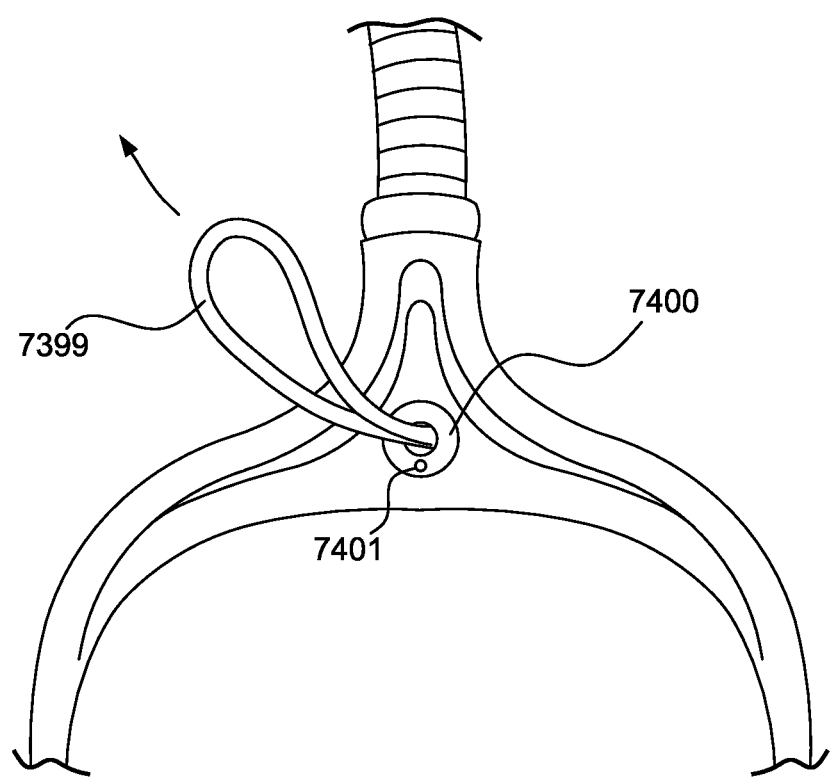
Figures 1, 27B:
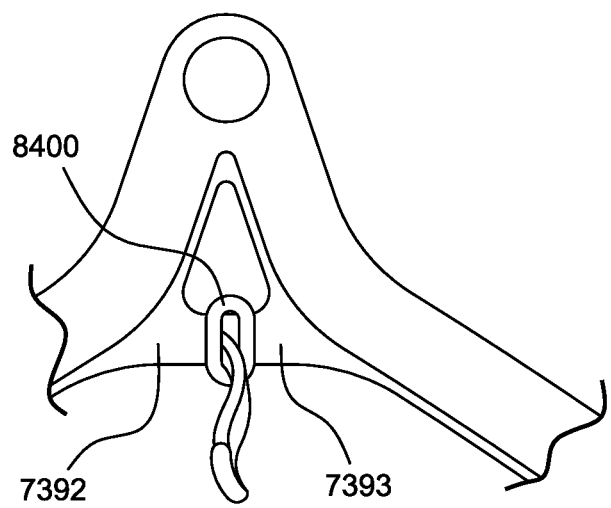

FIG. 21A-1 shows front view of a part of a positioning and stabilising structure 3300 comprising insert member 8387 in accordance with one form of the present technology.

Figures 2, 27B:
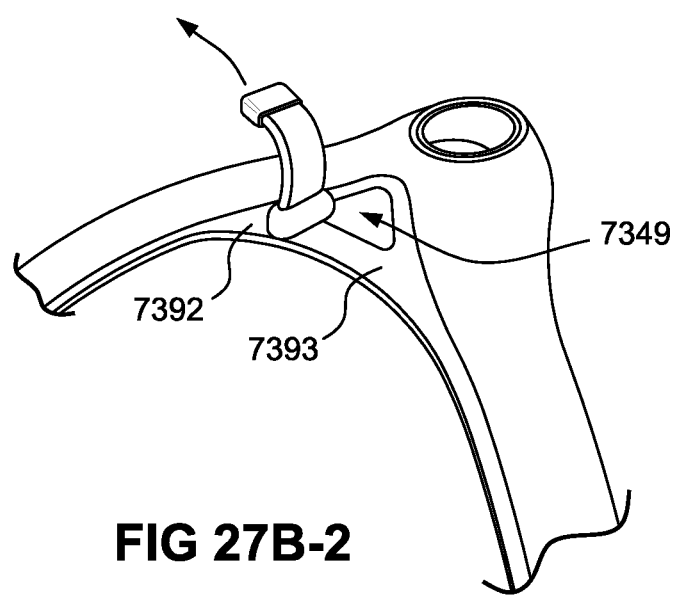

FIG. 21A-2 shows side view of a part of a positioning and stabilising structure 3300 comprising insert member 8387 in accordance with one form of the present technology.

FIG. 21A-3 shows perspective view of a part of a positioning and stabilising structure 3300 comprising insert member 8387 in accordance with one form of the present technology.

Figure 21B:
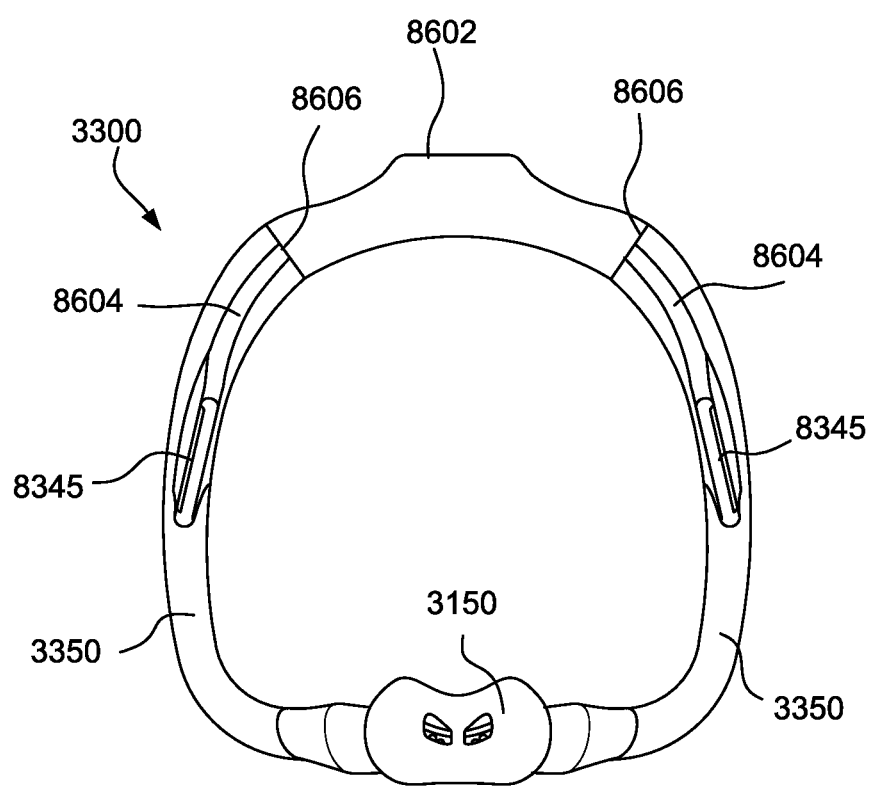

FIG. 21B shows a positioning and stabilising structure 3300 comprising the insert member 8387 of FIG. 21A-1.

Figure 22:
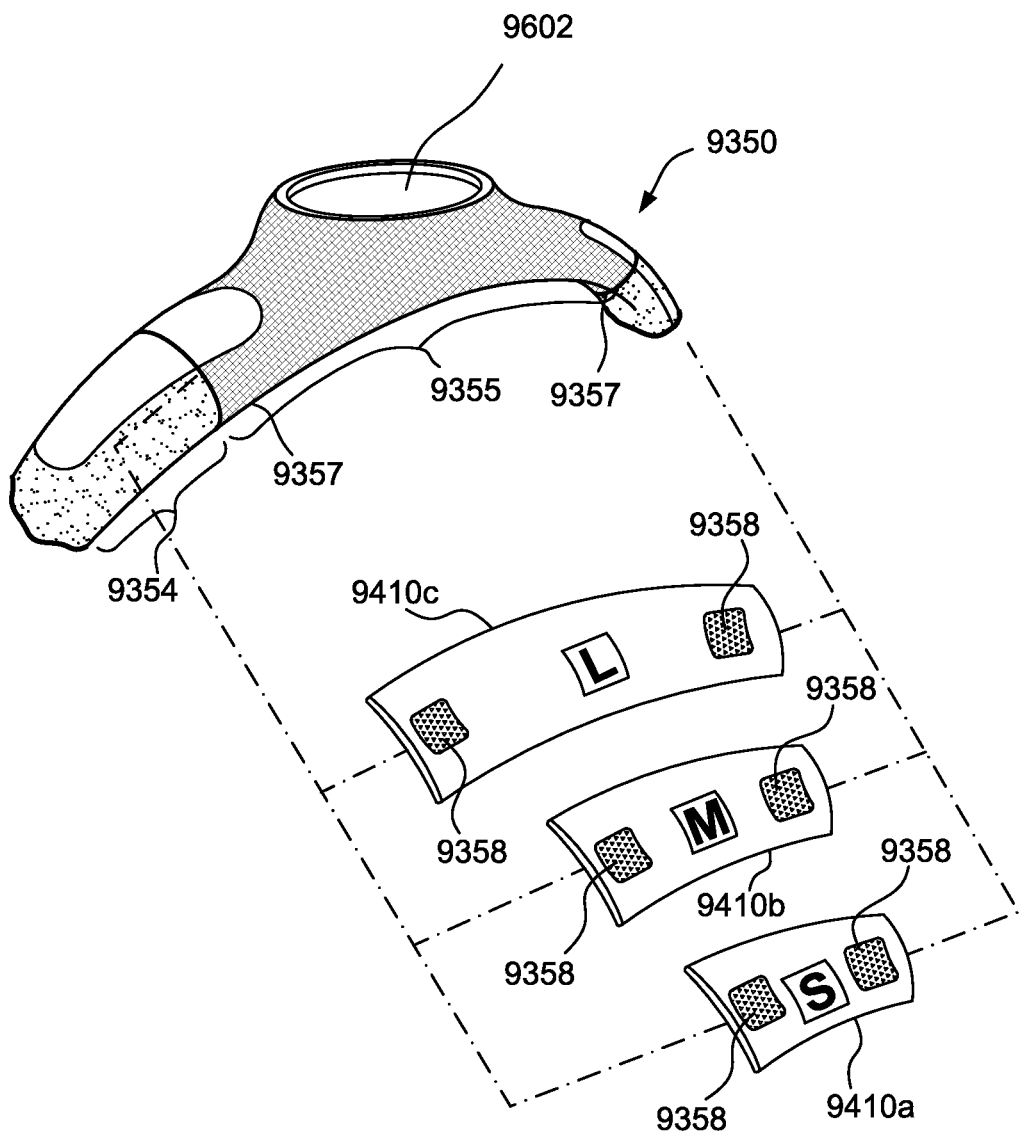

FIG. 22 shows a part of a patient interface comprising a stretchable section 9355 and insert members 9410 in accordance with one form of the present technology.

Figure 23A:
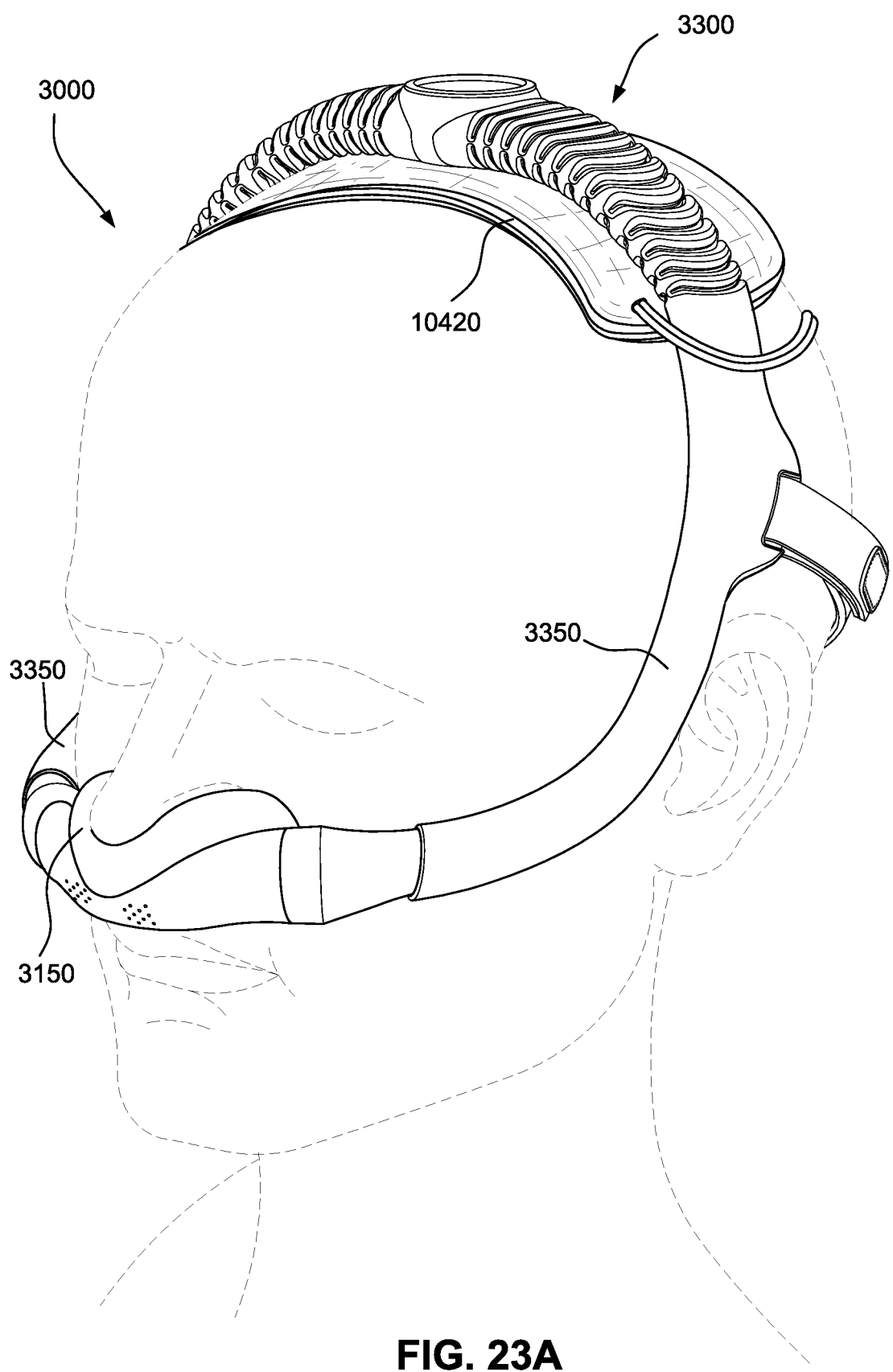
Figure 23B:
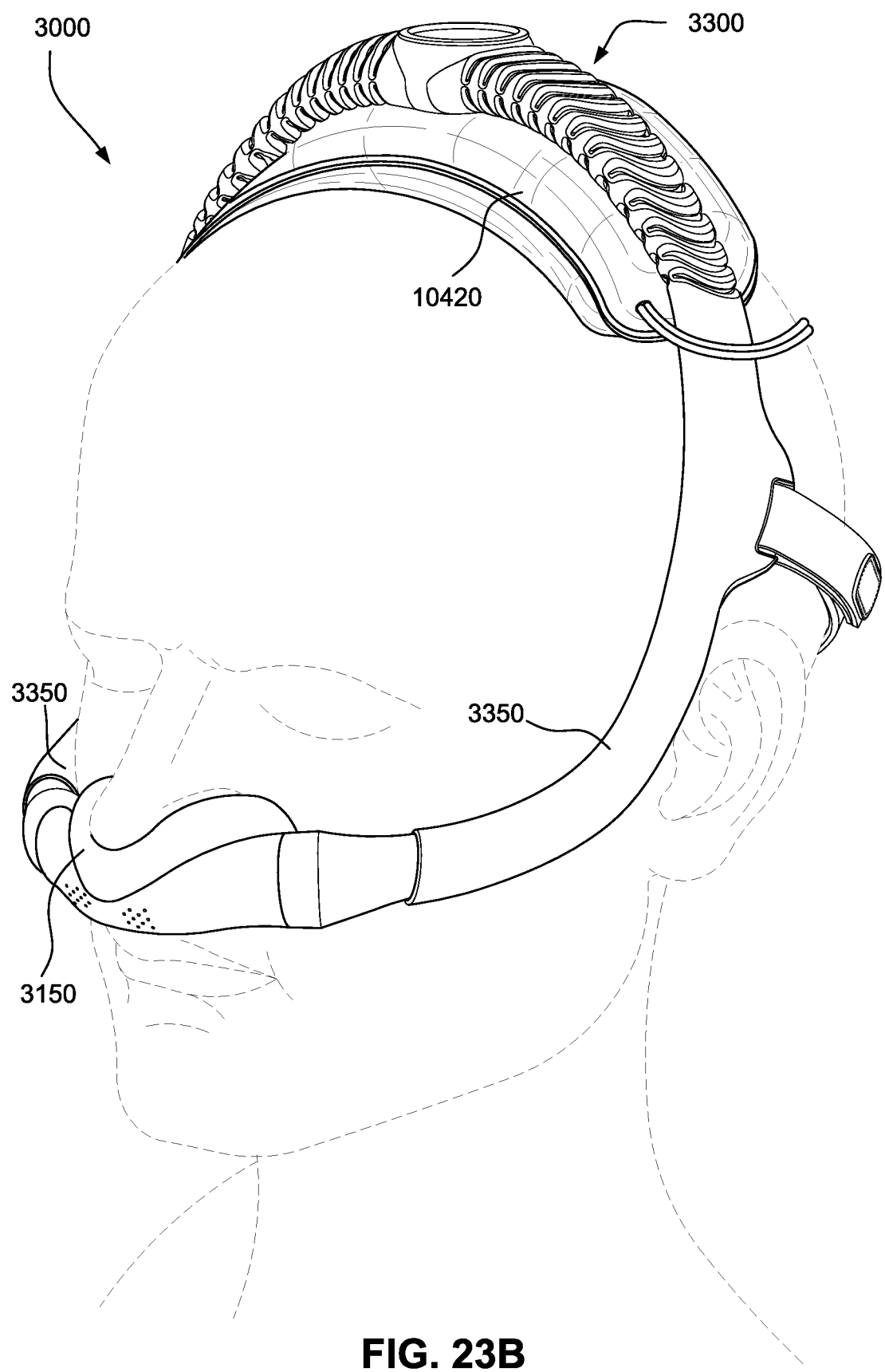

FIGS. 23A and 23B shows a part of a patient interface comprising an inflatable portion 10420 in accordance with one form of the present technology.

Figure 24:
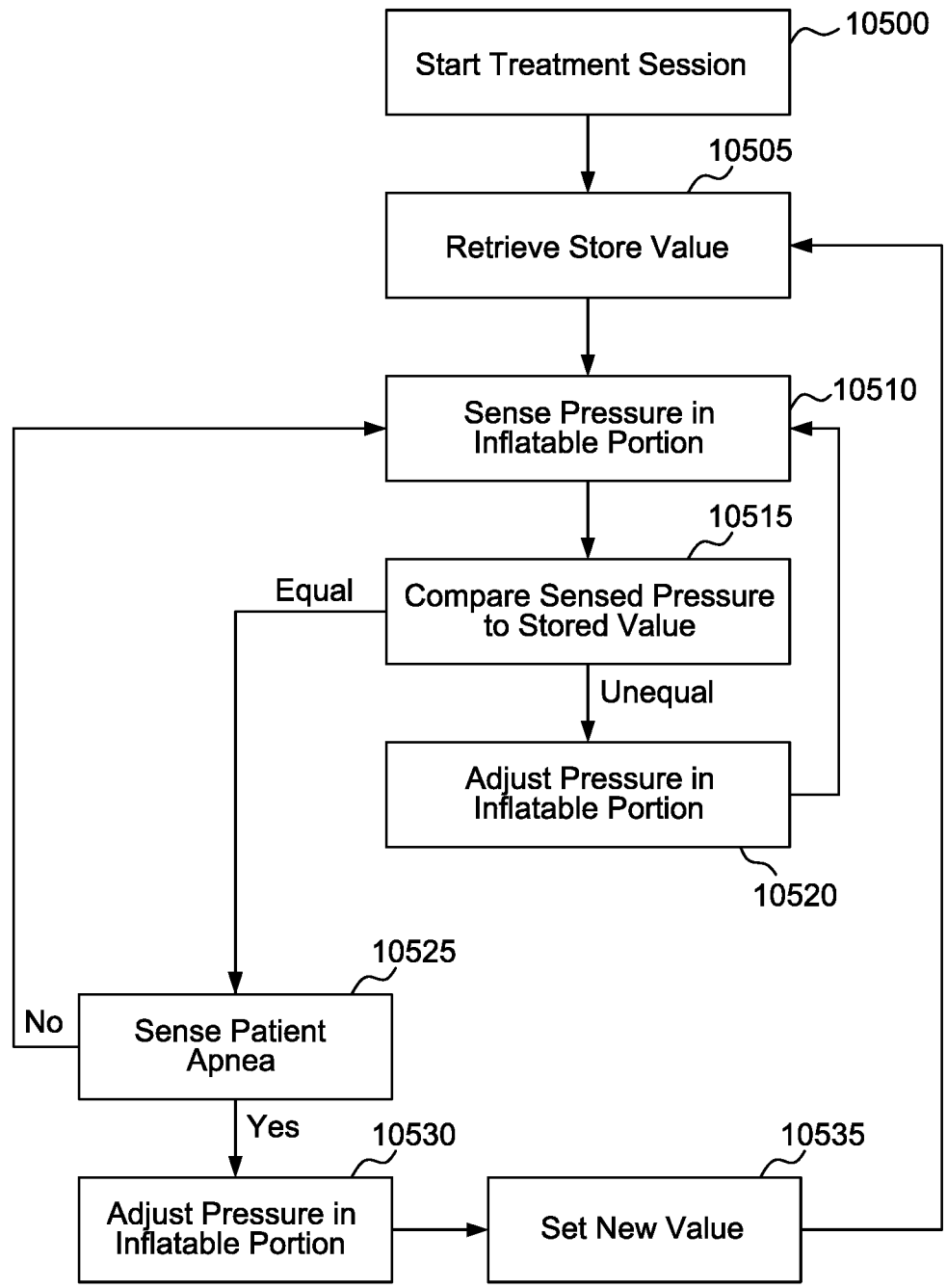

FIG. 24 shows a flow chart illustrating controlled adjustment of the inflatable portion 10420 of FIGS. 23A and 23B.

7.7 Adjustment Mechanism

Figure 25A:
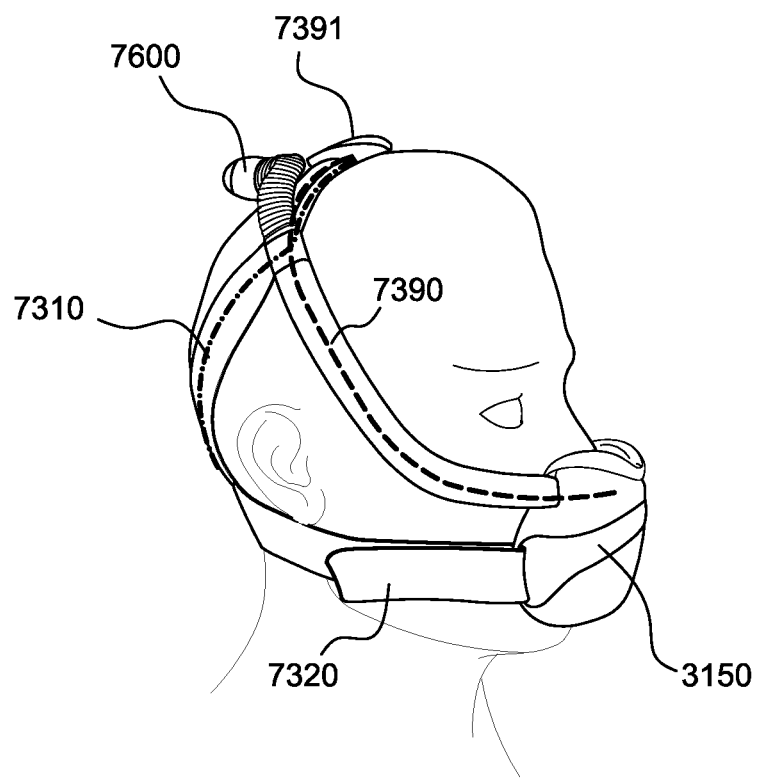
Figure 25B:
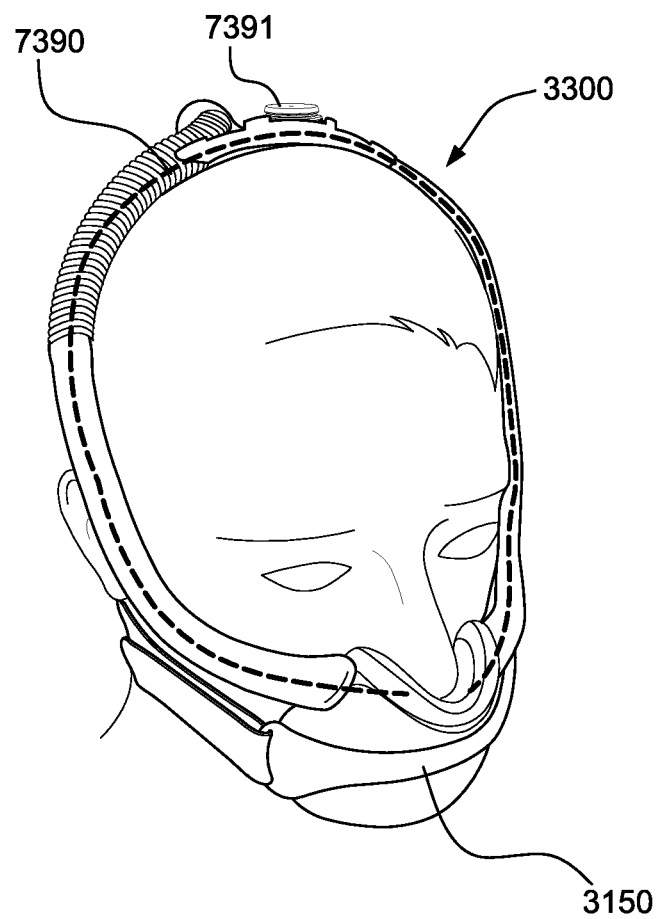
Figure 25C:
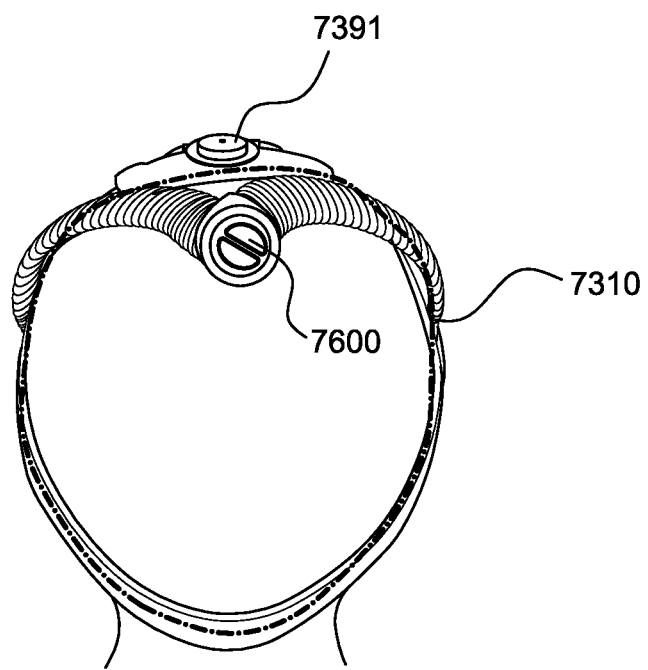

FIGS. 25A, 25B and 25C show a patient interface comprising a positioning and stabilising structure 3300 worn by a patient with one head size in accordance with one form of the present technology.

Figure 26A:
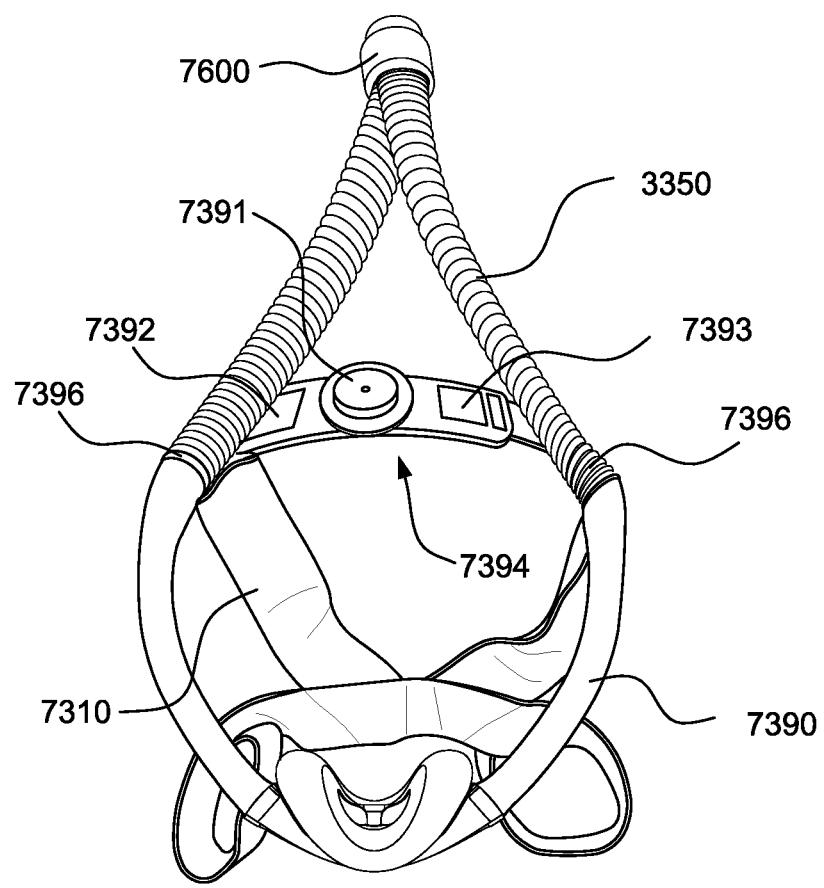
Figure 26B:
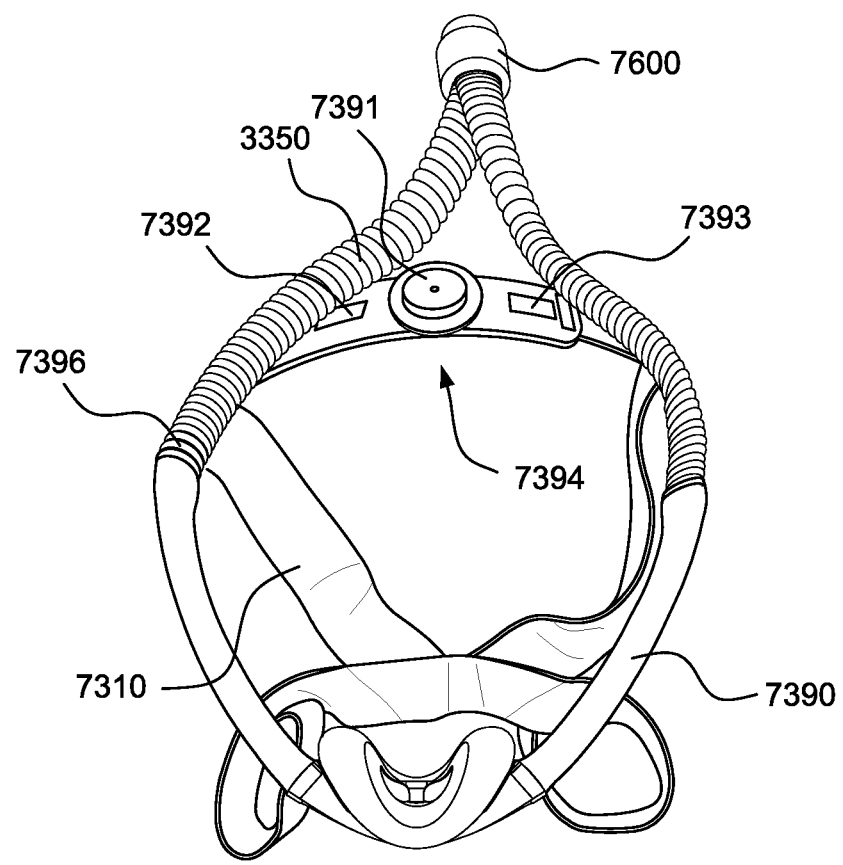

FIGS. 26A, 26B show a patient interface comprising a positioning and stabilising structure 3300 in accordance with one form of the present technology.

FIG. 27A shows alternative forms of an adjustment mechanism for a positioning and stabilising structure 3300.

FIGS. 27B-1 and 27B-2 show a further alternative form of an adjustment mechanism for a positioning and stabilising structure 3300.

Figure 28:
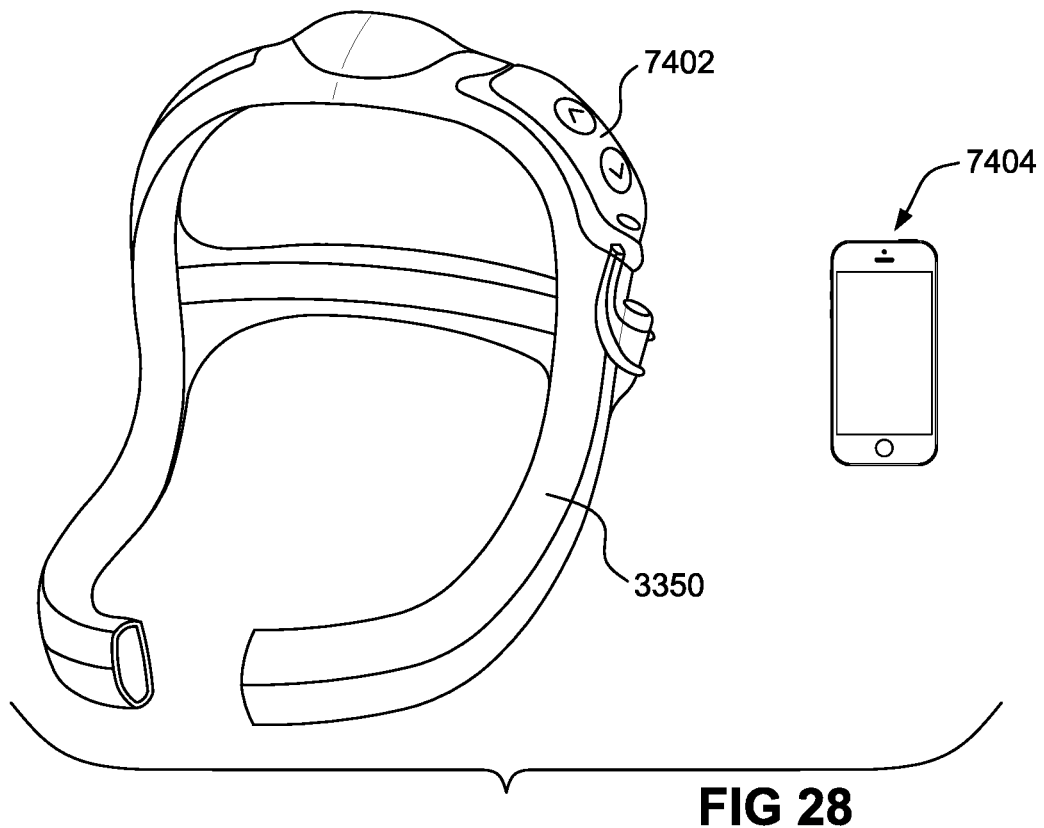

FIG. 28 shows a patient interface comprising an adjustment mechanism in the form of an electronic controller.

Figure 29:
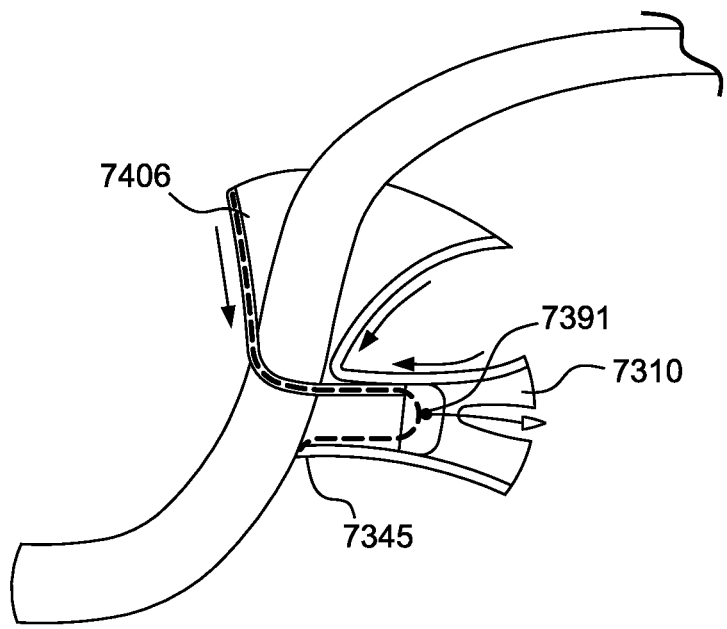

FIG. 29 shows a patient interface comprising an adjustment mechanism wherein the size of a front hoop and rear strap can be simultaneously controlled.

Figure 30A:
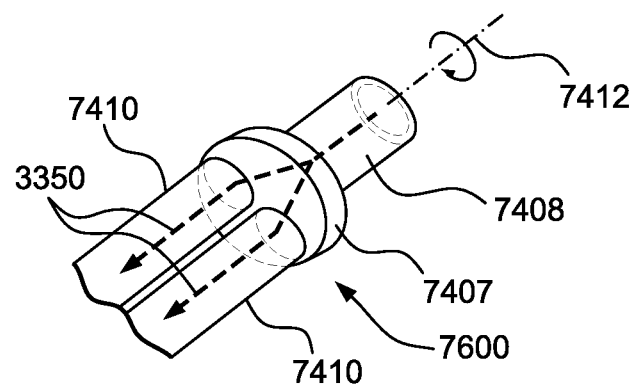
Figure 30B:
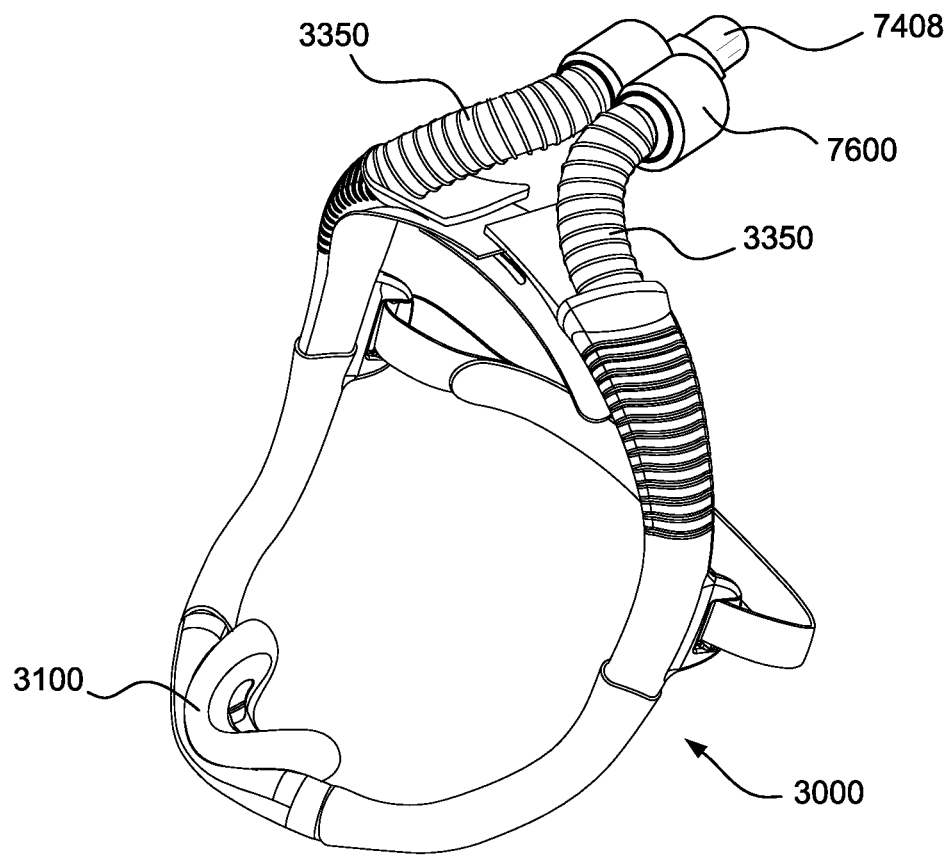

FIGS. 30A and 30B show one form of a y-shaped connection with a corresponding connection port comprising a single swivel.

Figure 31A:
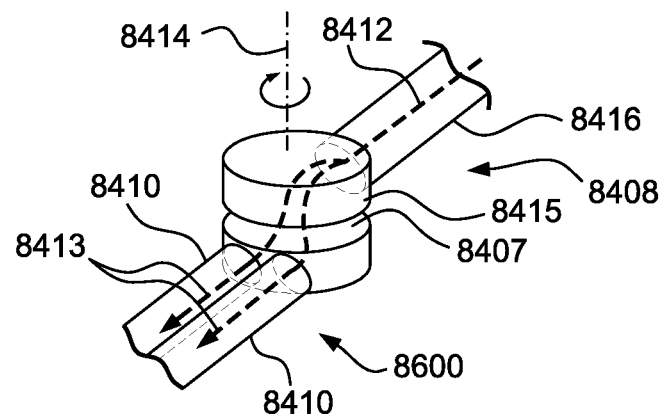
Figure 31B:
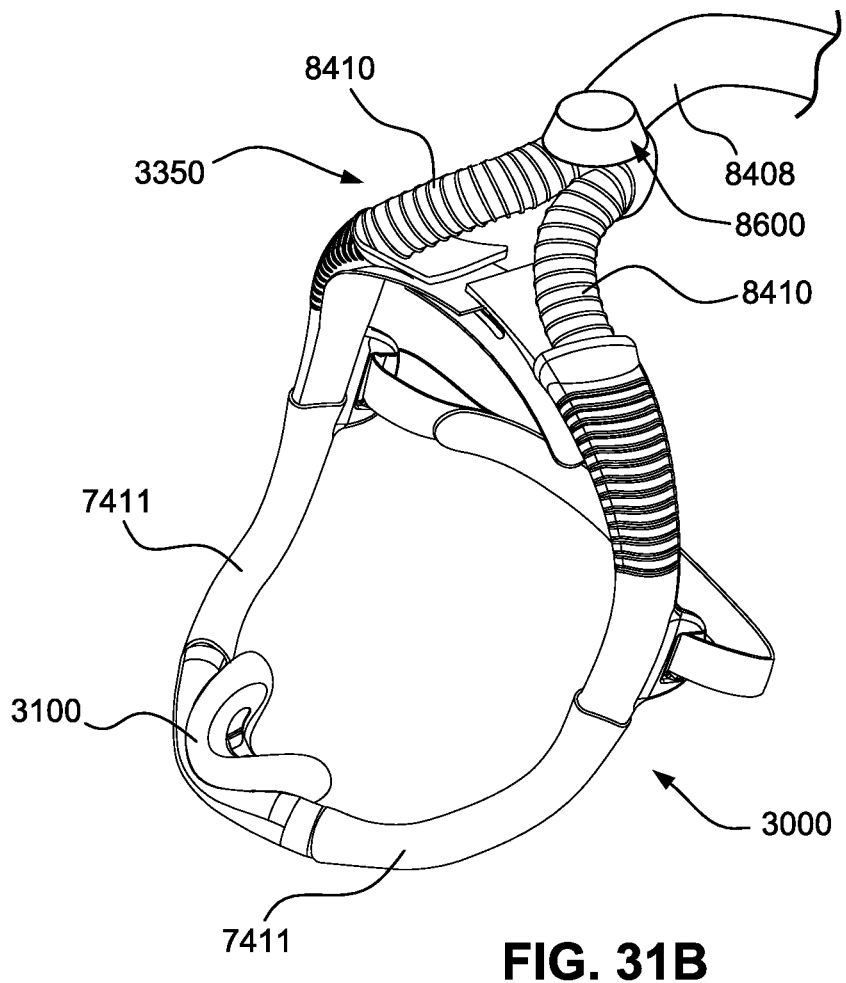

FIGS. 31A and 31B show one form of a y-shaped connection with a corresponding connection port comprising two swivels.

Figure 32A:
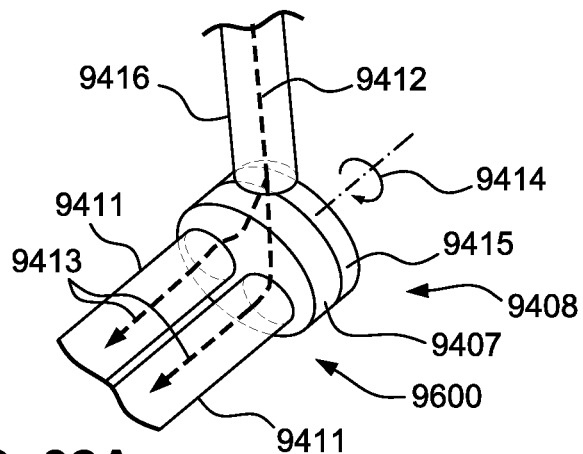
Figure 32B:
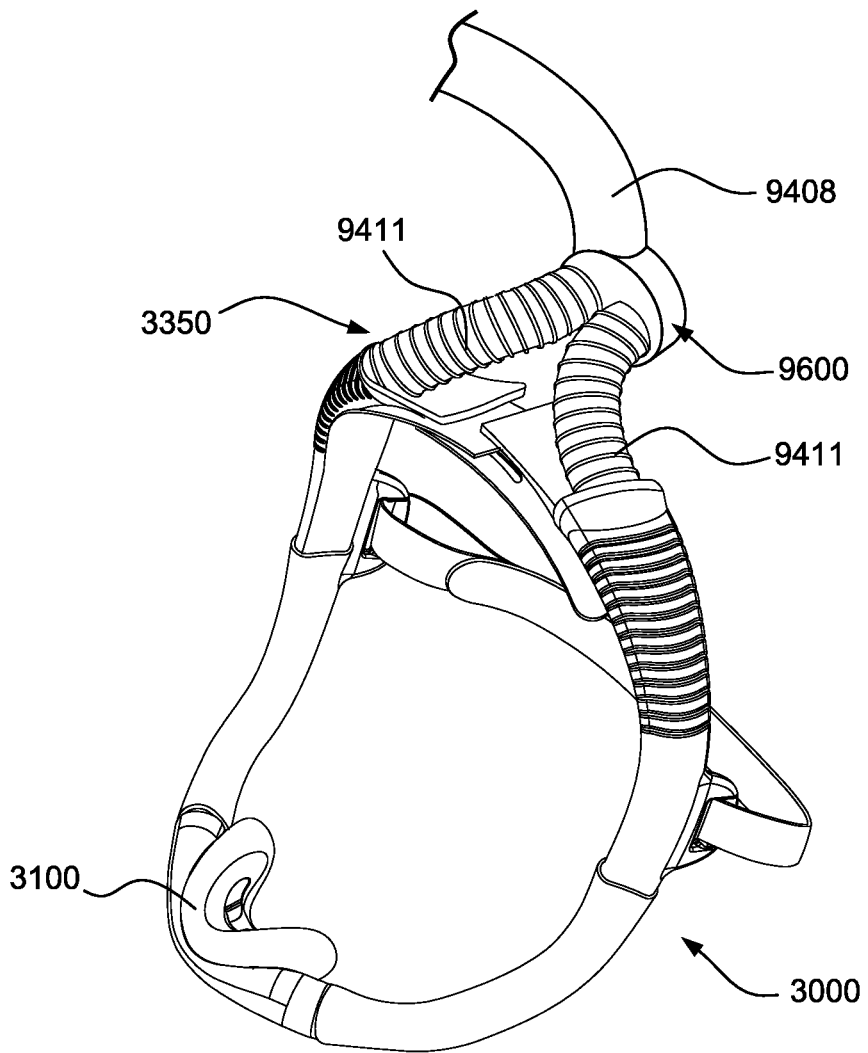

FIGS. 32A and 32B show a further form of a y-shaped connection with a corresponding connection port comprising two swivels.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

8.1 Therapy

Figure 1A:
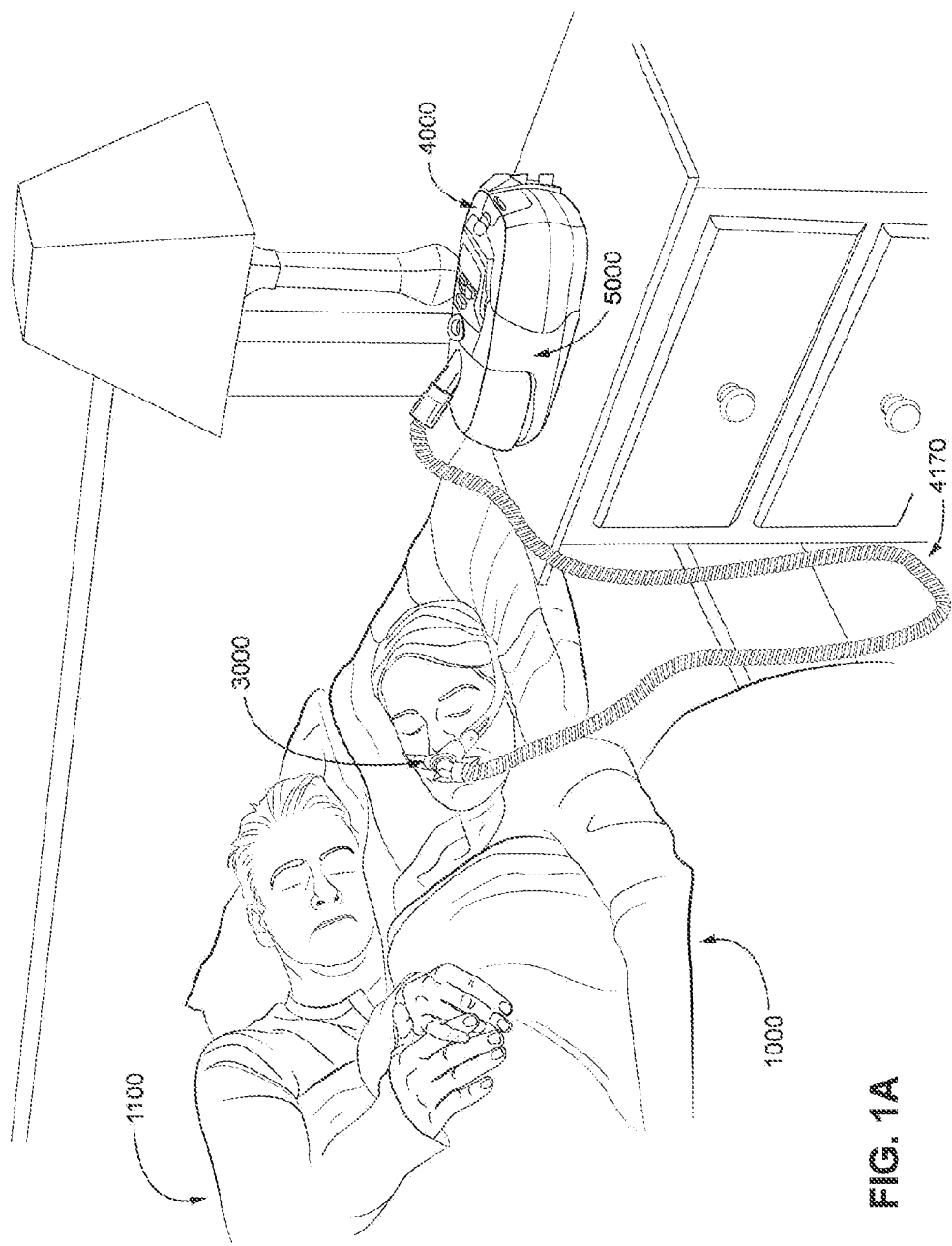
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.

In one form as shown in FIG. 1A, the present technology comprises a method for treating a respiratory disorder comprising the step of applying positive pressure to the entrance of the airways of a patient 1000.

8.2 Treatment Systems

Figure 1B:
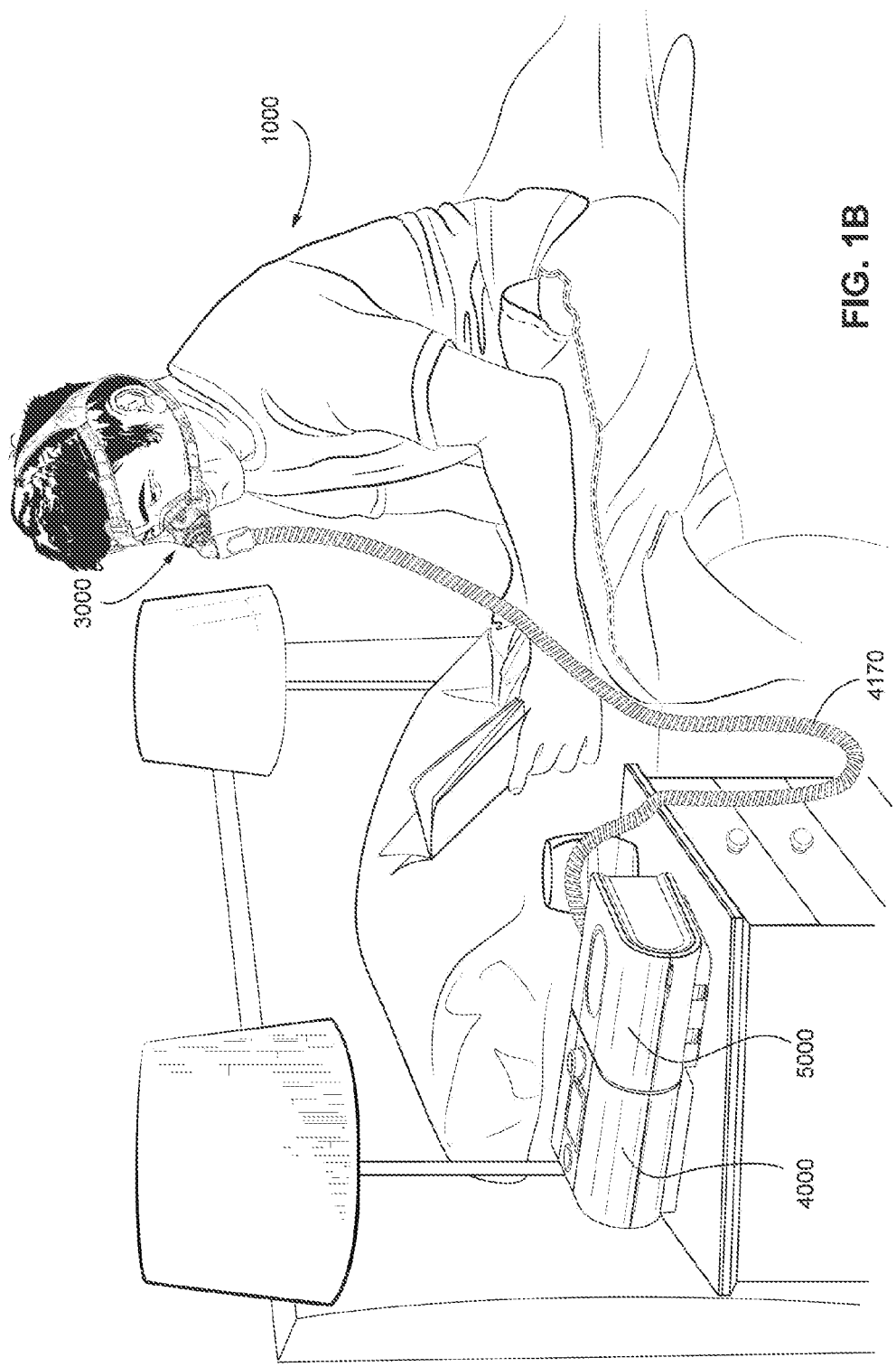
Figure 1C:

In one form, the present technology comprises an apparatus or device for treating a respiratory disorder. The apparatus or device may comprise an RPT device 4000 for supplying pressurised air to the patient 1000 via an air circuit 4170 to a patient interface 3000. FIGS. 1A, 1B and 1C illustrate treatment systems which utilise different forms of patient interface 3000

8.3 Patient Interface

With reference to FIG. 3A, a non-invasive patient interface 3000 in accordance with one aspect of the present technology comprises the following functional aspects: a cushion assembly 3150, a positioning and stabilising structure 3300 and a connection port 3600 for connection to air circuit 4170. In some forms a functional aspect may be provided by one or more physical components. In some forms, one physical component may provide one or more functional aspects.

The cushion assembly 3150 comprises a seal-forming structure 3100 and a plenum chamber 3200. In use the plenum chamber 3200 receives the supply of air at positive pressure from the air circuit 4170 and the seal-forming structure 3100 is arranged to seal with an area surrounding an entrance to the airways of the patient so as to facilitate the supply of air at positive pressure to the airways.

8.3.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

The seal-forming structure 3100 may be non-invasive, i.e. does not extend internally of the patient's airways. In some forms of the technology, no part of the seal-forming structure 3100 enters the patient's mouth in use. In some forms of the technology, the seal-forming structure 3100 is configured to leave the patient's mouth uncovered in use. In some forms of the technology, the seal-forming structure 3100 does not cover the patient's eyes in use.

In one form, the seal-forming structure 3100 comprises a sealing flange and a support flange. The sealing flange comprises a relatively thin member with a thickness of less than about 1 mm, for example about 0.25 mm to about 0.45 mm that extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use. In use the sealing flange can readily respond to system pressure in the plenum chamber 3200 acting on its underside to urge it into tight sealing engagement with the face.

In one form as shown in FIG. 1A, the seal-forming portion of the non-invasive patient interface 3000 comprises a pair of nasal puffs, or nasal pillows, each nasal puff or nasal pillow being constructed and arranged to form a seal with a respective naris of the nose of a patient. A nasal pillows patient interface 3000 is also shown in FIG. 3A.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 3000 comprises a seal-forming portion that forms a seal in use on an upper lip region (that is, the lip superior), a nasal bridge region and a cheek region of the patient's face. This is the case, for example, with the patient interface 3000 shown in FIG. 1B. This seal-forming portion delivers a supply of air or breathable gas to both nares of patient 1000 through a single orifice. This type of seal-forming structure may be referred to as a "nasal cushion" or "nasal mask".

In another form, the seal-forming structure is configured to form a seal in use with the underside of the nose around the nares and optionally with the lip superior. This type of seal-forming structure may be referred to as a "nasal cradle cushion" or "sub-nasal mask". The shape of the seal-forming structure may be configured to match or closely follow the underside of the patient's nose, i.e. the profile and angel of the seal-forming structure may be substantially parallel to the patient's naso-labial angle. In one form of nasal cradle cushion, the seal-forming structure comprises a septum member defining two orifices, each of which, in use, supply air or breathable gas to a different one of the patient's nares. The septum member may be configured to contact or seal against the patient's columella in use. In some forms of the technology, the seal-forming structure 3100 is configured to form a seal on an underside of the patient's nose without contacting a nasal bridge region of the patient's nose.

In one form the non-invasive patient interface 3000 comprises a seal-forming portion that forms a seal in use on a chin-region, a nasal bridge region and a cheek region of the patient's face. This is the case, for example, with the patient interface 3000 shown in FIG. 1C. This seal-forming portion delivers a supply of air or breathable gas to both nares and mouth of patient 1000 through a single orifice. This type of seal-forming structure may be referred to as a "full-face mask".

In another form the non-invasive patient interface 3000 comprises a nasal seal-forming structure 3170 in the manner of a nasal cushion or nasal cradle cushion and an oral seal-forming structure 3180 that is configured to form a seal in use around the mouth of a patient (which may be referred to as a "mouth cushion" or "oral mask"). In such a mask air or breathable is supplied in use through separate orifices to the patient's nares and the patient's mouth. This type of seal-forming structure 3100 may be referred to as an "oronasal mask". In one form, the nasal seal-forming structure 3170 and oral seal-forming structure 3180 are integrally formed as a single component. This is the case, for example, with the cushion assembly 3150 shown in FIGS. 4A, 4B and 4C. Alternatively, the nasal seal-forming structure 3170 and oral seal-forming structure 3180 may be formed separately and are configured to be attached together, either directly or indirectly, for example by connecting together frames attached to each cushion. For example, the nasal seal-forming structure 3170 and the oral seal-forming structure 3180 may be configured to be detached and re-attached in modular fashion. This enables the patient interface to be converted from an oro-nasal mask to a nasal mask or sub-nasal mask and vice versa, as desired by the patient and/or physician. This is the case, for example, with the cushion assembly 3150 shown in FIGS. 4D and 4E.

In some forms of the technology, the seal-forming structure 3100 is configured so that the seal-forming structure does not extend below a mental protuberance region of the patient's head in use.

Unless clearly specified otherwise, embodiments of patient interface according to the present technology may comprise any of the above types of seal-forming structure.

In certain forms of the present technology, a seal-forming structure 3100 is configured to correspond to a particular size of head and/or shape of face. For example one form of a seal-forming structure 3100 is suitable for a large sized head, but not a small sized head. In another example, a form of seal-forming structure 3100 is suitable for a small sized head, but not a large sized head.

8.3.2 Plenum Chamber

The plenum chamber 3200 receives, in use, pressurised breathable gas and is pressurised at a pressure above ambient pressure. In some forms of the present technology, the plenum chamber 3200 has a perimeter 3210 that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

The plenum chamber 3200 may receive the pressurised breathable gas through a plenum chamber inlet port that is sized and structured to receive the gas from another part of the patient interface 3000.

8.3.3 Positioning and Stabilising Structure

The seal-forming structure 3100 of the patient interface 3000 of the present technology may be held in sealing position in use by the positioning and stabilising structure 3300. Positioning and stabilising structure 3300 may be referred to as "headgear" since it engages the patient's head in order to hold the patient interface 3000 in a sealing position.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus.

The positioning and stabilising structure 3300 may comprise at least one tie. A tie will be understood to be a structure designed to resist tension. In use, a tie is part of the positioning and stabilising structure 3300 that is under tension. Some ties will impart an elastic force as a result of this tension, as will be described. A tie may act to maintain the seal-forming structure 3100 in a therapeutically effective position on the patient's head. In certain forms of the present technology, the positioning and stabilising structure 3300 may comprise ties in the form of headgear tubes 3350 and/or headgear straps, as will now be described.

8.3.3.1 Headgear Tubing

In the form of the present technology illustrated in FIG. 3A, the positioning and stabilising structure 3300 comprises at least one tube 3350 that delivers pressurised air received from a conduit forming part of the air circuit 4170 from the RPT device to the patient's airways, for example through the plenum chamber 3200 and seal-forming structure 3100. The tubes 3350 are an integral part of the headgear 3300 of patient interface 3000 to position and stabilise the seal-forming structure 3100 of the patient interface to the appropriate part of the patient's face (for example, the nose and/or mouth). This allows the conduit of air circuit 4170 providing the flow of pressurised air to connect to a connection port 3600 of the patient interface in a position other than in front of the patient's face which may be unsightly to some people. The headgear tubing may be as described in any one of the following patent applications the contents of which are incorporated herein by reference in their entirety: U.S. Patent Application No. 2019/0022343; U.S. Provisional Application No. 62/330,371; and U.S. Provisional Application No. 62/281,322.

Since air can be contained and passed through tubes 3350 in order to deliver pressurised air from the air circuit 4170 to the patient's airways, the positioning and stabilising structure 3300 may be described as being inflatable. It will be understood that an inflatable positioning and stabilising structure 3300 does not require all components of the positioning and stabilising structure 3300 to be inflatable.

In certain forms of the present technology, the patient interface 3000 may comprise a connection port 3600 located proximal a top, side or rear portion of a patient's head. For example, in the form of the present technology illustrated in FIG. 3A, the connection port 3600 is located on top of the patient's head. Patient interfaces in which the connection port 3600 is not positioned in front of the patient's face may be advantageous as some patients find a conduit that connects to a patient interface 3000 in front of the face to be unsightly and obtrusive. For example, a conduit connecting to a patient interface 3000 in front of the face may be prone to being tangled up in bedclothes or bed linen, particularly if the conduit extends downwardly from the patient interface in use. Forms of the technology with a patient interface with a connection port 3600 positioned proximate the top of the patient's head in use may make it easier or more comfortable for a patient to lie or sleep in one or more of the following positions: in a side or lateral position; in a supine position (i.e. on their back, facing generally upwards); and in a prone position (i.e. on their front, facing generally downwards). Moreover, connecting a conduit to the front of a patient interface may also cause a problem known as tube drag, wherein the conduit may provide an undesired drag force upon the patient interface 3000 thereby causing dislodgement away from the face (e.g., leaks between the seal-forming structure 3100 and the patient's face).

In the example of FIG. 3A, the at least one tube 3350 extends between the cushion assembly 3150 from the connection port 3600 across the patient's cheek region and above the patient's ear, i.e. a portion of tube 3350 that connects to cushion assembly 3150 overlays a maxilla region of the patient's head in use and a portion of tube 3350 overlays a region of the patient's head superior to the otobasion superior on the patient's head. The tube 3350 may also contact the patient's face anterior to the patient's ear, in order to limit contact with the patient's ear.

In the form of the present technology illustrated in FIG. 3A, the positioning and stabilising structure 3300 comprises two tubes 3350, each tube being positioned in use on different sides of the patient's head and extending across the respective cheek region, above the respective ear (superior to the otobasion superior on the patient's head) to the connection port 3600 on top of the patient's head. This form of technology may be advantageous because, if a patient sleeps on the side of their head and one of the tubes in compressed to block or partially block the flow of gas along the tube, the other tube remains open to supply pressurised gas to the patient. In other embodiments of the technology, the patient interface may comprise a different number of tubes, for example one tube, or three or more tubes. In one example in which the patient interface has one tube 3350, the single tube 3350 is positioned on one side of the patient's head in use (e.g. across one cheek region) and a strap forms part of the positioning and stabilising structure 3300 and is positioned on the other side of the patient's head in use (e.g. across the other region) to assist in securing the patient interface 3000 on the patient's head.

In the form of the technology shown in FIG. 3A the two tubes 3350 are fluidly connected at their upper end to each other and to connection port 3600. In one embodiment, the two tubes are integrally formed while in other embodiments the tubes are separate components that are connected together in use and may be disconnected, for example for cleaning, storage, and/or replacement. Where separate tubes are used they may be indirectly connected together, for example each may be connected to a T-shaped conduit having two conduit arms each fluidly connectable to the tubes 3350 and a third conduit arm or opening acting as the connection port 3600 and connectable in use to the air circuit 4170.

The tubes 3350 may be formed of a semi-rigid material such as an elastomeric material, e.g. silicone. The tubes 3350 may have a natural, preformed shape and be able to be bent or moved into another shape if a force is applied to the tubes. For example, the tubes 3350 may be generally arcuate or curved in a shape approximating the contours of a patient's head between the top of the head and the nasal or oral region.

The exemplary form of the technology illustrated in FIG. 3A has tubes 3350 which curve around the upper part of the patient's head from the upper end of the tubes 3350 that connect to connection port 3600 on top of the head to the point at which the rear headgear strap 3310 connects to the tubes 3350 substantially without any curvature in the sagittal plane. In between the point at which the rear headgear strap 3310 connects to the tubes 3350 and the lower ends of the tubes 3350 where they connect with the cushion assembly 3150 in front of the patient's airways under the nose, the tubes 3350 curve forwards between the patient's ears and eyes and across the cheek region. The radius of curvature of this section of the tubes 3350 may be in the range of approximately 60 mm to approximately 100 mm, for example between approximately 70 mm to approximately 90 mm, for example 80 mm. The lower end of the tubes 3350 and the section of the tubes 3350 at which the rear headgear strap 3310 connects to the tubes 3350 may subtend an angle in the range of approximately 65° to approximately 90°, for example between approximately 75° to approximately 80°.

In certain forms of the technology, one or more portions of the tubes 3350 may be rigidized by one or more rigidizing or stiffening elements. Examples of rigidizing elements include: sections of the tubes 3350 that are comparatively thicker than other sections; sections of the tubes 3350 that are formed from a material that is comparatively more rigid that the material forming other sections; and a rigid member attached to the inside, outside or embedded in a section of tube. The use of such rigidizing elements helps to control how the positioning and stabilising structure 3300 will function in use, for example where the tubes 3350 is more likely to deform if forces are applied to them and where the shape of the tubes 3350 is more likely to be maintained if forces are applied. The selection of where such rigidizing elements are positioned in the tubes 3350 can therefore help to promote comfort when the patient interface 3000 is worn and can help to maintain a good seal at the seal-forming structure during use. Rigidizing or stiffening elements may be in positioning and stabilising structures 3300 which are configured to support relatively heavy seal-forming structures such as full face or oro-nasal cushion assemblies.

The tubes 3350 in the form of the technology shown in FIG. 3A have a length of between approximately 15 cm and approximately 30 cm, for example between approximately 20 cm and approximately 27 cm. In one embodiment the tubes are approximately 25 cm long. The length of the tubes 3350 is selected to be appropriate to the dimensions of the heads of typical patients, for example the distance between the region proximate the top of the head (e.g., overlaying the frontal and/or parietal bones) where the upper end of the tubes 3350 are situated to the region proximate the openings to the patient's airways at which the lower end of the tubes 3350 connect to the cushion assembly 3150 when following a generally arcuate path down the sides of the heads and across the patient's cheek region such as is shown in FIG. 3A. As described in more detail below, the patient interface 3000 is configured so that the length of the tubes 3350 can be varied in some forms of the technology and the above lengths may apply to the tube in a contracted, stretched or neutral state. It will be appreciated that the length of the tubes 3350 will depend on the length of other components in the patient interface 3000, for example the length of arms of a T-shaped conduit to which the upper ends of tubes 3350 connect.

The level to which the patient interface 3000 fits an individual patient can be altered by varying the length of the tubes 3350 and, alternatively or additionally, by altering the position of the patient interface 3000 on the patient's head. For example, a patient interface 3000 having tubes 3350 of a certain length can be adjusted to better fit a patient by moving the positioning and stabilising structure 3300 in the posterior or anterior direction on the patient's head. Positioning the connection port 3600 further forward (i.e. in the anterior direction) enables a patient interface 3000 having tubes 3350 of a certain length to fit a larger head than if the connection port 3600 is positioned further backward (i.e. in the posterior direction).

In certain forms of the present technology the patient interface 3000 is configured such that the connection port 3600 can be positioned in a range of positions across the top of the patient's head so that the patient interface 3000 can be positioned as appropriate for the comfort or fit of an individual patient. One way this can be achieved so that the cushion assembly 3150 forms an effective seal with the patient's face irrespective of the position of the connection port 3600 on the patient's head is to de-couple movement of the upper portion of the patient interface 3000 from the lower portion of the patient interface 3000. Such de-coupling can be achieved using, for example, mechanisms that allow parts of the headgear tubes 3350 to easily move or flex relative to other parts of the patient interface 3000. Lower headgear portions may remain relatively static against the patient's face (e.g., because of a frictional force, material inextensibility, etc.) so that substantially no leaks form between the seal-forming structure 3100 and the patient's face, while upper headgear portions may be able to move without affecting the position of the lower headgear portions. Such mechanisms will be described below.

In a certain form of the present technology, the patient interface 3000 is configured such that the connection port 3600 is positioned approximately at a top point of the patient's head. The connection port 3600 may be positioned in the sagittal plane and aligned with the otobasion superior points in a plane parallel to the coronal plane. The otobasion superior points are identified in FIG. 2D. As will be described below, in some forms of the technology, the headgear 3300 is configured to be worn in different positions, with the effect that the connection port 3600 may be positioned proximate the top of the patient's head in the sagittal plane up to around 20 mm forward or 20 mm rearward of the otobasion superior points.

The cross-sectional shape of the tubes 3350 may be circular, elliptical, oval, D-shaped or a rounded rectangle, for example as described in U.S. Pat. No. 6,044,844, the contents of which are incorporated herein. A cross-sectional shape that presents a flattened surface of tube on the side that faces and contacts the patient's face or other part of the head may be more comfortable to wear than, for example a tube with a circular cross-section.

In some forms, the cross-sectional width and/or height of the tubes 3350 may be in the range of approximately 8 mm to approximately 25 mm. In some forms, the cross-sectional width and/or height of the tubes 3350 may be in the range of approximately 10 mm to approximately 20 mm. In some forms in which the tubes have a D-shaped cross-section, for example in the case of the longitudinal section of headgear tubing 3350 shown in FIG. 3H, the tubes 3350 have a width in the range of approximately 15 mm to approximately 25 mm, for example approximately 20 mm, and a height in the range of approximately 8 mm to approximately 15 mm, for example approximately 10 mm. The height may be considered to be the dimension of the tube away from the patient's face, i.e. the distance between the patient contacting side 3348 and the outermost part of the non-patient contacting side 3349, while the width may be considered to be the dimension across the surface of the patient's head. In some forms, the cross-sectional thickness of the material forming the tubes 3350 may be in the range of approximately 0.8 mm to approximately 1.6 mm. In some forms, the cross-sectional thickness of the material forming the tubes 3350 may be in the range of approximately 1.0 mm to approximately 1.5 mm. In some forms, the cross-sectional thickness of the material forming the tubes 3350 may be approximately 1.3 mm.

The D-shaped cross-sectional tube 3350 shown in FIG. 3H has rounded edges 3347 flanking the patient contacting side 3348. Rounded edges in contact with, or proximate to, the patient's skin help the patient interface 3000 to be more comfortable to wear and to avoid leaving marks on, or irritating, the patient's skin. A tube with a D-shaped cross-sectional profile is also more resistant to buckling than other shaped profiles.

Also as described in U.S. Pat. No. 6,044,844, the tubes 3350 may be crush resistant to avoid the flow of breathable gas through the tubes if either is crushed during use, for example if it is squashed between a patient's face and pillow. Crush resistant tubes may not be necessary in all cases as the pressurised gas in the tubes may act as a splint to prevent or at least restrict crushing of the tubes 3350 during use. A crush resistant tube may be advantageous where only a single tube 3350 is present as if the single tube becomes blocked during use the flow of gas would be restricted and therapy will stop or reduce in efficacy.

The two tubes 3350 are fluidly connected at their lower ends to the cushion assembly 3150. In certain forms of the technology, the connection between the tubes 3350 and the cushion assembly 3150 is achieved by connection of two rigid components so that the patient can easily connect the two components together in a reliable manner. The tactile feedback of a 're-assuring click' or like sound may be easy for a patient to use or for a patient to know that the tube has been correctly connected to the cushion assembly 3150. In one form, the tubes 3350 are formed from silicone and the lower ends of the silicone tubes 3350 are overmolded to a rigid connector made, for example, from polypropylene. The rigid connector may comprise a male mating feature configured to connect to a female mating feature on the cushion assembly 3150, although the male/female features may be arranged the other way around.

In another example, a compression seal is used to connect the tube 3350 to the cushion assembly 3150. For example, a resiliently flexible (e.g. silicone) tube 3350 without the rigid connector may need to be compressed (e.g., squeezed) slightly to reduce its diameter so that it can be inserted into a port in the plenum chamber 3200. The inherent resilience of the silicone may push the tube 3350 outwards (e.g., returns toward the uncompressed state) in order to seal the tube 3350 in the port in an air-tight manner. In a hard-to-hard type engagement between the tube 3350 and port, a pressure activated seal such as a peripheral sealing flange may be used. When pressurised gas is supplied through the tubes 3350 the sealing flange is urged against the join between the tubes and the inner circumferential surface of the port of the plenum chamber 3200 to enhance the seal between them. If the port is soft and a rigid connector is provided to the tube 3350, the pressure activated seal as described earlier may also be used to ensure the connection is air-tight.

Similar connection mechanisms may be used to fluidly connect the tubes 3350 with a T-shaped top member defining the connection port 3600 or connectable to the connection port 3600 in some forms of the technology. In one embodiment, a swivel elbow connected at the connection port 3600 is rotatable in order to drive a port size adjustment mechanism that decreases or increases the size of the ports into which tubes 3350 are inserted in order to improve the fit of the tubes through an increase or decrease of compressive forces and to reduce unintended leakage.

8.3.3.2 Headgear Straps

In certain forms of the present technology, the positioning and stabilising structure 3300 comprises at least one headgear strap acting in addition to the tubes 3350 to position and stabilise the seal-forming structure 3100 to the entrance to the patient's airways.

8.3.3.2.1 Position of Headgear Straps

In one example, for example as shown in FIG. 3A, the positioning and stabilising structure 3300 comprises a rear headgear strap 3310 connected between the two tubes 3350 positioned on each side of the patient's head and passing around the back of the patient's head, for example overlaying or lying inferior to the occipital bone of the patient's head in use. The rear strap 3310 connects to each tube above the patient's ears. In other embodiments, for example for an oro-nasal mask, the positioning and stabilising structure 3300 additionally comprises one or more lower side headgear straps that connect between the tubes and pass below the patient's ears and around the back of the patient's head.

In one form of the present technology, the positioning and stabilising structure 3300 comprises a chin strap 3320 that, in use, extends under the patient's chin, for example as shown in FIGS. 10A and 10B. The chin strap 3320 may be connected to the headgear tubes 3350 or, in another embodiment, to the cushion assembly 3150 or a frame assembly operatively connected to the cushion assembly.

Certain forms of the present technology may comprise multiple headgear straps to increase stability as described above, for example a rear strap, side headgear straps, and a chin strap.

In certain forms of the technology, the positioning and stabilising structure 3300 comprises a mechanism for connecting a headgear strap to the seal-forming structure 3100. The headgear strap may be connected directly or indirectly to the seal-forming structure 3100. In the case of the patient interface 3000 shown in FIG. 3A, for example, a tab 3345 configured to connect to rear strap 3310 projects outwardly from each headgear tube 3350 in a generally posterior direction. The tabs 3345 have holes in them to receive the ends of rear strap 3310. The tabs 3345 may be positioned superior to the patient's ears, so that the rear strap 3310 connected to the tabs 3345 do not overlay the patient's ears.

In some forms of the present technology, the rear strap 3310 is adjustable. For example, in the case of the patient interface shown in FIG. 3C the rear strap 3310 is, in use, threaded through a hole in each tab 3345. The length of the rear strap 3310 between the tabs 3345 may be adjusted by pulling more or less of the rear strap 3310 through one or both of the tabs 3345. The rear strap 3310 may be secured to itself after passing through the holes in the tabs 3345, for example, with hook-and-loop fastening means. The rear strap 3310 therefore is able to be adjusted to fit around different head sizes. In some forms of the technology the angle of the rear strap 3310 relative to the headgear tubes 3350 or patient's head is able to be adjusted to fit around the patient's head at a different locations. This adjustability assists the headgear 3300 to accommodate different head shapes and sizes.

In some forms of the technology, the rear strap 3345 exerts a force on the headgear tubes 3350 to pull them in an at least partially posterior (e.g. rearwards) direction at the locations of the tabs 3345. The rear strap 3310 may also exert a force on the headgear tubes 3350 to pull them in an at least partially inferior (e.g. downwards) direction. The magnitude of this force may be adjusted by altering the length of the rear strap 3310 between the tabs 3345.

In some forms of the technology, such as the form shown in FIG. 3C, the direction of the force applied to the headgear tubes 3350 by the rear strap 3310 may also be altered. This direction may be altered by adjusting the angle of the rear strap 3310 relative to the headgear tubes 3350 or patient's head. In some forms of the technology the location at which the rear strap 3310 exerts a force on the headgear tubes 3350 may be altered by adjusting the location at which the rear strap 3310 is secured to the headgear tubes 3350.

The adjustability of the magnitude and direction of the force applied to the headgear tubes 3350 by the rear strap 3310 may advantageously enable the headgear 3300 to accommodate a range of head sizes and head shapes. The rear strap 3310 may balance forces in the headgear tubes 3350 which may assist the headgear to maintain its shape and an effective seal to the patient's face, while remaining comfortable.

In some forms of the technology, when worn by a patient, a point on the headgear tubes 3350 near the tab 3345 will receive a generally upward (e.g. superior) force from the upper portion of the headgear tubes 3350 due to a biasing mechanism (described in further detail below) acting to keep the headgear secured to the patient's head. Additionally, the point on the headgear tubes 3350 near the tab 3345 may receive a generally forward (e.g. anterior) and downward (e.g. inferior) force caused by a biasing mechanism acting to urge the seal forming structure 3150 upwards and into the patient's nose. The directions and magnitudes of the forces required for a secure fit and effective seal may vary between patients based on the position of the positioning and stabilising structure 3300 on the head, which may vary due to, for example, differences in head shapes and sizes. In some forms of the technology, the adjustability of the rear strap 3310 enables the forces to be balanced for a range of head shapes and sizes to hold the headgear 3300 in a comfortable position while maintaining an effective seal.

For example, to balance a large force acting in the anterior (e.g. forward) direction on the portions of the headgear tubes 3350 proximate the tabs 3345, the rear strap 3310 may be adjusted by pulling more of the rear strap 3310 through the slots in the tabs 3345, thereby causing the rear strap 3310 to shorten in length and, if the rear strap 3310 is elastic, to apply a larger force on the headgear tubes 3350 in the posterior (e.g. rearward) direction. Similarly, the angle of the rear strap 3310 may be adjusted as required to balance both the vertical and horizontal components of the forces acting on the portions of the headgear tubes 3350 proximate the tabs 3345, across a range of head shapes and sizes.

8.3.3.2.2 Form of Headgear Straps

In one example, the positioning and stabilising structure 3300 comprises at least one strap 3310 having a rectangular cross-section. In one example the positioning and stabilising structure 3300 comprises at least one flat strap. In another example the positioning and stabilising structure 3300 comprises at least one strap 3310 having a profile with one or more rounded edges to provide greater comfort and to reduce the risk of headgear straps marking or irritating the patient.

In one form of the present technology, a positioning and stabilising structure 3300 comprises a strap 3310 constructed from a laminate of a fabric patient-contacting layer, a foam inner layer and a fabric outer layer. In one form, the foam is porous to allow moisture, (e.g., sweat), to pass through the strap 3310. In one form, the fabric outer layer comprises loop material to engage with a hook material portion. The hook material portion may be positioned at a distal portion of the strap 3310.

In certain forms of the present technology, a positioning and stabilising structure 3300 comprises a strap 3310 that is extensible, e.g. resiliently extensible. For example the strap 3310 may be configured in use to be in tension, and to direct a force to draw the seal-forming structure 3100 into sealing contact with a portion of a patient's face. In an example the strap may be configured as a tie. In other forms of the technology, the positioning and stabilising structure 3300 comprises a strap 3310 that is adjustable in order to alter the length of the strap. For example, the strap 3310 may connect to tubes 3350 by a strap adjustment mechanism, e.g. hook-and-loop fasteners. An adjustable strap 3310 may add further adjustment capability to other adjustment features of the patient interface 3000 to enable a patient to improve comfort and fit. In some forms of the present technology the degree of adjustability provided by other parts of the positioning and stabilising structure may mean the patient interface 3000 is sufficiently adjustable without strap 3310 also being adjustable.

In certain forms of the present technology, a positioning and stabilising structure 3300 comprises a strap 3310 that is bendable and e.g. non-rigid. An advantage of this aspect is that the strap 3310 is more comfortable for a patient to lie upon while the patient is sleeping.

In certain forms of the present technology, a positioning and stabilising structure 3300 comprises a strap 3310 that comprises two or more strap bands separate by a split. A split strap 3310 may anchor the patient interface 3000 on the patient's head in a particularly stable fashion in the case of some patient interface designs.

In certain forms of the present technology, a positioning and stabilising structure 3300 provides a retaining force configured to correspond to a particular size of head and/or shape of face. For example one form of positioning and stabilising structure 3300 provides a retaining force suitable for a large sized head, but not a small sized head. In another example, a form of positioning and stabilising structure 3300 provides a retaining force suitable for a small sized head, but not a large sized head.

8.3.3.3 Headgear Tubing Adjustment Mechanism

In certain forms of the present technology, the positioning and stabilising structure 3300 comprises an adjustment mechanism 3360. Adjustment mechanism 3360 is configured to allow the positioning and stabilising structure 3300 to be dimensionally adjusted. In at least one embodiment, the adjustment mechanism 3360 may particularly allow length adjustment of the positioning and stabilising structure 3300 between the connection port 3600 and seal-forming structure 3100, for example length adjustment of a tie, for example the headgear tubing 3350. Additionally or alternatively, the adjustment mechanism 3360 is configured to enable the positioning and stabilising structure 3300 to be bendably adjusted, for example bending of the headgear tubing 3350. The adjustment mechanism 3360 allows the patient interface 3000 to be adjusted to improve the fit of the patient interface 3000 to the patient's head, and thereby to enable the patient interface 3000 to fit different size heads. A patient interface that fits a patient well is comfortable to wear, is likely to be more stable and thus reduces the likelihood of seal disruption and maintains the sealing structure against the entrance of the patient's airways with a comfortable level of headgear tension. These factors improve patient compliance with therapy, improving therapeutic results. It will be understood that the adjustment mechanism may comprise a plurality of mechanisms for adjustment. For example, combinations of adjustment mechanisms described below may be provided to headgear in some forms of the present technology.

For example, the adjustment mechanism 3360 may allow the size and/or shape of the patient interface 3000 to be adjusted. In one form of the technology, the length of tubes 3350 between the connection port 3600 and the seal-forming structure 3100 may be adjusted.

In some forms of the technology, the adjustment mechanism 3360 allows the size of the patient interface 3000 to be adjusted by a total of up to approximately 100 mm to allow the patient interface 3000 to fit a broad range of patients. For example, the adjustment mechanism 3360 may allow the total length of the tubes 3350 to be adjusted by a total of up to approximately 100 mm. In one form of the technology, the total length of the tubes 3350 can be adjusted by a total of up to approximately 80 mm. For example, the length of the tube 3350 positioned on each side of the patient's face in use may be adjusted by up to approximately 40 mm.

The patient interface 3000 may be configured and structured so that, if the positioning and stabilising structure 3300 exerts a force on the patient's face to retain the cushion assembly 3150 in sealing relationship with the patient's face against the force exerted by the gas at positive pressure inside the plenum chamber 3200, that force is approximately constant or within predetermined limits over the range of sizes the patient interface 3000 is able to adopt. This is described in more detail below.

Different forms of adjustment mechanisms 3360 will be described in the ensuing description. In some forms the adjustment mechanism 3360 is comprised as part of the headgear tubing 3350 while in other forms the adjustment mechanism 3360 is distinct from the headgear tubing 3350. Certain forms of the technology may comprise multiple adjustment mechanisms 3360 as described below.

In some forms of the technology the adjustment mechanism 3360 is configured to be manually adjusted to enable the patient interface 3000 to fit the patient comfortably and with therapeutic effectiveness, i.e. adjusted by the patient or other person. In other forms the adjustment mechanism 3360 is configured to automatically adjust to fit the patient. An automatic adjustment mechanism may provide an advantage in that it reduces the chances of a patient fitting the patient interface 3000 incorrectly or uncomfortably. On the other hand, some patients may prefer the ability to alter the fit of the patient interface themselves.

In some forms of the technology, the patient interface 3000 is configured such that different forms of seal-forming structure 3100 can be interchangeably connected to the positioning and stabilising structure 3300. The different forms of seal-forming structure 3100 may include seal-forming structures of different size and weight. For example, an oro-nasal cushion may be heavier than a nasal cushion. In such forms of the technology a manual adjustment mechanism may provide an advantage in that the mechanism can be initially set to suit the type of seal-forming structure being used. For example, the manual adjustment mechanism may be set to provide a tighter fit if a relatively heavy seal-forming structure is used to counteract the tendency of a relatively heavy seal-forming structure to pull on the positioning and stabilising structure 3100 in an inferior direction. Similar considerations may apply to seal-forming structures that are subject to movement by a patient's mouth (e.g. jaw drop).

8.3.3.3.1 Folding/Concertina Headgear Tubes

In certain forms of the technology, the adjustment mechanism 3360 comprises tubes 3350 having one or more folding portions, pleats, corrugations or bellows, i.e. the folding portions pleats, corrugations or bellows comprise the adjustment mechanism 3360. When each folding portion is in a first, folded configuration, the length of the respective tube 3350 is different to its length when the folding portion is in a second, unfolded configuration.

The patient interface 3000 shown in FIG. 3A comprises tubes 3350 comprising a concertina tube section 3362 between lengths of the tubes 3350 without concertinas. Concertina tube section 3362 comprises a plurality of folds or bellows able to fold and unfold independently or in concert to shorten or lengthen the concertina tube section 3362 and hence the respective tube 3350. The folds in concertina tube section 3362 may be able to be expanded (stretched) or contracted by differing degrees on different sides of the tube 3350. For example, the concertina folds on the side of the tube 3350 nearest the patient's head may be contracted more than those furthest from the patient's head, which increases the curvature of the tubes 3350. This allows the shape of the tubes 3350 to be altered as well as their length, which also helps the patient interface be adjusted to fit the patient's specific head size and head shape.

In certain forms of the technology the concertina tube sections 3362 provide for adjustment of the length of the tubes 3350 of the patient interface 3000 continuously through a range of different lengths. In some embodiments the length of each concertina tube section 3362 may be continuously adjustable. An adjustment mechanism 3360, such as a concertina section 3362, which provides for continuous adjustment may fit comfortably to a wide range of head sizes. In contrast, an adjustment mechanism which provides of adjustment between discrete lengths may fit less comfortably on a patient for whom the most comfortable fit would require a length between two of the discrete length options.

In some forms of the technology the tubes 3350 comprise a plurality of concertina tube sections 3362 at predetermined locations, each separated by lengths of the tubes 3350 without concertinas.

In some forms of the technology, concertina tube sections 3362 are situated in relatively straight portions of the tubes 3350. This avoids the tendency for concertina sections 3362 to straighten when pressurised gas is passed through the tubes 3350, which may alter the position of the patient interface on the patient's head and adversely affect the stability of the seal and/or flow impedance.

In the form of the technology shown in FIG. 3B, patient interface 3000 comprises tubes 3350 comprising concertina tube sections 3362 that are longer than the concertina tube sections 3362 shown in FIG. 3A. In the form of the technology shown in FIG. 3B the concertina tube sections 3362 span the majority of the length of the respective tube 3350 in between the point at which headgear strap 3310 connects to the tube 3350 and the upper end of the tube 3350 that connects to connection port 3600 (e.g., the concertina tube sections 3362 span the majority of the length of the upper portion of the tubes 3350). For example, the concertina tube sections 3362 may have a lower end at a point just above the point at which headgear strap 3310 connects to the tube 3350 and may have an upper end at the point where tube 3350 connects to connection port 3600. A longer concertina tube section 3362 may provide a greater extensibility to the tube 3350. A high extensibility may alternatively be provided by increasing the number of concertina folds in the concertina tube section 3362. A greater extensibility may be advantageous in enabling the patient interface 3000 to fit many patients with a large range of head sizes while exerting a desired level of retaining force on a patient's face to ensure a good seal across this range of head sizes.

In some examples, the concertina tube sections 3362 may be located entirely above the patient's ear (e.g., in the upper portions of the tubes 3350), so that the lower portions of the tubes 3350 and the seal-forming structure 3100 may be substantially unaffected by the movement (e.g., compression or extension) of the concertina tube sections 3362.

In the form of the technology shown in FIGS. 3C, 3D and 3E the patient interface 3000 is similar to the patient interface 3000 shown in FIG. 3B. One difference is the configuration of the concertina tube sections 3362. In the form of the technology shown in FIGS. 3C, 3D and 3E, the concertina tube sections 3362 have a width and diameter that vary along the length of each concertina tube section 3362. More particularly, the concertina tube sections 3362 taper so that the width and diameter of the tube at one end of each concertina tube section 3362 is smaller than the width and diameter of the tube at the other end of each concertina tube section 3362. More particularly still, the upper end of each concertina tube section 3362 (where the concertina tube section 3362 connects to connection port 3600) has a larger width and diameter than the lower end of each concertina tube section 3362 (where the concertina tube section 3362 connects to a section of tube 3350 without concertinas), with the width and diameter of the concertina tube section 3362 increasing gradually and approximately linearly in between the upper and lower ends. The tapering of the concertina tube section 3362 is also shown in FIG. 3F, which shows in plan view the patient interface 3000 of FIGS. 3C, 3D and 3E. The tapering of the concertina tube section 3362 is also shown in FIG. 3G, which shows the patient interface 3000 of FIG. 3F in cross-section along the line 3G-3G. The tapering of the concertina tube section 3362 fluidly connects the connection port 3600 to the lower lengths of tubes 3350 without concertinas in a manner that reduces discontinuities in the cross-sectional profile of the air path, providing a smooth transition to reduce added impedance and promote fluid flow along the tubes 3350.

One advantage of concertina tube sections 3362 for the adjustment mechanism 3360 is that concertina tube sections 3362 may be more readily able to curve or bend as well as extend longitudinally, in comparison to other adjustment mechanisms. FIG. 3J shows headgear 3300 worn in three different positions on a patient's head indicated by reference numerals with suffixes "a", "b" and "c". As shown in FIG. 3J, the concertina tube sections 3362a, 3362b and 3362c are curved to different extents with concertina tube section 3362a curving forwardly on the patient's head, concertina tube section 3362b having less curvature in the posterior/anterior direction and concertina tube section 3362c having substantially no curvature on the patient's head. The different curvatures may affect patient comfort, but may not affect pressurized airflow through the tubes 3350.

In some forms of the technology, the concertina tube sections 3362 are able to extend by different amounts on the front and rear (e.g. anterior and posterior) sides of the headgear tubes 3350. That is, the walls forming the concertina tube sections 3362 may be relatively more contracted (e.g. more folded) on one side of the tube, and relatively more extended (e.g. unfolded) on the opposite side of the tube, to facilitate a bend or curve in the tube. This effect is visible in FIG. 3L. As shown, the walls of the concertina tube section 3362 are less extended (e.g. more collapsed) on the anterior side than on the posterior side in the case of concertina tube section 3362a, i.e. when the headgear is worn on the patient's head forwardly of the coronal plane. The ability for the concertina tube sections 3362 to curve in the anterior direction helps enable the headgear 3300 to be worn in a forward position without causing the cushion assembly 3150 to roll forward and out of sealing contact with the patient's face, which may occur if the headgear tubes were rigid. The ability for the headgear tubes 3350 to curve in anterior or posterior directions assists in decoupling the connection port 3600 from the cushion assembly 3150. There is less difference in the amount of extension of the concertina tube section 3362c between the front and rear sides of the concertina tube section 3362c (i.e. when the headgear 3300 is worn in a rearward position on the patient's head) compared to the difference in the amount of extension of the concertina tube section 3362a between the front and rear sides of the concertina tube section 3362a (i.e. when the headgear 3300 is worn in a forward position on the patient's head). The concertina enables the headgear tubes 3350 to straighten (or curve) less in order to be worn rearwardly.

In one form, the concertina tube sections 3362 on each side of the patient interface 3000 are approximately 40 mm longer in a fully expanded configuration compared to a fully contracted configuration.

In other forms of the technology, the concertina tube sections 3362 may be situated at a different portion of the length of tubes 3350. One advantage of the patient interfaces 3000 shown in FIGS. 3A and 3B, in which the concertina tube sections 3362 are located at a position along the length of the tubes 3350 so that the concertina tube sections 3362 are in contact with the top and/or upper sides of the patient's head, i.e. a region of the patient's head superior to the otobasion superior of the patient's head, is that the concertina tube sections 3362 are not in contact with the patient's cheek region. This avoids the discomfort that might arise if a concertina tube section contacted a patient's cheek region in use.

The concertina tube sections 3362 may be vulnerable to collapsing, particularly when they are heavily stretched. This presents a risk that the concertina tube sections 3362 cause a blockage in tubes 3350 which restricts or prevents the delivery of breathable gas to the patient. In some forms of the technology, the patient interface 3000 comprises one or more structures configured to prevent or at least hinder collapsing of the concertina tube sections 3362. In one embodiment, the patient interface 3000 comprises one or more rigid or semi-rigid rings provided to the concertina tube sections 3362 and positioned circumferentially around the tubes 3350. For example, the rings may be placed inside the concertina tube sections 3362 or they may be moulded (for example co-moulded or overmoulded) with the concertina tube sections 3362. In another embodiment a helical element is provided along the concertina tube sections 3362 to hinder collapse. In such an embodiment, the sections of material between the pitch of each helix turn, known as the tape, may provide resiliency to the tube. The tape may be formed of a resilient material or otherwise be structured to provide the appropriate level of elasticity to exert sufficient tension forces on the tube for contraction. In other embodiments, the concertina tube sections 3362 are formed with concertina tube sub-sections having a higher thickness or being made of a stiffer material than other concertina tube sub-sections such that collapse is hindered.

In another form of the technology, the patient interface 3000 comprises an adjustment mechanism 3360 comprising tubes 3350 having one or more circumferential folds enabling adjacent sections of the tubes 3350 to fold longitudinally. When the circumferential folds are in a folded configuration, a length of the tube overlays an adjacent length of tube. The rigidity of the material from which the tubes 3350 are formed may be configured so that the tubes tend to stay in the folded configuration unless pulled apart by a substantial force (greater than, for example, a force exerted on the tubes 3350 during typical use of the patient interface 3000). Alternatively, the patient interface 3000 may comprise means to maintain the tubes in a folded configuration, for example clips. In another embodiment, magnets are embedded in the tube 3350 that align between overlaying folding portions when the tube 3350 is folded to maintain the tube in a folded configuration unless the magnets are pulled apart.

The patient interface 3000 shown in FIG. 5 comprises an adjustment mechanism 3360 comprising a fold portion 3364. Fold portion 3364 comprises a first tube wall portion 3366 able to fold over an adjacent tube portion 3368 by a varying degree by rolling over the adjacent tube portion. FIGS. 5A and 5B are cross-sectional views of the fold portion 3364 of the patient interface 3000 shown in FIG. 5. In FIG. 5A the rolling fold portion 3366 is folded over adjacent tube portion 3368 to a greater degree than how much it is folded over in FIG. 5B and therefore the length of the tube 3350 when the fold portion 3364 is in the configuration shown in FIG. 5B is longer than the length of the tube 3350 when the fold portion 3364 is in the configuration shown in FIG. 5A. It can be seen from FIGS. 5A and 5B that, at the location of the fold portion 3364, three layers of tube 3350 overlap each other, although the length of the overlapping tube sections differs between the configuration of FIG. 5A compared to the configuration of FIG. 5B. The rolling fold portion 3366 may comprise a localised section of tube wall that is thinner than other sections of the tube 3350.

Another form of folding adjustment mechanism 3360 for a positioning and stabilising structure 3300 of a patient interface 3000 is shown in FIG. 6. In this embodiment of the present technology, tubes 3350 extend from a connection port 3600 to tube ends 3352 which are configured to connect to a cushion assembly 3150 of the patient interface 3000. Tubes 3350 have a generally wavy shape along their length and comprises at least one curved portion, for example curved portions 3353A, 3353B. The tubes 3350 are formed of a material that has sufficient flexibility for the curved portions to increase in curvature or decrease in curvature to allow each tube to fit a smaller or larger head respectively. For example, the tubes 3350 may be formed of meta-silicon having a hardness of 40 durometer on the Shore hardness scale.

In the form of the technology shown in FIG. 6, a tube 3350 on one side of the patient's head extends, at an upper end, in a generally anterior-inferior direction away from the connection port 3600 and a generally inferior direction at the side of the patient's head proximate the point that headgear strap 3310 attaches to the tube 3350 such that there is an upper curved portion 3353A positioned generally over an upper side portion of the patient's head and having the outer part of the curved portion on the anterior side and the inner part of the curved portion on the posterior side. Below the point that headgear strap 3310 attaches to the tube 3350, the tube 3350 extends generally in the inferior direction and curves slightly forwards in the anterior direction. A lower curved portion 3353B is positioned in use generally above the patient's cheek region. A lower end of tube 3350 extends across the patient's cheek generally horizontally in the anterior direction towards tube ends 3352 which connect to cushion assembly 3150. The lower end of tube 3350 may be oriented slightly downwards, i.e. extending slightly in the inferior direction, when worn by some patients. The lower curved portion 3353B positioned generally over the patient's cheek region has the outer part of the curved portion on the posterior side and the inner part of the curved portion on the anterior side.

The lower portion of tube 3350 in FIG. 6 is structured and configured so that the tube 3350 is generally positioned, in use, away from the patient's eyes so that the tube 3350 does not enter into the patient's field of view, or at least does so minimally. This may be achieved by structuring the lower portion of tube 3350 so that the apex or the point of maximum curvature of lower curved portion 3353B is positioned in use over a rear region of the patient's cheek region.

Although not shown in FIG. 6, the tube 3350 positioned over the left side of the patient's face is structured symmetrically to the tube 3350 over the right side of the patient's face. In other forms, the tubes 3350 may have different structures on each side of the patient's face.

8.3.3.3.2 Telescopic Headgear Tubes

In certain forms of the technology, the adjustment mechanism 3360 comprises tubes 3350 having a first tube portion 3370 that is telescopically moveable relative to a second tube portion 3372.

The patient interface 3000 shown in FIG. 7A comprises an adjustment mechanism 3360 comprising first and second tube portions 3370 and 3372 that slide telescopically relative to each other. In the embodiment of FIG. 7A, first tube portion 3370 is connected to the connection port 3600 and is therefore positioned higher on the patient's head than the first tube portion when the patient interface is worn. The second tube portion 3372 has a smaller diameter than, i.e. fits inside, first tube portion 3370 and is fixedly connected to a part of the tube 3350 positioned lower on the patient's head when the patient interface is worn. First tube portion 3370 may be described as enveloping second tube portion 3372 through the telescopic movement between the two tube portions.

In certain forms of the present technology, the patient interface comprises a tube securing mechanism that secures the first and second tube portions 3370 and 3372 in a plurality of discrete positions relative to one another. For example, in the form of the technology shown in FIG. 7A, second tube portion 3372 comprises a plurality of raised ribs 3374 on an outer surface and first tube portion 3370 comprises one or more protrusions or detents (not shown) that interlock with the ribs 3374 to hold the first and second tube portions 3370 and 3372 in a plurality of relative longitudinal positions, enabling the length of the tubes 3350 to be adjusted. In other forms of the technology, the tube sections may be secured in a plurality of discrete positions using other interlocking mechanisms, for example one or more grooves or holes that interlock with one or more protrusions or detents. It will be appreciated that the grooves may be provided on a surface of either the first or second tube portions with the protrusions provided on a surface of the other of the first or second tube portion in a position to interlock with the grooves in use.

In one form, the patient interface 3000 of FIG. 7B comprises an adjustment mechanism 3360 comprising first and second tube portions 3370 and 3372 that slide telescopically relative to each other. The first tube portion 3370 may slide over the outer surface of the second tube portion 3372. The second tube portion 3372 is positioned lower on the patient's head when patient interface 3000 is worn than first tube portion 3370, i.e. second tube portion 3372 is downstream of first tube portion 3370. The patient interface 3000 has two similar such adjustment mechanisms 3360, one positioned on each side of the patient's head in use.

Patient interface 3000 comprises an upper tube member 3351 which is positioned over the top portion of the patient's head in use. First tube portions 3370 on each side of the patient's head are integrally formed as part of upper tube member 3351. A connection port 3600 is provided to upper tube member 3351, for example the upper tube member 3351 has an opening in an upper side of the central portion thereof.

The first tube section 3370 on each side of the patient's head may comprise a first or upper tab 3371 and the second tube portion 3372 may comprise a second or lower tab 3373. The second tab 3373 may be pushed towards the first tab 3371. For example, the user may place their thumb on the second tab 3373 and their index finger on the first tab 3371 and pinch the two tabs together such that the second tab 3373 moves towards the first tab 3371. Moving the second tab 3373 towards the first tab 3371 telescopically slides the first and second tube portions 3370 and 3372 to shorten the headgear tubes 3350. Moving the second tab 3373 away from the first tab 3371 telescopically slides the first and second tube portions 3370 and 3372 to lengthen the headgear tubes 3350.

The second tab 3373 may slide towards a peripheral edge of the first tube 3370 such that when the second tab 3373 contacts the peripheral edge it acts as a stop to prevent further shortening of the tube 3350.

The second tube portions 3372 of the patient interface 3000 shown in FIG. 7B are integrally formed with the lengths of tube 3350 that, in use, are positioned in contact with the side of the patient's head and across the patient's cheek region. So that the patient interface 3000 is comfortable to wear and able to adapt to the shape of a range of patients' heads, the lower parts of tubes 3350 (of which second tube portions 3370 are an integral part) may be formed of a semi-rigid material such as an elastomeric material, e.g. silicone. In contrast, upper tube member 3351 (and consequently first tube portions 3370) may be formed from a relatively rigid material.

One possible consequence of a patient interface in which a tube portion formed from a relatively flexible material telescopically moves relative to a tube portion formed from a relatively rigid material is that, when the inner tube portion is pushed towards the outer tube portion, the tube portion made of the relatively flexible material may buckle. This may affect the ease with which the length of tubes 3350 can be adjusted. The patient interface 3000 shown in FIG. 7B comprises rigidizing members 3379 to address this problem. Rigidizing members 3379 act to increase the rigidity of the section of second tube portion 3372 that moves, in use, in and out of first tube portion 3370. In the embodiment shown, rigidizing members 3379 are lengths of relatively rigid material provided to the upper side of each of second tube portions 3372. The rigidizing members 3379 may be mounted on the outer side of the second tube portions 3372 or they may be moulded (for example co-moulded or overmoulded) as part of second tube portions 3372. In certain forms of the technology, each rigidizing member 3379 may be integrally formed with the tab 3373 on an upper side of the tab 3373 on the respective second tube portion 3372.

The patient interface of FIG. 7B comprises a padded member 3330 on a patient contacting side of the upper tube member 3351 to improve comfort when the patient interface 3000 is worn. One or more padded members 3330 may be provided to any part of the positioning and stabilising structure 3300 of any of the forms of patient interface 3000 described in this specification unless otherwise stated. For example, padded members 3330 may be provided to a part of the tubes 3350 to make wearing the patient interface more comfortable. Padded members 3330 may be permanently attached to a part of tubes 3350, for example by being moulded (e.g. co-moulded or overmoulded) or adhered thereto. Alternatively, padded members 3330 may be removably attached to tubes 3350, for example using hook-and-loop fastening material or fasteners. Since padded members 3330 will, in use, be in contact with the patient's head, they may become dirty and the ability to remove them for cleaning and/or replacement may be advantageous.

Another form the present technology is illustrated in FIG. 7C. In this form, patient interface 3000 comprises a second tube portion 3372 that telescopically slides over the outer surface of the first tube portion 3370. That is, the tube portion telescopically fitting inside the other tube portion is positioned higher than the other tube portion on the patient's head in use.

In the embodiment of FIG. 7C, first tube portion 3370 is relatively rigid. Second tube portion 3372 comprises a relatively rigid ring member 3384 at its upper end. Ring member 3384 encircles the opening in the upper end of the second tube portion 3372. Second tab 3373 may be provided to, for example integrally formed with, ring member 3384. Since first and second tube portions 3370 and 3372 are both formed of relatively rigid materials, they are able to telescopically move relative to each other without buckling. The patient interface 3000 shown in FIG. 7C may therefore avoid the need for a rigidizing member such as is described in relation to FIG. 7B while still allowing the same length of extension of the tubes 3350.

Another form of telescopic adjustment of tubes 3350 is shown in FIG. 8. In this embodiment, a second tube portion 3372 of tubes 3350 telescopically slides relative to a first tube portion 3370 with a ratchet mechanism 3376. Ratchet mechanism prevents or hinders movement of the telescopically moveable first and second tube portions relative to each other in one or both directions unless the ratchet mechanism is released, for example by pushing buttons 3378. Buttons 3378 are each operatively connected to a locking member (not shown) that interlocks with grooves or protrusions (e.g. ribs 3374) on second tube portion 3372 unless button 3378 is pushed down. The buttons 3378 and associated locking members may assist in limiting accidental movement of the tube portions 3370, 3372 while the patient is sleeping.

Another form of ratchet mechanism 3376 is shown in the form of the technology shown in FIG. 7C. In this form, ratchet mechanism 3376 comprises a tongue 3397 provided to the head contacting side of second tube portion 3372. Tongue 3397 is connected to second tube portion 3372 at a lower end and extends generally along the length of second tube portion 3372. Tongue 3397 is free at its upper end and has a protrusion on its upper side. First tube portion 3370 comprises a plurality of grooves 3398 on its head contacting side. The protrusion on the end of tongue 3397 is configured to selectively mate with each of grooves 3398 in order to hold the first and second tube portions 3370, 3372 in relative position. Tubes 3350 may have a generally D-shaped cross-section with the flat part of the 'D' contacting the patient. Ratchet mechanism 3376 may be advantageously located on the head contacting side of the patient interface 3000 (such as is the case in FIG. 7C) as tongue-and-groove ratchet mechanism 3376 may be more effective if provided on a relatively flat region of tube 3350 to provide a larger contact area than that which would result if more curved surfaces mated in the ratchet mechanism.

In an alternative form of the technology, button 3378 comprises tabs positioned on the sides of tube 3350 that are squeezed inwardly to release an interlock mechanism and allow the telescoping tube sections to be moved relative to each other. The tabs may comprise a gap or window in the first tube section 3370, which envelopes the second tube section 3372, enabling a patient or clinician to squeeze together a section of the second tube section 3372 to release the interlock. Alternatively, the gap may be covered by one or more overmoulded buttons which are pressed to squeeze on the second tube section 3372 to release the interlock. Covering the gap with overmoulded buttons or otherwise avoiding gaps in the adjustment mechanism 3360 reduces the prospect of the patient's hairs being caught in the adjustment mechanism 3360, which may reduce comfort. In one exemplary embodiment, the adjustment mechanism 3360 is configured such that, when the sides of ring members 3384 at the upper end of the second tube portions 3372 are pressed inwardly, interlocking features between the second tube portions 3372 and first tube portions 3370 are released and telescopic movement between the tube portions 3370, 3372 is possible. For example, the ring member 3384 may comprise a silicone overmoulded hard plastic pinch button and one or more protrusions on its inner top surface to interlock with grooves on the top surface of the first tube portion 3370 so that, when the ring member 3384 is squeezed inwardly at the sides, the protrusions and grooves are pushed out of interlocking engagement.

The patient interface of FIG. 8 comprises padded members 3330 on a patient contacting side of the positioning and stabilising structure 3300 to improve comfort when the patient interface 3000 is worn. The padded members 3330 may be constructed from a flexible and/or compressible material (e.g., foam) in order to comfortably contact the patient's head.

Another form of telescopic adjustment of tubes 3350 is shown in FIG. 9. In this embodiment the tube 3350 comprises a plurality of nested concentric tube sections 3375a, 3375b and 3375c that slide relative to each other. Each nested concentric tube section 3375 can be fully exposed or fully covered by telescopically extending or retracting an adjacent nested concentric tube section 3375 relative to it with the nested concentric tube sections interlocking with one another in fully extended or contracted positioned to hold their position, for example via a snap-fit mechanism. In some embodiments, the nested concentric tube sections 3375 can be held in intermediate positions, i.e. not fully extended or retracted.

In the embodiment shown in FIG. 9, each nested concentric tube section is marked with a visual indicator 3377 representative of the length of the tube 3350 if that tube section is exposed, for example 'S' for small 3377*a*, 'M' for medium 3377*b* and 'L' for large 3377*c*. Other forms of indicator may also be used, for example numerical indicators or coloured indicators. Physical indicators may also be used such as embossment which may be advantageous in dimly lit rooms prior to the patient sleeping. The nested concentric tube sections 3375*a-c* may be configured to extend or retract in a predetermined order.

Other forms of the technology comprise tubes 3350 formed from multiple telescoping tube sections that are coupled together in other ways. For example, each tube 3350 may comprise a central inner tube section flanked by two outer tube sections, the central inner tube section telescopically sliding in and out of each of the two outer tube sections in use. Alternatively, the central tube section may be outside the two outer tube sections.

In other forms of telescopically adjustable headgear tubes forms of other size indicators may be provided. In certain forms, a first tube section 3370 of a tube 3350 that envelopes a second tube section 3372 during telescopic movement between the two tube sections 3370, 3372 may comprise a window or gap through which a visual indicator 3377 on the second tube section 3372 can be seen to indicate the size of tube 3350 thus provided.

Another telescopic adjustment mechanism 3360 for headgear tubes 3350 is shown in FIG. 10A. In this embodiment the length of the headgear tubes 3350 is able to be adjusted by an adjustment mechanism 3360 comprising a cog or pinion 3383 that, when rotated, causes ribbed or racked portions of adjacent first and second tube sections 3370 and 3372 of tube 3350 to move telescopically, thus altering the length of the tube 3350. The first tube section 3370 may be integrally, permanently or removably connected to cushion assembly 3150. In the embodiment shown in FIG. 10A the adjustment mechanism 3360 is positioned at a lower end of the headgear tubes 3350. For example, adjustment mechanism 3360 may be provided in or adjacent to the cushion assembly 3150. This location of the adjustment mechanism 3360 may be easier for a patient to locate while wearing the patient interface 3000, particularly in a dark room. In the embodiment shown in FIG. 10A, rotation of the cog or pinion 3383 causes the lower end of tube 3350 to move telescopically in relation to the cushion assembly 3150.

In another form of the technology the adjustment mechanism 3360 is located at the connection port 3600 and a swivel elbow is provided to the cog or pinion so that rotation of the elbow causes movement of headgear tube sections relative to each other or relative to a T-shaped connection port member. A lock may be provided to prevent or limit rotation of the elbow when the desired arrangement is achieved.

Where a discrete number of relative positions of first and second tube sections is provided for by the telescopic adjustment mechanism it will be appreciated that a higher number of positions allows for more adjustment positions and promotes a better fit for patients. In some embodiments, 3, 4, 5, 6 or more adjustment positions are provided.

In certain forms of the technology, telescoping tube sections are configured to move relative to each other and be adjusted in a continuous fashion, i.e. the relative position of the tube sections is not constrained to discrete positions. This enables a greater degree of customisation in the length of the tubes 3350.

One example of a tube 3350 having a continuously adjustable length is shown in FIG. 10B in which tube section 3372 comprises a first threaded portion 3382 on first tube section 3370 which is in screwed engagement with a second threaded portion 3380 on second tube section 3372. The first and second threaded portions 3382, 3380 may be at least partially hollow and include a pathway for the pressurized airflow. In other words, pressurized air flows through the second threaded portion 3380, and the first threaded portion 3382 receives the second threaded portion 3380. Rotation of one of the threaded portions relative to the other adjusts the length of tube 3350 by translating the rotational movement into relative longitudinal movement of the associated tube sections. In other words, the first tube section 3370 may be moved apart from the second tube section 3372 so that the total length of the tube 3350 may be increased on one side of the patient's face. A length of the second threaded portion 3380 exposed to ambient may be greater as the length of the tube 3350 increases. A length of the second threaded portion 3380 within the first tube section 3370 may be greater as the length of the tube 3350 decreases. There may be separate first and second threaded portions 3382, 3380 on either side of the positioning and stabilising structure 3300. The left and right first and second threaded portions 3382, 3380 may be independently adjustable (although in some examples, a single adjustment may adjust both the left and right first and second threated portions 3382, 3380). One or both of the threaded portions are connected in rotational engagement to the other parts of their respective tube portions so that rotation of the threaded portions does not twist the rest of the tube 3350. The enveloped or smaller diameter second threaded portion 3380 may be provided on the lower end of the tube 3350, i.e. the part of tube 3350 connected to cushion assembly 3150 (as shown in FIG. 10B) or to the upper end of the tube 3350, i.e. the part of tube 3350 connected to the connection port 3600. An abutment or screw-limiting member (not shown) may be provided at one end of one of the threaded sections to prevent the threaded sections being screwed apart and detached accidently during use.

In one form of the technology, a screw mechanism is provided as a fine adjustment mechanism in addition to a coarser adjustment mechanism, which may be any of the other adjustment mechanisms described herein, for example. In general any of the adjustment mechanisms described herein may be used in combination, with a first adjustment mechanism providing a finer adjustment than a second adjustment mechanism.

In another embodiment of the present technology, telescoping sliding sections of tube 3350 are held in frictional contact through ribs on the sliding surface of one or both sliding sections. Alternatively, one or more O-rings may be provided between the telescopically sliding tube sections. The ribs or O-rings hold the tube sections together with sufficient frictional force to keep them in the desired position during normal use of the patient interface but enable their relative position to be adjusted on application or a sufficient longitudinal adjustment force.

In another form of the technology, telescopic tube sections may be secured in position using other securing mechanisms. In one example, a length of a strap is attached to one of the telescopic tube sections with a portion of hook-and-loop fastener material provided to the strap. The strap may be secured to a complimentary portion of hook-and-loop fastener material provided to the other telescopic tube section to secure the sections in the desired position and thereby effect adjustment of the length of tube 3350.

In the above-described embodiments of the present technology in which one or more tube sections are telescopically movable relative to other tube sections it will be appreciated that the tube sections are telescopically engaged in a substantially sealed manner to reduce the amount of breathable gas leaking from the patient interface. The manner in which this is achieved will differ depending on the nature of the telescopic engagement but one or more O-rings or other sealing members may typically be provided.

In the case of the patient interface 3000 shown in FIG. 7B, for example, an O-ring is provided on an inner surface of the lower end of first tube portion 3370. For example, the O-ring may be provided in a slot on the inner surface of the lower end of first tube portion 3370. The O-ring is in sealing contact with the outer surface of the upper end of second tube portion 3372. In other forms of the technology, the O-ring may be provided on the outer surface of the upper end of second tube portion 3372. In one example, the O-ring is provided to, or is integrally formed with, the rigidizing member 3379.

The configuration and structure of the sealing contact between the first and second tube sections that move telescopically may be selected to provide the appropriate level of friction to achieve a balance between the quality of the seal and the ease of adjusting the first and second tube sections. In some forms of the technology, for example the patient interface 3000 shown in FIG. 7B, it has been found that a minimum retaining force between the first and second tube sections 3370, 3372 may be approximately 10N and a maximum retaining force may be approximately 20N. If the retaining force is less than the predetermined minimum amount the first and second tube sections 3370, 3372 may move apart too easily and the length of tubes 3350 may be accidentally adjusted during normal use of the patient interface 3000, for example by being jogged by the patient or the patient's bedding, or as a result of the flow of gas at positive pressure through the tubes 3350. If the retaining force is more than the predetermined maximum amount the first and second tube sections 3370, 3372 may be too difficult for a patient to move to adjust the length of the tubes 3350.

In an alternative form of the technology, the inner or outer surface of the first or second tube portions 3370, 3372 may comprise one or more moveable flap seals, lip seals or a compressible gasket seal. In another form, there may be a controlled leak between the first and second tube portions 3370, 3372, such that the leak does not interfere with respiratory pressure therapy. In one form, the controlled leak may act as an additional washout vent.

In the above-described forms of the technology in which one or more tube sections 3370, 3372 are telescopically movable relative to other tube sections 3372, 3370, the patient interface 3000 may comprise one or more end stops to prevent the first tube section 3370 and the second tube section 3372 from coming apart. In one form, the inner tube section comprises a flange at its end, and the outer tube section comprises an end stop on an inner surface against which the flange abuts at the maximum extension of the tube sections.

Although a swivel elbow has been described, it is possible a ball and socket elbow may be used instead to provide six degrees of freedom for providing greater decoupling of tube drag forces.

8.3.3.3.3 Modular Tube Portions

FIG. 11 shows a patient interface 3000 in which the adjustment mechanism 3360 takes the form of a replaceable tube portion 3385 which can be removed from the patient interface 3000 and replaced with a replacement tube portion 3386 having a different length to the first tube portion or module 3385. The replaceable and replacement tube portions 3385 and 3386 may be described as tube modules.

In the example of FIG. 11, the replaceable tube portion 3385 comprises a T-shaped tube member that has three ports so that the replaceable tube portion 3385, in use, fluidly connects to each of tubes 3350 and the air circuit 4170. For example, a central port in the upper side of replaceable tube portion 3385 is configured to connect to connection port 3600 or comprise connection port 3600. For example, replaceable tube portion 3385 may be positioned in use on top of the patient's head.

Tube portion 3385 is able to be disconnected from the other parts of patient interface 3000 and replaced with replacement tube portions 3386*a* and 3386*b*. Replacement tube portions 3386*a* and 3386*b* have tube sections extending outwards from connection port 3600 by a differing amount to replaceable tube portion 3385. Any number of replacement tube portions may be provided but in the embodiment of FIG. 11, patient interface 3000 comprises 'small', 'medium' and 'large' replaceable portions.

In the form of the present technology shown in FIG. 12, patient interface 3000 comprises one or more tube insert members 3387*a* and 3387*b* configured to be selectively fluidly connected to the tub 3350 to alter the length of the tube. For example, tube insert members 3387*a* and 3387*b* are configured to be fluidly connected between tubes 3350 and cushion assembly 3150 to alter the effective length of tubes 3350. In alternative embodiments, the tube insert members may be connected to other parts of the patient interface, for example at an upper end of the tubes 3350 between the tubes 3350 and the connection port 3600. Each tube insert member 3387 may be marked with a size indication, for example 'M' for medium and 'L' for large and the like. One size of patient interface may be achieved with no tube insert members connected.

In a further form of the present technology shown in FIG. 20A, a positioning and stabilising structure 3300 comprises one or more tube insert members 7387*a*, 7387*b* and 7387*c*, wherein at least one of the inserts includes a coupling 7345. The coupling 7345 can have a hole such that the coupling may take the form of an eyelet 7345 and be arranged to receive the rear strap 3310 to the gas delivery tube 3350.

In the further form of the present technology, the tube insert members 7387 may be connected at a part of tube 3350, between a lower and upper segment of the tube. For example, the lower segment of tube 3350 may connect between a lower end of insert 7387 and the cushion assembly 3150, for example in substantially a middle section of the tube 3350. The upper segment of tube 3350 may connect between an upper end of insert 7387 and connection port 3600.

In this further form, the insert member 7387 forms a part of a hoop that passes over the top of the patient's head. The hoop incorporates the insert member 7387, the tubes 3350 and the cushion assembly 3150. In use, portions of the insert member extend across the patient's cheek regions and the hoop is preferably arranged so that portions of the insert member 7387 contact regions of the patient's head superior to an otobasion superior of the patient's head.

The tube insert members 7387*a*, 7387*b* and 7387*c* may be configured to be selectively fluidly connected to the tube 3350 to alter the actual length of the hoop. The tube insert member 7387 may have one or more different lengths and may be marked with a size indication, for example 'M' for medium and 'L' for large.

Referring now to FIGS. 20A and 20B. The position of eyelet 7345 may be different for any of the insert members 7387a, 7387b and 7387c. For example, the eyelet 7345 may be positioned proximal to the upper or lower end of insert 7387. Referring to FIG. 20B, the eyelet may be equally spaced, for example by a distance, x, away from each end, between both ends of insert 7387. In some forms, the position of the eyelet is skewed towards one end of insert 7387, i.e. a distance, y, is smaller than a distance, z, as shown in FIG. 20B. The position of the eyelet 7345 described above may be different between different sized insert members 7387 (e.g., insert 7387a may be equally spaced and insert 7387b may be skewed), and/or may form different versions of the same-sized insert member 7387 (e.g., insert 7387b includes an equally spaced version and a skewed version).

Advantageously, each length of insert 7387a, 7387b and 7387c can have a corresponding eyelet position optimised for fit around different head shapes and sizes. The different eyelet position for each length of insert 7387 ensures both the eyelet 7345 and the rear strap 3310 are preferably optimally positioned relative to the patient's ear. Further, the corresponding insert 7387 lengths and eyelet 7345 positions may optimise the directions and magnitudes of forces applied to the patient interface 3300 by the rear strap 3310.

In some forms, the positioning and stabilising structure 3300 may comprise the insert member 7387 with the eyelet 7345 disposed on only one side of the positioning and stabilising structure. The opposing side of the positioning and stabilising structure 3300 may comprise a single insert member (e.g. an insert member like the insert member 7387 of FIG. 20A) extending from cushion assembly 3150 to upper end of insert 7387.

The single insert member (not shown) may incorporate, or e.g. be integrally formed with, an adjustment mechanism (e.g. an adjustment mechanism like the adjustment mechanism 3360 of FIG. 20A).

In some embodiments, one or more insert members 7387 may be attached to tube portion 3350 to alter the length of the hoop. For example, an insert member without an eyelet (not shown) is removably coupled to the insert member 7387 with an eyelet 7345. The insert member without the eyelet may be placed either at the superior end or the inferior end of insert member 7387 depending on which would result in an optimised location of the eyelet 7345 i.e. optimised for comfort and/or seal. The insert member without an eyelet may have different lengths (e.g., similar to the insert members 7387a, 7387b and 7387c). The insert member without an eyelet may be mixed and matched with the insert members 7387 with an eyelet 7345 (e.g., a small insert member 7387a may be used with a small, medium, or large insert member that does not include an eyelet).

Referring now to FIGS. 21A-1 to 21B. In a further embodiment, a positioning and stabilising structure 3300 comprises an insert member 8387 positioned, in use, on top of the patient's head (e.g., superior to the patient's otobasion superior) wherein the insert includes couplings 8345.

In this further form, the insert member 8387 forms a part of a hoop that passes over the top of the patient's head. The hoop incorporates the insert member 8387, the tubes 3350 and the cushion assembly 3150. In use, portions of the insert member 8387 extend across the patient's crown regions (e.g., overlaying the patient's frontal bone and/or parietal bones at a superior region of the patient's head).

The insert member 8387 comprises a U-shaped tube that has three ports so that the insert member 8387, in use, fluidly connects to a respective end of each of tubes 3350 and the air delivery tube 4170 (not shown). For example, a central port 8602 in the upper side of insert member 8387 is configured to connect to connection port 3600 (not shown) or comprise connection port 3600.

The insert member 8387 may be configured to be selectably connected to the tube 3350 which allows a user to alter the actual length of the tube by selecting an insert member 8387 of a particular length. Insert member 8387 can be removed from the positioning and stabilising structure 3300 and replaced with a replacement insert member having a different length to the first insert member as depicted by the dotted lines in FIGS. 21A-1 and 21A-3. Any number of replacement insert members may be provided, where each insert member may be a different length and may be marked with a size indication (e.g., small, medium, or large). For example, a large insert member 8387 may have tube sections extending outwards from central port 8602 by a larger distance when compared to the length of tube sections extending outwards from the central port of a medium or small sized insert member 8387, as depicted by length L on FIG. 21A-3.

The insert member 8387 comprises couplings 8345 in the form of eyelets at the terminal end of protrusions 8604. The protrusions 8604 extend downwards (e.g., in an inferior direction) from both lower sides 8606 of the insert member 8387. In some forms, protrusion 8604 and eyelet 8345 are disposed on one lower side 8606 of the insert member. The protrusions 8604 extend downwards from a posterior side of the insert member 8387. The eyelet 8345 projects outwardly from each protrusion 8604 in a generally posterior direction.

The eyelet 8345 can be removably attached to the tubes 3350, for example by using a hook-and-loop fastening material or fasteners. A portion of hook-and-loop fastening material may be provided to an eyelet tab 8608 of the eyelet 8345. A complementary portion of the hook-and-loop fastener material may be provided to a corresponding eyelet tab (not shown) of the tube 3350 to secure the eyelet to the tube. In any example of the insert member 8387 (e.g., small, medium, or large), the eyelet 8345 may be removably attached to the respective tube 3350 superior to the otobasion superior (e.g., so that a strap connected to the eyelet 8345 may pass above the patient's ear).

The protrusions 8604 extend downwards from the lower sides 8606 of the insert member by a distance corresponding to the length of insert member 8387. For example, a large insert member 8387 may have protrusions 8604 extending downwards by a larger distance when compared to the length of protrusions 8604 extending from a medium or small sized insert member 8387.

Advantageously, corresponding the eyelet position with the insert member length can optimise the fit of the positioning and stabilising structure 3300 around different head shapes and sizes. The different eyelet position for each length of insert 8387 ensures both the eyelet 8345 and the rear strap 3310 (not shown) are optimally positioned relative to the patient's ear. Further, the corresponding insert lengths and eyelet positions may optimise the directions and magnitudes of forces applied to the patient interface 3300 by the rear strap 3310.

8.3.3.3.4 Cuttable Tubes

In another embodiment of the present technology, the tubes 3350 may be cut to the desired length. To assist the patient or clinician to determine where to cut the tubes 3350, the tubes may comprise one or more indicators indicating where to cut the tube for fitting the patient interface to different sizes heads. For example, lines or perforations may be provided around the diameter of the tubes 3350 to indicate where they may be cut. Each line or perforation may be marked with a size marking, for example 'small', 'medium' or 'large'. The cut markings on tubes 3350 may be provided on the lower ends of the tubes configured to connect to the cushion assembly 3150 or on the upper ends of the tubes configured to connect to the connection port 3600.

In one embodiment, a patient interface is supplied with a cutting tool configured to cut tubes 3350.

One disadvantage of cutting tubes 3350 to tailor the size of the patient interface is that, if the tubes are mistakenly cut too short, the cut off sections of tube may be difficult to replace.

8.3.3.3.5 Stretchable Tubes

In certain forms of the present technology the adjustment mechanism comprises one or more stretchable sections 3355 of headgear tubes 3350 formed of a stretchable material. Stretchable sections allow the length of tubes 3350 to be adjusted continuously to fit different sizes of patient heads. It will be appreciated that a section of tube may be stretchable by virtue of the material it is made from (e.g. if it is made from stretchable material), its configuration (e.g. the concertina tube section 3362 shown in FIG. 3A is stretchable by virtue of its configuration), or both.

FIG. 13 illustrates a headgear tube 3350 having a relatively stretchable section of tube 3355 connected to one or more non- or less stretchable sections of tube 3354. A securing mechanism 3356 may be provided to hold the tube 3350 in position when the desired length is attained. Securing mechanism 3356 may comprise a first securing member 3357 mounted on a length of tube 3350 on one side of the stretchable section 3355 and a second securing member 3358 mounted to a length of tube 3350 on the other side of the stretchable section 3355. First and second securing members 3357 and 3358 are configured to connect together by any appropriate mechanism, for example an interlocking clip, magnet connection, hook-and-loop fasteners. One of the securing members 3358 may comprise a plurality of sites at which the other securing member 3357 may connect to it to allow the tube 3350 to be secured at the desired length.

In another embodiment no securing mechanism is provided and the length of the tube 3350 is achieved automatically by the elastic contraction of the stretchable section 3355.

The stretchable section of tube 3355 may comprise a section that is thinner than the less stretchable sections 3354. Alternatively or additionally the stretchable section of tube 3355 may comprise a section that is formed from a material that is softer and/or has a lower durometer rating than the less stretchable sections 3354.

In one embodiment a stretchable section of tube 3355 has a cross-sectional thickness that reduces along its length. For example, the cross-sectional thickness may reduce in stepped longitudinal sections. Alternatively, the cross-sectional thickness of the tube section 3355 may alternate between thicker and thinner longitudinal sections. The surface transition between sections of differing cross-sectional thickness may be smooth or abrupt. The regions of differing cross-sectional thickness may have different rigidities and/or durometer ratings. The regions of differing cross-sectional thickness may be formed from the same or different materials. By selecting the structure of the stretchable section of tube 3355 using different materials and different cross-section thicknesses, specific sections of tube 3350 may be designed to stretch more than others. This may help the patient interface to fit differing patients by enabling parts of the tube 3350 that, in use, are positioned over parts of patients' anatomy that have particularly differing sizes between individuals to be made to stretch more than other parts. In addition, or alternatively, the stretchable section of tube 3355 may be designed to, in use, substantially maintain a pre-determined minimum aperture area so that the impedance of the patient interface to the flow of breathable gas can be configured to suit the respiratory treatment system, for example the desired rate of flow of gas.

8.3.3.3.6 Different Tube Connection Positions

In certain forms of the present technology, the tubes 3350 are able to be connected in a plurality of ways which enables the effective length of the fluid path between the connection port 3600 and the seal-forming structure 3100 to be adjusted.

In certain forms, each tube 3350 comprises two or more separate tube members able to be fluidly connected together at multiple positions to alter the length of the fluid path formed by the tube members. In one form, a first tube member comprises a plurality of ports along a side and a second tube member comprises one or more tubes protruding from a side of the second tube member and able to mate with selected ports in the first tube member to fluidly connect the first and second tube members. The length of the tube 3350 formed by the first and second tube members may be adjusted by selection of which ports the protruding tubes on the second tube member is connected to. The ends of the first and second tubes members adjacent to the connecting ports and protruding tubes are sealed so breathable gas passes only through each tube member and does not intentionally leak. Also the ports on the side of the first tube member may be provided with automatically closing valves to avoid leakage of gas if those ports are not connected to the second tube member.

In some forms of the technology, multiple tube connections are provided at the connection port and/or at the cushion assembly 3150. For example, the plenum chamber 3200 may comprise two or more ports on each side to which the tubes 3350 may selectively be fluidly connected. The ports may be arranged such that adjustment of which port the tubes are connected to alters the size of patient the patient interface fits. For example one port may be positioned so that, in use, it is closer to the patient's face than another port. Connection of the tube 3350 to a port closer the patient's face will accommodate a larger patient head than connection of the tube 3350 to a port further from the patient's face.

8.3.3.3.7 Alteration of Patient Interface Loop

Certain forms of the present technology comprise a patient interface 3000 in which the positioning and stabilising structure 3300 defines a loop configured to, in use, encircle a part of the patient's head. For example one or more ties may define a loop that encircles part of the patient's head in some forms of the technology. For example, in the embodiment shown in FIG. 3A, the loop is defined by the tubes 3350 and the cushion assembly 3150. These components create a loop within which the patient's head is positioned when the patient interface 3000 is being worn.

In some forms of the present technology the positioning and stabilising structure between the connection port 3600 and the seal-forming structure 3100 of cushion assembly 3150 is adjusted by an adjustment in the size of this loop. Adjustment of this loop enables the patient interface to be tailored to fit different sized patients. Previously described embodiments show how the size of the loop may be adjusted by alteration of the length of the tubes 3350. There will now be described embodiments in which other mechanisms for adjusting the size of the loop are provided.

8.3.3.3.8 Loop Adjustment Mechanisms

In certain forms of the present technology, the patient interface 3000 comprises a loop adjustment mechanism that is operable to adjust the position at which two regions of the positioning and stabilising structure 3300 are held together to adjust the size of the loop.

In FIG. 5, the patient interface 3000 comprises a strap 3390 connected between the tubes 3350. The strap 3390 is positioned towards an upper end of the patient interface 3000 below connection port 3600 such that, in use, it passes over the top of the patient's head, or proximate thereto. The strap 3390 may be upwardly curving to accommodate the top of the patient's head. The strap 3390 may be formed of a flexible, rigid or semi-rigid material.

In this embodiment, a loop of the patient interface 3000 that encircles a part of the patient's head when the patient interface 3000 is worn is defined by the strap 3390, the cushion assembly 3150 and the parts of tubes 3350 connected between strap 3390 and cushion assembly 3150. The size of this loop may be adjusted by adjusting the strap. The patient interface comprises a strap adjustment mechanism 3391 by which the length of the strap 3390 may be adjusted. Strap adjustment mechanism 3391 may comprise an adjustable fastening attachment between two sections of the strap 3390. For example, one section of the strap 3390 may pass through a loop attached to the end of the other section of the strap 3390 and attach to itself using a hook-and-loop material. Alternatively, the two strap sections may be able to be connected together using poppers or interlocking members that can connect in a plurality of different positions. In another embodiment, two sections of strap 3390 each comprise rack portions which engage with a pinion or cog and the length of the strap 3390 can be adjusted by rotation of the cog. In another embodiment, the two sections of the strap 3390 are telescopically slideable relative to each other and may be secured in place via an interlocking mechanism, magnets or frictional engagement.

In further alternative embodiments, one or both ends of the strap 3390 may connect to the tubes 3350 by an adjustable strap connection mechanism such that the position at which the strap 3390 connects to one or both tubes 3350 can be varied.

Another form of the technology is shown in FIG. 14. In this form, patient interface 3000 comprises a band 3395 positioned around the upper ends of the tubes 3350, i.e. the ends of the tubes closest to the connection port 3600. Band 3395 holds the tubes 3350 together at their upper end and its position determines the size of the loop defined in part by the tubes 3350 which encircles a part of the patient's head when the patient interface 3000 is worn. During use, the band 3395 may be moved along the tubes 3395 to alter where the tubes 3350 are held together and thus alter the size of the loop defined by the patient interface 3000. Moving band 3395 along the tubes 3350 towards the connection port 3600 makes the size of the loop larger so the patient interface can fit a larger head.

Band 3395 may be secured tightly around tubes 3350 with a high level of friction between the band and the tubes so that it cannot easily slide upwards and loosen during use. For example, the band 3395 may be formed from rubber or other high friction material. The frictional force may not substantially compress the tubes, in order to continue to permit airflow while the band 3395 is tightened. Alternatively, the patient interface may comprise a mechanism to secure the band in position. For example, a plurality of ridges and/or protrusions may be provided on the outer edges of tubes 3350 and one or more detents may be provided on the inner surface of band 3395 to interlock with the ridges/protrusions of the tubes 3350 and secure the band in position. The detents may be disengaged from the ridges/protrusions by an appropriate mechanism to enable the band to be moved along the tubes 3350 when desired.

In another embodiment upper sections of the two tubes 3350 are secured together by a clasp locker or zip. For example, one row of teeth of the clasp locker may be mounted on one tube 3350 and another row of teeth of the clasp locker may be mounted on the other tube 3350. The slider is moveable between the rows of teeth to adjust the position at which the two tubes 3350 are held together to alter the size of the loop formed by the patient interface 3000 are thereby accommodate different patient head sizes. The slider may limit accidental movement so that the patient does not accidentally change the size of the loop.

8.3.3.3.8.1 Simultaneous Adjustment

In further alternative embodiments, the length of the headgear strap 3310 and the strap 3390 can be adjusted together, i.e. simultaneously, in a single operation to alter the size of the respective loops that encircle part of the patient's head and/or alter the position of the respective loops on the patient's head.

Referring to FIGS. 25A, 25B and 25C, a rear strap 7310, similar to the embodiment of the headgear strap 3310, defines a loop that passes behind the patient's head and between the tubes 3350 and the cushion assembly 3150. A front hoop 7390, similar to the embodiment of the strap 3390, defines a loop that passes over the top of the patient's head and incorporates the tubes 3350 and the cushion assembly 3150. Thus, the front hoop 7390 may include at least one gas delivery tube 3350. In use, the front hoop 7390 extends across the patient's cheek regions and is arranged to contact regions of the patient's head superior to an otobasion superior of the patient's head.

Both rear strap 7310 and front hoop 7390 may be simultaneously adjusted in a single operation by an adjustment mechanism 7391. The adjustment by the adjustment mechanism 7391 may be to alter the actual length of the strap 7310 and/or hoop 7390, adjust the effective length of either or both of those components, and/or the position of either or both of those components on the patient's face.

The adjustment mechanism 7391 may, in a single operation, simultaneously adjust the rear strap 7310 and front hoop 7390 to enable the positioning and stabilising structure 3300 to be tailored to fit different sized patients. In other words, the length of the hoop 7390 that passes over the top of the patient's head and the length of the rear strap 7310 that passes behind the patient's head can be adjusted at the same time. The adjustment mechanism 7391 may adjust the effective length of the rear strap 7310 and/or the effective length of the front hoop 7390 through a continuous range of lengths (e.g., an infinite number of adjustments).

Referring now to FIGS. 26A and 26B, a link member 7394 may form a portion of the front hoop 7390. For example, the link member 7394 may connect two gas delivery tubs 3350 of the front hoop 7390 together. The link member 7394 may extend between an upper portion or end 7410 and a lower portion or end 7411 of the gas delivery tubes 3350 so that only the lower ends 7411 form a portion of the front hoop 7390. The link member 7394 comprises the adjustment mechanism 7391, a first 7392 and second 7393 section of the front hoop 7390, and a first and second section rear strap 7310. The first and second section of the respective hoop and strap may be connected at opposing regions 7396 of the headgear tubing 3350. The location of the opposing regions 7396 may be chosen to enable optimal sizing of the patient interface.

In one form, the first section 7392 of respective hoop and strap may pass through the link member 7394 attached to the end of the second section 7393 of respective hoop and strap. Referring to FIGS. 26A and 26B, the first 7392 and second 7393 sections of respective hoops and straps each comprise rack portions. The link member 7394 may take the form of a pinion or cog, wherein the first 7392 and second 7393 sections of respective hoops and straps each engage with the pinion or cog. The length of the front hoop 7390 and rear strap 7310 can be adjusted by rotation of the cog, which may enable the positioning and stabilising structure 3300 to be tailored to fit different sized patients.

In alternative forms, the adjustment mechanism may take the form of an eyelet. In this form, the link member 7394 may comprise a first section 7392 and second section 7393 of respective hoops and straps connected about the eyelet. The eyelet may be attached to the end of the second section 7393 of respective hoops and straps. The first section 7392 of respective hoops and straps may pass, e.g. thread, through the eyelet and attach to itself using a hook-and-loop material.

In further alternative forms, link member 7394 may comprise the first and second hoop and strap sections connected together using poppers or interlocking members that can connect in a plurality of different positions.

In some further embodiments, the adjustment mechanism 7391 may take the form of a dial control, a drawstring, and/or an electronic control unit.

The link member 7394 may operate by adjusting of the actual length of the link between the first 7392 and second 7393 sections of respective hoops and straps. Moreover, adjusting the length of the link does not change the length of the headgear tubing 3350. However, it does adjust the effective length of the tubing 3350 as it draws the sections of the tubing into closer proximity or allows them to be further apart. For example, increasing the length of the link may increase the distance between opposing regions 7396 of headgear tubing 3350 and in turn, increase the effective length of the front hoop 7390 configured to encircle the front part of the patients' head. Similarly, increasing the distance between opposing regions 7396 of headgear tubing 3350 may increase the actual length of the rear strap 7310 configured to encircle the front part of the patients' head as the link 7394 forms part of the rear strap.

Referring now to FIGS. 25A, 25B and 25C. In some forms the adjustment mechanism 7391 can be a releasable mechanical coupling, such as a dial control to allow tensioning and release of cables. The dial control may be connected to cables inserted through regions of the rear strap 7310 and the front hoop 7390. The length of the cables may be shortened by winding the dial control in one direction and lengthened by winding the dial control in an opposing direction. In some forms, the length of the cables inserted through regions of the rear strap 7310 and the front hoop 7390 can be changed at equal rates upon winding of the dial control. Alternatively, the length of the cables can be adjusted at different rates upon winding of the dial control, so as to shorten one cable more than the other cable. Such adjustments may be required for force vector optimisation.

Referring now to FIG. 27A. In some other forms, the adjustment mechanism 7391 can be a drawstring 7399 (e.g., which may be formed from a cable). In this form, the drawstring 7399 may be configured along the perimeter of both the front hoop and the perimeter of the rear strap 7310. In variations of this form, the drawstring 7399 of the front hoop 7390 may be configured along the entire perimeter of the front hoop 7390 or limited to pass along a portion that passes over the top of the patient's head. Pulling or releasing of the drawstring 7399 can simultaneously adjust the effective length of the front hoop 7390 and the rear strap 7310. Further, pulling or releasing of a drawstring 7399 can draw together or release sections of the front hoop 7390 and rear strap 7310 so as to adjust the length of the link 7394.

The drawstring 7399 may be inserted through a drawstring locking mechanism 7400. The drawstring locking mechanism 7400 may be deployed on the drawstring 7399 to secure the drawstring 7399 in position following adjustments in the drawstring length. The drawstring locking mechanism 7400 may have an opening to insert, e.g. thread, the drawstring 7399 through the front hoop 7390 and/or the rear strap 7310. The diameter of the opening may be smaller than the diameter of the drawstring such that frictional force secures the drawstring 7399 in position.

In some forms, a diameter of the opening may be adjustable. For example, a smaller diameter may provide the frictional force to secure the drawstring 7399 in position, while a larger diameter may allow the drawstring 7399 to more freely move through the opening. The drawstring locking mechanism 7400 may include a release button 7401, which may control the size of the opening. The opening may normally have the smaller diameter. The patient may pull the drawstring 7399 through the opening, but the frictional force may limit the drawstring 7399 from returning through the opening. The patient may engage the release button 7401 in order to expand the diameter of the opening to a position where it no longer applies a frictional force to the drawstring 7399. The drawstring 7399 may be biased into the opening, and may automatically retract once the patient engages the release button 7401. This may allow the patient to quickly adjust (e.g., increase or decrease) an exposed length of the drawstring 7399.

In some forms, the mechanical components of the adjustment mechanisms described in this disclosure can be controlled electronically. For example, a rack and pinion arrangement may be automatically moved or a cable may be automatically tightened or loosened. Referring to FIG. 28, a control unit 7402 can be disposed on a part of the tubing 3350 as to enable the sizing of the patient interface to the controlled. The control unit may be operated directly, by use of buttons on the control unit. Alternatively, the control unit may be operated remotely by, i.e. a mobile phone software application 7404, which may be connected to the control unit 7402 by Bluetooth, Wi-Fi, radio waves, or any similar form of wireless communication.

Referring now to FIGS. 25A, 25B and 25C. In some forms, the front hoop 7390 and rear strap 7310 of the positioning and stabilising structure 3300 may be applied to an UCFF mask system. In this arrangement, two or more straps, e.g. rear strap 7310 and chin strap 7320 may attach to at least one of the headgear tubes 3350 and the UCFF cushion assembly 3150. The adjustment mechanism 7391 may be operated to adjust the effective length of the front hoop 7390 and rear strap 7310 in the UCFF system, and therefore adjust the respective force vectors of the positioning and stabilising structure 3300.

Now referring to FIG. 29, the link may form part of the rear strap 7310. In this form, the rear strap 7310 may be adjusted in a single operation to simultaneously adjust the length of the front hoop 7390 and rear strap 7310.

In some forms, the adjustment mechanism may form part of the rear strap. Referring now to FIG. 29, the adjustment mechanism 7391 may take the form of an end of strap 7310. The rear strap 7310 may be configured such that the end is threaded through a hole in the tab 7345 and projects in a generally posterior direction. The adjustment mechanism 7391 at the end of the strap 7310 attaches to itself using a hook-and-loop material, or a similar means of connection (e.g., snaps, magnets, etc.). The adjustment mechanism 7391, in some forms, may be disposed on one side of the patient's head and enable simultaneous adjustment of the rear strap 7310 and the front hoop 7390. The rear strap 7310 and the front hoop 7390 move relative to one another so as to adjust the effective length and/or positioning of the front hoop and rear strap configured to encircle a part of the patient's head.

The adjustment mechanism 7391 at the end of rear strap 7310 may be connected to cables 7406 inserted through regions of the rear strap 7310 and the front hoop 7390. The length of the cables may be adjusted by pulling more or less of the rear strap 7310 through the tab 7345. The end of the rear strap 7391 may be secured to itself after passing through the tab 7345.

In some forms, the length of the rear strap 7310 and the front hoop 7390 can be changed at equal rates upon pulling the adjustment mechanism 7391 through the tab 7345. In alternative forms, the length of the rear strap 7310 and the front hoop 7390 can be adjusted at different rates upon pulling the adjustment mechanism 7391 at the end of rear strap 7310 through the tab 7345, so as to shorten one strap more than the other. This type of adjustment may be required for force vector optimisation.

Another form of the technology is shown in FIG. 14. In this form, patient interface 3000 comprises a band 3395 positioned around the upper ends of the tubes 3350, i.e. the ends of the tubes closest to the connection port 3600. Band 3395 holds the tubes 3350 together at their upper end and its position determines the size of the loop defined in part by the tubes 3350 which encircles a part of the patient's head when the patient interface 3000 is worn. During use the band 3395 may be moved along the tubes 3395 to alter where the tubes 3350 are held together and thus alter the size of the loop defined by the patient interface 3000. Moving band 3395 along the tubes 3350 towards the connection port 3600 makes the size of the loop larger so the patient interface can fit a larger head.

Band 3395 may be secured tightly around tubes 3350 with a high level of friction between the band and the tubes so that it cannot easily slide upwards and loosen during use. For example, the band 3395 may be formed from rubber or other high friction material. Alternatively, the patient interface may comprise a mechanism to secure the band in position. For example, a plurality of ridges and/or protrusions may be provided on the outer edges of tubes 3350 and one or more detents may be provided on the inner surface of band 3395 to interlock with the ridges/protrusions of the tubes 3350 and secure the band in position. The detents may be disengaged from the ridges/protrusions by an appropriate mechanism to enable the band to be moved along the tubes 3350 when desired.

In another embodiment upper sections of the two tubes 3350 are secured together by a clasp locker or zip. For example, one row of teeth of the clasp locker may be mounted on one tube 3350 and another row of teeth of the clasp locker may be mounted on the other tube 3350. The slider is moveable between the rows of teeth to adjust the position at which the two tubes 3350 are held together to alter the size of the loop formed by the patient interface 3000 are thereby accommodate different patient head sizes.

The upper ends of the tubes 3350 as shown in FIG. 14 form a y-shaped arrangement, i.e. two tubes converge into a single tube. Accordingly, the connection port may take the form of a y-shaped or v-shaped connection port 3600. Referring now to FIGS. 26A and 26B. Advantageously, the y-shaped arrangement can provide improved laminar airflow into and through the headgear tubing 3350, compared to the flow through previously described arrangements of the patient interface 3000, wherein a swivel elbow is connected at the connection port 3600 and oriented at 90 degrees to the headgear tubing.

In some forms, the positioning and stabilising structure 3300 may include a de-coupling mechanism 7600 to decouple positional adjustment of a conduit of an air circuit 4170 (e.g., structure conveying pressurized air from the RPT device 4000 to the patient interface 3000) from movement of the seal-forming structure 3100 away from the patient's face in use to enable positional adjustment of the conduit of the air circuit 4170. In some forms, the de-coupling mechanism 7600 may decouple positional adjustment of at least a portion of the gas delivery tubes 3350 from movement of the seal-forming structure 3100 away from the patient's face in use to enable positional adjustment of the conduit of the air circuit 4170 and/or the gas delivery tubes 3350 on the patient's head. In some forms, the de-coupling structure 7600 may include a y-shaped (or v-shaped) arrangement. A tube connector 7407 may partially form the y-shaped or v-shaped arrangement by connecting each gas delivery tube 3350 to a single body. Upper ends 7410 of the gas delivery tubes 3350 may be connected to the tube connector 7407. In some forms, the de-coupling structure 7600 is biased toward the rear of the patient's head, in use. In other forms, the de-coupling structure 7600 may be elastically flexible to allow the conduit to move freely between a rearward, sideward and forward position of the patient's head.

Referring to FIGS. 30A to 32, in one form of this embodiment, the decoupling mechanism 7600 may include a swivel joint 7408. The swivel joint 7408 may include a first end connected to the tube connector 7407. In this form, the upper portions or ends 7410 of the tubes 3350 converge into one end of the tube connector 7407 and the swivel joint 7408 extends from the opposite end of the tube connector 7407 in order to form the y-shaped (or v-shaped) arrangement. In some forms, the swivel joint 7408 may be a swivel elbow, and may include a bend (e.g., a 90° bend). In some forms, the swivel joint 7408 may be constructed from a flexible material (e.g., the same material as the tubes 3350). In some forms, the swivel joint 7408 may be constructed from a rigid or semi-rigid material.

The swivel joint 7408 may include a first end that is directly coupled to the tube connector 7407 (although the first end may be connected directly to at least one of the gas delivery tubes 3350). The swivel joint 7408 also includes a second end opposite to the first end, which functions as a connection port 3600. In other words, a conduit of the air circuit 4170 may be directly connected to the second end of the swivel joint 7408.

The swivel joint 7408 and the flexible upper ends 7410 of the gas delivery tubes 3350 function together as the de-coupling mechanism. In other words, the de-coupling mechanism 7600 includes the swivel joint 7408, the tube connector 7407, and the upper ends 7410 of the tubes 3350. Advantageously, the swivel joint 7408 of de-coupling mechanism 7600 allows the air circuit 4170 to move relative to the seal forming structure 3100 of the patient interface 3000. Specifically, the swivel joint 7408 may rotate relative to the tube connector 7407 so that the rotation of the swivel joint 7408 does not twist the upper ends 7410 of the tubes 3350. The swivel joint 7408 enables positional adjustment of the conduit of the air circuit 4170 and may reduce the risk of destabilising the seal of the seal forming structure 3100 against the patient's face.

The de-coupling structure 7600 may also allow the upper ends 7410 of the gas delivery tubes 3350 to move with respect to the remainder of the gas delivery tubes 3350. For example, the upper ends 7410 of the tubes 3350 may be corrugated or include concertina sections, which may allow the upper ends 7410 to bend (i.e., the upper ends 7410 may be bendable). This may provide additional degrees of freedom to the de-coupling structure 7600 as a whole, and may allow for movement of the upper ends 7410 of the gas delivery tubes 3350 with respect to the lower ends of the gas delivery tubes 3350 without interfering with the seal of the seal forming structure 3100.

Referring now to FIGS. 30A and 30B. In some forms, the de-coupling structure 7600 comprises the swivel joint 7408 configured to rotate about a single axis 7412. In this form, the swivel joint 7408 may be configured to rotate about the single axis parallel to the axes 7413 of the tubes 3350 (e.g., unbent portion of the upper ends 7410 as illustrated in FIG. 30A) connected to the decoupling structure 7600.

In some forms, the upper ends 7410 may be bent relative to the remainder of the respective tubes 3350 at least partially because of the weight of the swivel joint 7408.

Referring now to FIGS. 31A, 31B, 32A and 32B. In some other forms, the decoupling structure 8600 comprises multiple swivel joints arranged as a subassembly of components configured to rotate about more than one axis.

Referring to FIGS. 31A and 31B, the swivel joint 8408 includes a first swivel 8415 and a second swivel 8416. The first swivel 8415 may be directly connected to the tube connector 8407, and may rotate about a first axis of rotation 8414 oriented perpendicular to the axes 8413 of the upper ends 8410 of the tubes 3350 (e.g., unbent tubes 3350 as illustrated in FIG. 31A). The second swivel 8416 may be connected adjacent to the first swivel 8415 and may provide a second axis of rotation 8412. The second axis of rotation 8412 may be oriented perpendicular to the first axis of rotation 8414. The second axis of rotation 8412 may also be oriented parallel to the axis of the tubes 3350 (e.g., unbent portion of the upper ends 8410 as illustrated in FIG. 31A). The first swivel 8415 and the second swivel 8416 may be rotatable simultaneously and/or independently of one another.

Referring to FIGS. 32A and 32B, further variations of a de-coupling structure 9600 may comprise a swivel joint 9408 with two axis of rotation. A first swivel 9415 of the swivel joint 9408 may be connected directly to a tube connector 9407, and may be configured to rotate about a first axis of rotation 9414 parallel to the axes 9413 along the tubes 3350 (e.g., unbent portions of the upper ends 9411 as illustrated in FIG. 32A). A second swivel 9416 of the swivel joint 9408 may be connected adjacent to the first swivel 9415 and may provide a second axis of rotation 9412 perpendicular to the first axis of rotation 9414. The second axis of rotation 9412 may also be oriented perpendicular to the axes 9413 of the tubes 3350 (e.g., unbent portions of the upper ends 9411 as illustrated in FIG. 32A). The first swivel 9415 and the second swivel 9416 may be rotatable simultaneously and/or independently of one another.

The swivel joint 8408, 9408 of both the de-coupling structure 8600 and the de-coupling structure 9600 include two degrees of rotational freedom. A difference between the two de-coupling structures 8600, 9600 relates to which axis is adjacent to the upper ends 9411. This, in turn, may determine a direction that the pressurized air flows into the de-coupling structure 8600, 9600. For example, the axis of rotation 8414 is the perpendicular axis, so a conduit conveying the pressurized air to the de-coupling structure 8600 may extend substantially horizontally from the de-coupling structure 8600. The opposite may be true in the de-coupling structure 9600, where the conduit may extend substantially vertically. A patient may desire one de-coupling structure 8600, 9600 over the other based on preferred sleeping positions.

As best shown in FIG. 25A, the adjustment mechanism 7391 may be located proximal to the patient's crown and forward (i.e., more anterior than) of the y-shaped decoupling structure 7600. The conduit connected to the y-shaped decoupling structure 7600 (e.g., at the second end of the swivel joint 7408) may extend rearward of the adjustment mechanism 7391 in order to not cover, or otherwise obstruct, the adjustment mechanism 7391. This may provide the patient with easy access to the adjustment mechanism 7391 without interference from the y-shaped connection port 7600. In alternative embodiments not shown, the adjustment mechanism 7391 may be located at, or rearward, of the y-shaped connection port 7600.

Referring now to FIGS. 26A and 26B. In some forms, the upper ends 7410 of the two tubes 3350 are secured together by an adjustment mechanism 7391. The adjustment mechanism 7391 may be located over the crown (e.g., overlaying the frontal bone and/or the parietal bones of the patient), primarily forward of the converging y-shaped junction.

In some forms, the adjustment mechanism 7391 may adjust the length of the front hoop 7390. A separate, rear strap 7310 similar to the embodiment of the headgear strap 3310, may be positioned behind the patient's head and between the tubes 3350. The adjustment mechanism 7391 and rear strap 7310 may be independently operable to adjust the positioning and stabilising structure 3300 to fit different sized patients.

In some forms, the adjustment mechanism 7391 may, in a single operation, simultaneously adjust the front hoop 7390 and the rear strap 7310 to enable the positioning and stabilising structure 3300 to be tailored to fit different sized patients. In this form, both the hoop that passes over the top of the patient's head and the length of the rear strap that passes behind the patient's head can be adjusted at the same time.

The adjustment mechanism 7391 may hold the tubes 3350 together at their upper section and determine the size of the hoop defined in part by the tubes 3350 which encircles a part of the patient's head when the patient interface 3000 is worn.

Referring now to FIGS. 26A and 26B, the adjustment mechanism 7391 may comprise a link member 7394 between a first 7392 and second 7393 section of the front hoop 7390 and rear strap 7310. As previously described for alternative embodiments of simultaneous adjustment, the link member 7394 may operate by adjusting of the length of the link between the first 7392 and second 7393 hoop and strap sections.

Referring now to FIGS. 26A and 26B. The link member 7394 may be adjusted to different lengths to alter the length of the link between opposing regions 7396 of headgear tubing 3350. Increasing the length of the link member 7394 allows the positioning and stabilising structure 3300 to fit a larger head. Conversely, reducing the length of the link member 7394 allows the positioning and stabilising structure to fit a smaller head.

The front hoop 7390, in some forms, can comprise a textile element. In alternative embodiments, the front hoop can be wholly textile. Referring to FIGS. 27B-1 and 27B-2, the link member 7394 may comprise the first and second sections 7292, 7293 as a textile strap, and an adjustment mechanism disposed therebetween. The first and second sections may be connected together by the adjustment mechanism in the form of a locking mechanism 8400. Referring to FIGS. 27B-1 and 27B-2, the locking mechanism 8400 may comprise an opening wherein the first and second sections 7392, 7393 of the strap are inserted through the opening. The opening may be configured to secure the strap following adjustments in the strap length. The diameter of the opening may be smaller than the diameter of the straps such that frictional force secures the straps in a set position.

8.3.3.3.9 Loop Inserts

In certain forms of the present technology, the positioning and stabilising structure 3300 comprises one or more loop insert members configured to be secured to another part of the patient interface 3000, for example directly or indirectly secured to the tubes 3350. The loop insert member(s) is configured to be secured so that it defines, at least in part, the loop which, in use, encircles part of the patient's head. By adjusting the size of the loop insert member, or by replacing the loop insert member with a loop insert member of a differing size, the size of the loop can be adjusted to accommodate different sizes of patient heads.

One form of the present technology is shown in FIG. 15. In this form, patient interface 3000 comprises a loop insert member 3410 that is connected to the underside of tubes 3350 and connection port 3600 and, in use, is positioned between the patient's head and the tubes 3350 and connection port 3600. Loop insert member 3410 acts to change the size of the loop that encircles a part of the patient's head compared to the size of the loop formed by the tubes 3350 if the loop insert member is not present.

Loop insert member 3410 is removably attached to tubes 3350. Loop insert member 3410 may therefore be removed and replaced by one or more replacement loop insert members 3411a, 3411b or 3411c. Replacement loop insert members 3411a, 3411b or 3411c differ in size from loop insert member 3410 and by selection of the loop insert members the size of the loop for encircling a part of the patient's head can be adjusted and consequently the patient interface can be adapted to fit the patient more comfortably and more securely. The ability to remove the loop insert members 3410 and 3411 is also beneficial so that they can be cleaned.

Loop insert members may be formed from a rigid or semi-rigid material able to space the tubes 3350 from the patient's head in use and thereby alter the shape of the loop encircling the patient's head. A material that has some resilience and give may provide more comfort when worn, for example a foam or gel material. Since the loop insert members are in contact with the patient's hair or skin when worn they are preferably made from a material that is easily cleaned.

The loop insert members 3410 and 3411 shown in FIG. 15 are generally U-shaped with the apex of the 'U' positioned in use at the top of the patient's head below the connection port 3600. This helps the patient interface to conform to the shape of the top of the patient's head. In other embodiments, different shaped insert members are used, for example an insert member may comprise a short straight pad configured to contact a small part of the patient's head. Different sized replacement insert members 3411 may have different thicknesses, different lengths, and/or different degrees of curvature. The patient contacting surface of each insert member may be the same or similar to conform to the patient's head shape irrespective of which insert member is used.

The loop insert members 3410 and 3411 are attached to the tubes 3350 by a fastening mechanism. In one embodiment the fastening mechanism comprises hook-and-loop material attached to the underside of tubes 3350 and the upper side of loop insert members 3410 and 3411. In other embodiments, poppers, domes, clasp lockers or magnets are used to connect loop insert members 3410 and 3411 to the tubes 3350.

In the embodiment of FIG. 15 the patient interface 3000 comprises a single loop insert member 3410 and the replacement loop insert members 3411 are single or monolithic components. In other embodiments, multiple loop insert members are able to be attached to the tubes 3350 at any one time. For example, multiple loop insert members may be able to be attached along the length of tubes 3350 to act as a plurality of spacers spacing different parts of the patient's head from the tubes 3350. In another embodiment, multiple of the loop insert members 3410 and the replacement loop insert members 3411 may be mounted on the tubes 3350 at any one time. For example, different sized loop insert members may be able to be nested. To achieve this, the loop insert members 3410 and 3411 may be able to connect to each other, for example using any of the loop insert member connection mechanisms mentioned above.

In further embodiment of FIG. 15, a pocket or pouch may be connected to, or formed in, a side of the tubes 3350. The pocket may be made from a material which is preferably elastic to enable easy insertion of an insert member 3410 into the pocket e.g. a textile or silicon. In this form, the insert member 3410 may be made from a rigid material, e.g. Hytrel, wherein distal ends of the member are inserted within the pocket. In this embodiment, the rigid material is selectably inserted into the pocket to adjust the overall elasticity of the positioning and stabilising structure 3300. For example, a section of the tube 3350 is stretchy and a rigid insert member 3410 may be used to maintain a predetermined amount of stretch within a section of the tube 3350.

In a further embodiment shown in FIG. 22, the positioning and stabilising structure 3300 may comprise an adjustment mechanism in the form of an insert member 9410 used in combination with a stretchable tube 9350.

In this further embodiment, the insert member 9410 forms a section of a hoop defined by a loop that passes over the top of the patient's head and incorporates the tubes 9350 and the cushion assembly 3150 (not shown). In use, the hoop extends across the patient's cheek regions and is arranged to contact regions of the patient's head superior to an otobasion superior of the patient's head.

In some forms, the insert member 9410 may be constructed from a rigid material (e.g., Hytrel). The stretchable tube 9350 may comprise one or more stretchable sections 9355 that are formed of a stretchable material. The section of tube may be stretchable by virtue of the material it is made from (e.g. if it is made from stretchable material), its configuration (e.g. the concertina tube section 3362 shown in FIG. 3A is stretchable by virtue of its configuration), or both.

The stretchable sections of tube 9355, in use, may be positioned at the top of the patient's head. The stretchable sections of tube 9355 may be connected to one or more relatively non-stretchable or less stretchable sections of tube 9354. In some forms, the stretchable sections of the tube 9355 and/or relatively non-stretchable or less stretchable sections or thin stretch sections of tube 9354, 9355 may be made from silicon. In some other forms, at least some sections of tube 9354 may be made from a textile material (e.g., spandex). In some other forms, a combination of materials, e.g. silicon and textile, may be used.

The insert member 9410 may be fastened to the tube 9350 by at least one retainer or first fastening member 9357 mounted on the underside of tube 9350 (e.g., on an exterior surface of the tube 9355) on both sides of the stretchable section 9355. For example, one first fastening member 9357 may be mounted on either end (e.g., a left end and a right end) of the stretchable section 9355 (e.g., proximate to the relatively non-stretchable or less stretchable sections 9354). The first fastening member 9357 may be exposed to the ambient while the positioning and stabilising structure 3300 is in use. A second fastening member 9358 can be mounted on both ends of an upper side of insert member 9410. First and second fastening members 9357 and 9358 are configured to connect together by any appropriate mechanism, for example hook-and-loop material. When mounted to the first fastening member 9357, the insert member 9410 may be exposed to the ambient and may contact a superior region of the patient's head (e.g., the insert member 9410 may overlay the frontal bone and/or the parietal bones).

The stretchable sections of tube 9355 allow the actual length of the tube 9350 to be altered when the rigid insert member 9410 is attached. The size of the hoop that encircles a part of the patient's head is changed corresponding to the length of insert 9410 attached when compared to the size of the hoop if the insert member is not present. By adjusting the size of the insert member, or by replacing the insert member with an insert of a differing size, the size of the hoop can be altered to accommodate different sizes of patient heads. In the embodiment shown in FIG. 22, three different length insert members 9410 may be selectably fastened to the tube 9350. Each different length of insert member 9410 is marked with a size indication, for example, 'S' for small (e.g., 9410*a*), 'M' for medium (e.g., 9410*b*), and 'L' for large (e.g., 9410*c*).

To attach the insert member 9410, the second fastening member 9358 on one end of the insert member 9410 may be connected to the first fastening member 9357 on one end of the stretchable section 9355. The insert member 9410 may be longer than the distance between the first fastening member 9357 on the other end of the stretchable section 9355. The patient may have to stretch the stretchable section 9355 in order to align and connect the first and second fastening members 9357, 9358. Once both second fastening members 9358 are connected to the respective first fastening members 9357, the stretchable section 9355 has increased in length (i.e., the stretchable section's length is greater than in a relaxed position). The total increase in length may be dependent on the specific insert member 9410 that the patient selected (e.g., small, medium, or large). The selected insert member 9410 may be positioned substantially symmetrically about the patient's sagittal plane.

Stretching the stretchable section 9355 before the positioning and stabilising structure 3300 is donned by the patient may assist in improving comfort of the patient. For example, a pre-stretch in the stretchable section 9355 (i.e., caused by attaching the insert member 9410) may limit a frictional force experienced by the patient of the stretchable section 9355 pulling the patient's hair and/or skin.

In some alternative forms of the example shown in FIG. 22, the insert member 9410 can be releasably fastened inside the tube 9350. In this example, the insert member can be inserted into the tube through the central port 9602 and fastened to the bottom wall of tube 9350 (e.g., an interior wall) by a fastening member such as hook-and-loop material (not shown). Therefore, the insert member 9410 is in the pressurized volume of the tube 9350 in use (e.g., as opposed to being exposed to the ambient). The insert member 9410 of FIG. 22 may be connected to the tube 9350 in a substantially similar manner as the insert member 9410 of FIG. 21 (e.g., the stretchable section 9355 may be pre-stretched before the positioning and stabilising structure 3300 is donned by the patient).

In the form of the present technology illustrated in FIG. 16 the patient interface 3000 comprises an inflatable loop insert member 3420. Inflatable loop insert member 3420 may comprise a bladder provided on an inner surface of tubes 3350. The bladder has a sealable opening into which air can be introduced or released to alter the size of the bladder and consequently adjust the size of the loop defined by the patient interface 3000 which encircles part of the patient's head in use. In one embodiment, the patient interface comprises a pump button which can be repeatedly depressed to introduce air into the bladder through a valve.

In the form shown in FIG. 16 the patient interface comprises a single U-shaped bladder 3420 that is connected to each tube 3350 on either side of and on top of the patient's head. The thickness of the bladder 3420 may be largest at the top of the patient's head to accommodate a symmetrical movement of the tubes 3350 away from the surface of the patient's head as the bladder is inflated. In other embodiments, multiple inflatable bladders are mounted on the tubes 3350. These inflatable bladders may be inflatable together or separately. Separately inflatable bladders allows a patient to alter the fit of the patient interface as desired, for example by inflating a bladder on one side of the head more than the other side.

In a further form of the present technology illustrated in FIGS. 23A and 23B the patient interface 3000 comprises an adjustment mechanism in the form of inflatable portions 10420. The inflatable portion 10420 forms a hoop defined by a loop that passes over the top of the patient's head and incorporates the tubes 3350 and the cushion assembly 3150. In use, the hoop extends across the patient's cheek regions and is arranged to contact regions of the patient's head superior to an otobasion superior of the patient's head.

In some forms, the inflatable portion 10420 is retained by a retainer disposed in a side of the gas delivery tubes 3350. In some forms, the retainer may be one or more fasteners (e.g., hook and loop material) fixed to the tubes 3350 wherein the inflatable portion 10420 is selectably coupled to the tubes 3350. Fasteners may be provided to each end of the inflatable portion 10420 to secure the inflatable portion 10420 to the tubes 3350. For example, fasteners may be disposed on a superior surface of the inflatable portion

10420, and may connect to an inferior surface of the gas delivery tubes 3350. The inflatable portion 10420 may contact a superior portion of the patient's head (e.g., in a position overlaying the frontal bone and/or the parietal bones) while the patient interface 3000 is worn by the patient. Alternative forms of the retainer may include a loop (not shown) which surrounds the tubes 3350.

In alternative forms, the inflatable portion 10420 may be fixed to the tubes 3350, e.g. integrally formed with the tubes.

In certain forms, the patient interface 3000 may include multiple inflatable portions 10420. For example, the inflatable portions 10420 may be separately connected (e.g., removably or integrally) with the gas delivery tubes 3350. Additionally, the inflatable portions may be inflated independently or at the same time.

The inner surface of tubes 3350 may comprise one or more inflatable portions 10420 in contact with the patient's head. The inflatable portion can adjust the position of the gas delivery tube on the patient's head and alter the effective length (e.g., an inner perimeter) of the hoop. Referring to FIG. 23A, an inflatable portion 10420 is shown in a deflated state, wherein the effective length of the hoop is at its maximum in order to accommodate larger patient head sizes and shapes. Referring to FIG. 23B, an inflatable portion 10420 is shown in an inflated state, wherein the effective length of the hoop is decreased (e.g., as compared to the inflated state) to accommodate smaller patient head sizes and shapes. In other words, the inflated state of the inflatable portion 10420 creates a smaller inner perimeter of the hoop. The inflatable portion 10420 expands toward a center of the hoop (e.g., toward the patient's head), and may be brought into contact with the patient's head. The inflatable portion 10420 may inflate a different amount depending on the individual patient's head. Thus, patients with smaller heads may require the inflatable portion 10420 inflated more than patients with larger heads. Altering the effective length of the hoop correspondingly alters the force vector applied to the patient's head by the positioning and stabilising structure 3300. Altering the effective length of the hoop may also alter the tensile forces experienced by the patient from the gas delivery tubes 3350. In other words, moving the inflatable portion 10420 into the inflated state may provide tighter contact between the inflatable portion 10420 and the patient's head, in order to limit translation along the patient's head (e.g., in the anterior-posterior direction).

In some forms of the present technology, the volume of air in the inflatable portion 10420 can be controlled by the patient. For example, a valve may be provided to the inflatable portion 10420 which allows a patient to provide air to inflate the inflatable portion 10420 or to remove air to deflate the inflatable portion 10420. Advantageously, allowing the patient to control the volume of air in the inflatable portion may provide a feeling of control to the patient. The patient may be able to don the patient interface 3000 and subsequently adjust the volume of air in the inflatable portion 10420 so that the inflatable portion 10420 is neither too tight nor too loose against the patient's head.

In some alternative forms, the inflatable portion 10420 may be inflated by an automatic means. The automatic means may comprise the inflatable portion and incorporate a gauge and one or more sensors that can detect the inflated pressure of the inflatable portion. As shown in FIG. 24, a patient may start the system 10500, and the controller may retrieve a stored pressure value 10505. A sensor may monitor the pressure in the inflatable portion 10510, and may communicate with a controller 10515 in order to control when to open and close the valve and adjust the pressure within the inflatable portion 10520.

In some forms, the patient may don the patient interface 3000, and the inflatable portion 10420 may inflate until the patient indicates that pressure within the inflatable portion 10420 is comfortable. The controller may store the set valve and inflate the inflatable portion 10420 to the same level each successive use by comparing the stored pressure valve with the pressure measured by the sensor.

In some forms, the sensor may be a light sensor and/or a position sensor, and may detect the proximity between the patient's head and the inflatable portion 10420 in order to determine how much the air should enter the inflatable portion 10420.

In some forms, the flow of pressurized breathable gas from the RPT device 4000 may be diverted into the inflatable portion 10420. The inflatable portion 10420 may include a conduit 10424 may be connected directly to the RPT device 4000, or may be connected to the gas delivery tubes 3350. An entrance valve (e.g., either automatically or manually adjustable) may selectively allow the pressurized breathable gas to enter the inflatable portion 10420. An exit valve may be selectively actuated in order to release the air from the inflatable portion 10420.

As shown in FIG. 24, a further embodiment of the alternative form includes the one or more sensors may be able to detect the occurrence of an apnea 10525. In the event a sensor detects an apnea 10525, the inflatable portions 10420 may automatically adjust 10530 the degree of inflation so as to alter the effective length of the hoop. Altering the effective length of the hoop during an apnea can optimise the direction and magnitude of forces applied to the positioning and stabilising structure 3300 and re-establish a secure fit and effect seal for the patient. The altered hoop length may reduce the occurrence of further apneas, and the controller may store a new set pressure value 10535 for the patient. The system may compare this new value 10515 with the current pressure sensed 10510 in the inflatable portion 10420. The system may then make a further pressure adjustment 10520 (e.g., if the values are unequal), or continue sensing for apneas 10525 (e.g., if the values are equal).

The inflatable portion 10420 can be made from textile material. In some forms, the inflatable portion 10420 may be made from silicon. In some other forms, a combination of materials, e.g. textile and silicon, may be used together to form the inflatable portion.

8.3.3.3.10 Magnitude of Dimensional Adjustment of Headgear Tubing

As discussed previously, the positioning and stabilising structure 3300 may be configured to be worn with the upper portion of the headgear tubing 3350 positioned differently for different patients. For example, the position of the connection port 3600 on the patient's head during use may vary within a range of forward/rearward positions in the sagittal plane. The circumference of a patient's head around which the headgear tubing 3350 fits may be smaller if the upper portion of the headgear tubing 3350 is worn further forward compared to if the headgear tubing 3350 was worn further back. In some forms, the positioning and stabilising structure 3300 allows a patient with a large head size to wear the upper portion of the headgear in a more forward (e.g. anterior) position on their head, reducing the magnitude of length adjustment that is needed from the adjustment mechanism 3360 to accommodate the large head size.

FIG. 3J shows three depictions of a patient interface 3000a, 3000b, 3000c according to one form of the technology, each depiction of the patient interface 3000 being shown in a different position on the patient's head, for comparison. The patient interface 3000b is shown in solid lines in a central position, while the patient interfaces 3000a and 3000c are shown in phantom and are worn forwardly and rearwardly, respectively. In each of the depictions in FIG. 3J, the adjustment mechanism 3360 has substantially the same length. That is, the adjustment mechanism 3360 is not extended or contracted between the depictions labelled "a", "b" and "c". While there is no change in length of the adjustment mechanism 3360, the patient interface 3000a (the forward position) can fit over a larger head (shown in phantom) since it is worn forward. Similarly, the patient interface 3000c (rearward position) can fit properly to a smaller head (shown in phantom) with the same length of adjustment mechanism 3360.

In one depiction in FIG. 3J, identified by reference numerals labelled "b", the patient is wearing the headgear in a central position, in which the adjustment mechanism 3360b and connection port 3600b are approximately aligned vertically (e.g., parallel to or co-planar with the coronal plane). The connection port 3600b is located centrally in the anterior-posterior axis. That is, the connection port 3600b is located in a central position rather than in a generally forward (e.g. anterior) position or a generally backward (e.g. posterior) position. The connection port 3600b is located approximately at a top point of the patient's head. The connection port 3600b may be positioned in the sagittal plane and aligned with the otobasion superior points in a plane parallel to the coronal plane. The otobasion superior points are identified in FIG. 2D.

In another depiction in FIG. 3J, identified by reference numerals labelled "a", the patient is wearing the headgear tubing 3350a in a relatively forward position compared to the position of headgear tubing 3350b (e.g., anterior to and inclined relative to the coronal plane). In this configuration, the connection port 3600a is positioned generally forward of the adjustment mechanism 3360a. In this position, the connection port 3600a is anterior to the otobasion superior points. In another depiction in FIG. 3J, identified by reference numerals labelled "c", the patient is wearing the headgear tubing 3350c in a relatively rearward position compared to the position of headgear tubing 3350b (e.g. posterior to and inclined relative to the coronal plane). In this configuration, the connection port 3600c is positioned generally rearward of adjustment mechanism 3360c. In this position, the connection port 3600c is posterior to the otobasion superior points.

When worn in the position depicted by headgear 3300a in FIG. 3J, the headgear tubing 3350a will generally fit around a smaller circumference of the patient's head, enabling the positioning and stabilising structure 3300 to be worn in a relatively forward position to accommodate a patient with a larger head (shown in phantom). Similarly, when worn in the position depicted by positioning and stabilising structure 3300c in FIG. 3J, the headgear tubing 3350c will generally fit around a larger circumference of the patient's head, enabling the positioning and stabilising structure 3300 to be worn in a relatively rearward position to accommodate a patient with a smaller head (shown in phantom). The positioning and stabilising structure 3300 may be worn in a continuous range of positions between a generally forward position and generally rearward position depending on the patient's head size, head shape, personal preference, among other factors. In some forms the present technology the positioning and stabilising structure 3300 is configured to be worn such that the connection port 3600 is positioned in use up to approximately 20 mm forward (e.g. anterior) of a central position at a top point of the head (e.g., a position lying in the coronal plane), and up to approximately 20 mm rearward (e.g. posterior) of the central position. In some forms of the technology the upper portion (e.g. the portion above the rear strap 3310) of the headgear tubes 3350 are configured to flex, bend and move in forward or rearward directions substantially without corresponding movement in the lower portion or non-adjustable tube section 3363 (e.g. the portion below the rear strap 3310). In other forms of the technology, the upper portion and lower portion may move together (although not necessarily to the same extent). The rear strap 3310 may be configured to prevent or resist movement of the non-adjustable tube section 3363. For example, by moving the upper portion of the headgear tubes 3350 forward on a patient's head without loosening the rear strap 3310, more movement of the upper portion of the headgear tubes 3350 may be required in comparison to the non-adjustable tube portion 3363.

Separately to the ability of the positioning and stabilising structure 3300 to be worn in different forward/rearward positions, in some forms of the technology the headgear tubing adjustment mechanism 3360 enables the positioning and stabilising structure 3300 to fit to different sized heads. The headgear tubing adjustment mechanism 3360 may be configured to provide a predetermined amount of length adjustment to the headgear tubing 3350. An amount of adjustment to the length of the headgear tubing 3350 may be determined based at least partly on a range of head sizes for which the positioning and stabilising structure 3300 is configured to accommodate. In some forms of the present technology the adjustment mechanism 3360 may be enable the headgear tubes 3350 to increase in length by an amount between approximately 10 mm and approximately 50 mm, inclusive, on either side of the positioning and stabilising structure 3300. In some forms of the present technology the increase in length may be an amount between approximately 20 mm and approximately 40 mm, inclusive, on either side. In some forms of the present technology the increase in length provided may be any one of approximately 25 mm, approximately 30 mm, approximately 35 mm, or approximately 40 mm on either side.

FIG. 3K shows a patient interface 3000 with positioning and stabilising structure 3300 having headgear tubes 3350 and a headgear tube adjustment mechanism in a first configuration identified with the reference numeral 3360. The adjustment mechanism 3360 is also shown in phantom in a second configuration and identified with the reference numeral 3360'. In the first configuration of the adjustment mechanism 3360 the headgear 3300 fits around a patient with one size head and in the second configuration of the adjustment mechanism 3360' the headgear 3300 fits around a patient with a larger head. In this form of the technology, the adjustment mechanism 3360' enables an extension of the length of the headgear tubes 3350 in order to fit around the larger head. As shown in FIG. 3K, the adjustment mechanism 3360/3360' enables the headgear to adjust (or be adjusted) to accommodate different head sizes while worn in a central position (e.g. with the connection port 3600/3600' positioned centrally at a top point on the head within the coronal plane, rather than forward or backwards of the coronal plane).

In some forms of the present technology the adjustment mechanism 3360 is also able to enable length adjustment of the headgear tubes 3350 when the headgear 3300 is worn in forward, central and/or rearward positions. FIG. 3L shows a patient interface 3000 with headgear 3300 worn in three positions on a patient's head, as identified by reference numerals suffixed with "a", "b" and "c". The positioning and stabilising structure 3300a is worn in a forward position, positioning and stabilising structure 3300b is worn in a central position and positioning and stabilising structure 3300c is worn in a rearward position. That is, the connection port 3600a is in a forward position on the patient's head, while the connection port 3600b is in a central position and connection port 3600c is in a rearward position. In the forward position, the headgear tubes 3350a fit around a smaller circumference of the patient's head in comparison to the circumference that the headgear tubes 3350b fit around in the central position. To accommodate this smaller circumference the adjustment mechanism 3360a in the forward position provides a reduction in the length of the headgear tubes 3350 (or less of an extension). In the rearward position the circumference of the patient's head around which the headgear tubes 3350c fit is larger than the circumference in the central position. To accommodate this larger circumference, the adjustment mechanism 3360c provides an increase in length of the headgear tubes 3350 in comparison to their length in the central position.

The combination of the different positions in which the positioning and stabilising structure 3300 can be worn, and the different amounts of length adjustment provided by the adjustment mechanism 3360, provides versatility in the adjustment options available to patients. This versatility may result in a wide range of head shapes and sizes being accommodated by the positioning and stabilising structure 3300 without excessive discomfort and while enabling a sufficient seal of the seal forming structure 3150 to the patient's face. In some embodiments, the adjustment mechanism 3360 provides for a lower magnitude of length adjustment, as patients with larger head sizes are able to wear the upper portion of the headgear tubing 3350 in a forward position, rather than relying solely on the adjustment mechanism 3360 to accommodate their large head size. In other embodiments the adjustment mechanism 3360 provides for a large magnitude of length adjustment, and the ability for patients with larger head sizes to wear the upper portion of the headgear tubing 3350 further forward means that the patient interface 3000 may be suitable for a large range of head sizes.

8.3.3.4 Position of Headgear Tubing Adjustment Mechanism

It is generally desirable to avoid features of patient interfaces that cause patient discomfort. Therefore, patient interfaces may be designed with few components contacting the patient's skin and those that do contact the patient's skin may be soft and/or smooth. The cheek region is known to be a source of patient discomfort when wearing patient interfaces.

Mechanisms allowing the positioning and stabilising structure to be adjusted, such as those described above, may comprise features that cause discomfort to a patient if contacting a patient's face or head, particularly the cheek region. Therefore, certain forms of the present technology comprise positioning and stabilising structures configured such that, when the patient interface is worn, the adjustment mechanism or parts thereof are positioned out of contact with areas of the patient's skin or hair, for example out of contact with the patient's face, like the patient's cheek regions. In some forms of the technology the adjustment mechanism is positioned higher than a patient's ears, i.e. superior to the otobasion superior of the patient's head or proximate a top portion of the patient's head. In these forms of the technology, the headgear tubes comprise a non-adjustable headgear tube section that is positioned adjacent to the patient's face in use, i.e. in a position where the non-adjustable headgear tube section might come into contact with the patient's face during use of the patient interface. For example, in some forms, the non-adjustable headgear tube section is positioned adjacent to the patient's cheek regions when worn and only non-adjustable headgear tube sections are adjacent to the patient's cheek regions, inferior to the otobasion superior of the patient's head or overlaying a maxilla region of the patient's head in some forms of the technology.

It will be understood that a non-adjustable headgear tube section is a section that is not specifically configured to be dimensionally adjusted during use, i.e. the adjustment mechanism does not form part of the non-adjustable headgear tube section. This does not preclude, however, the non-adjustable headgear tube section being able to be dimensionally adjusted if, for example, excessive force is imparted on it. The position of the non-adjustable headgear tube section may, however, be adjusted during use. In some forms of the present technology, non-adjustable headgear tube sections may be substantially non-adjustable in axial length, but may be adjustable in other ways such as by flexing, curving, straightening, and the like. For example, as shown in FIG. 3L, the non-adjustable headgear tube sections 3363a, 3363b, and 3363c are configured to bend or curve to different extents in order to facilitate the different positions in which the positioning and stabilising structure 3300 is worn on the head, with different amounts of extension provided by the adjustment mechanism 3360a, 3360b, and 3360c.

Locating the adjustment mechanism out of the patient's field of view may also be beneficial to avoid a feeling of claustrophobia or an interrupted view.

In the case of the form of patient interface 3000 shown in FIGS. 3A, 3B, 3C, 3D, 3E and 3F, for example, the concertina sections 3362 are positioned on either side of the patient's head between the ears or ear level and the crown or top of the head and non-adjustable headgear tube sections 3363, which form the lower ends of the headgear tubes (i.e. the inferior ends when worn by a patient) are positioned adjacent to (or over) the patient's cheek region when worn. Other examples of non-adjustable headgear tube sections 3363 are shown in FIGS. 5, 7A, 7B, 7C and 17.

In certain forms of the present technology the non-adjustable headgear tube sections 3363 are configured such that they assist in maintaining an adequate seal between the cushion assembly 3150 and the patient's face during use of the patient interface 3000. This may require the flexibility (or stiffness) of the non-adjustable headgear tube sections 3363 to be selected so that they are sufficiently stiff so as not to deform too easily during use while being sufficiently flexible to accommodate some movement during use and some variation in the position in which individual patients wear the patient interface 3000.

Rear headgear strap 3310 stabilises the headgear tubes 3350 on the patient's head but the lower ends of the headgear tubes 3350 are more freely able to move, particularly at points relatively far from the point at which rear headgear strap 3310 connects to the headgear tube 3350. An overly flexible lower end of a headgear tube 3350 tends to allow the cushion assembly 3150 to roll forward away from the patient's face, which disrupts the seal. This rolling forward effect can be mitigated by increasing the stiffness of the lower end of the headgear tubes 3350, i.e. the non-adjustable headgear tube section 3363 in the forms of the technology shown in FIGS. 3A, 3B, 3C, 3D, 3E, 3F, 5, 7A, 7B, 7C and 17. For the purposes of this discussion, the lower end of the headgear tubes 3350 may be considered to be the part of the headgear tubes 3350 positioned below (i.e. inferior to, when the patient interface 300 is worn by a patient) the point at which rear headgear strap 3310 connects to each headgear tube 3350 as this point is stabilised on the patient's head and therefore may tend to act as a pivot point to any movement of the headgear tubes 3350 below that point. It will be understood that other arrangements of headgear straps may lead to a different positioning of an effective pivot point.

For a similar reason it may be advantageous for the lower end of the headgear tubes 3350 to be free of any adjustment mechanisms in some forms of the technology. Locating a concertina section, for example, on the headgear tubes 3350 at a point below where the rear headgear strap 3310 connects to the headgear tubes 3350 means that the concertina section tends to buckle and distort if movement occurs and acts as a natural pivot, allowing movement of the cushion assembly, which could disrupt the seal with the patient's face.

Furthermore, an adjustment mechanism 3360 on the upper portion of headgear tube 3350 (which is considered, for the purposes of this discussion, to be the part of the headgear tubes 3350 positioned above, i.e. superior to, the point at which the rear headgear strap 3310 connects to each headgear tube 3350) helps to de-couple the upper and lower portions of the headgear tube 3350 so that movement of the upper portion (either during use or by virtue of variations in positioning of the patient interface 3000 on the patient's head) do not exert excessive forces on the cushion assembly 3150 that may tend to disrupt the seal with the patient's face. In particular, an adjustment mechanism 3360 in which the length of the headgear tube 3350 can be extended helps avoid straightening of non-adjustable headgear tube sections 3363 in the lower end of headgear tube 3350 as this kind of adjustment mechanism 3360 enables the lower end of the patient interface 3000 to move up and down relative to the patient's head (i.e. in the inferior and superior directions). Excessive straightening and/or stretching of the non-adjustable headgear tube sections 3363 may also cause the cushion assembly 3150 to roll forward, disrupting the seal to the patient's face.

In some forms of the technology, the radius of curvature of a non-adjustable headgear tube section 3363 (or lower end of the headgear tube 3350) also affects the degree of movement of the upper end of the headgear tubes 3350. The larger the radius of curvature the greater the de-coupling effect between the upper and lower ends of the headgear tubes 3350 so that the upper end of the headgear tubes 3350 can move without causing significant rolling forward to the cushion assembly 3150 and consequent loss of seal.

In some forms of the present technology, the provision of the adjustment mechanism 3360 on the upper portion of the headgear tube 3350, proximate the connection port 3600 may help to alleviate tube drag on the head as it allows the connection to decouple through stretch and flex provided by the adjustment mechanism.

In some forms of the present technology, providing the adjustment mechanisms 3360 on the upper portions of the headgear tubes 3350, spaced far from the cushion assembly 3150, may reduce effects on the cushion assembly 3150 caused by differences in the extension of the headgear tubes 3350. For example, effects of imbalances in the extension of, and/or any forces exerted by, the adjustment mechanism 3360 on either side of the patient's head may be less pronounced. Such effects may compromise the seal formed by the cushion assembly 3150 to the patient's face.

In other forms of the present technology the adjustment mechanism may be positioned close to the cushion assembly 3150 of the patient interface and be spaced from the patient's face by virtue of the size of the plenum chamber and the location of the port to which the tube 3350 connects to the plenum chamber distancing the lower end of the tube 3350 (and consequently the adjustment mechanism) from the patient's skin. The form of the present technology shown in FIG. 10B is one such example of a patient interface 3000 where the adjustment mechanism is spaced from the patient's face in use.

8.3.3.5 Headgear Tubing Bias Mechanism

In certain forms of the present technology, the positioning and stabilising structure 3300 comprises a bias mechanism which acts in use to urge the seal-forming structure 3100 towards the patient's face, i.e. towards the area surrounding the entrance to the patient's airways to which the seal-forming structure 3100 seals. The bias mechanism therefore acts to help the seal-forming structure 3100 provide a good seal with the patient's face during the use of the patient interface 3000 and to promote the retention of the seal when the patient interface supplies gas under positive pressure to the patient. In some forms of the technology, the bias mechanism acts (i.e. imparts a biasing force) on the adjustment mechanism 3360. When the plenum chamber 3200 is pressurised the tendency is for the cushion assembly 3150 of the patient interface 3000 to move away from the patient's face. A bias mechanism acting to bias or urge the cushion assembly 3150 towards the patient's face counters this tendency in order to maintain a seal.

In some forms of the technology, the bias mechanism acts to impart a biasing force along at least a part of a length of the headgear tube 3350 to urge the seal-forming structure towards the entrance of the patient's airways in use. In such forms the headgear tube 3350, or parts thereof, are in tension when in use. In some forms the bias mechanism is comprised as part of the headgear tubing 3350 while in other forms the bias mechanism is distinct from the headgear tubing 3350.

A bias mechanism may also assist in automatically adjusting the patient interface to fit a particular patient's head.

8.3.3.5.1 Magnitude of Force Exerted by Bias Mechanism

The bias mechanism is preferably configured to apply sufficient inwards (i.e. towards the patient's airway openings) force to maintain a good seal during use while avoiding applying an excessive force. An excessive force may cause the seal-forming structure 3100 to compress and its geometry change so that some parts of the structure move away from the patient's face and gas leaks out of the seal-forming structure. Furthermore, avoiding excessive forces on the patient's face from the patient interface promote comfort and avoid red marks, abrasion or sweating on the patient's face.

In some forms of the present technology, an acceptable force provided by the bias mechanism may be in the region of approximately 0.5N to approximately 4N on each side of the positioning and stabilising structure 3300. In some forms an acceptable force may be in the region of approximately 1N to approximately 3.5N. In some forms, forces of approximately 2N may be considered acceptable. In some forms of the present technology the positioning and stabilising structure 3300 is configured to support a seal-forming structure 3100 in the form of a full face or oro-nasal cushion assembly (e.g. such as the seal-forming structures 3100 shown in FIGS. 4A-4E). In some forms of the technology a full face or oro-nasal seal-forming structure 3100 is heavier than other forms of seal-forming structure (e.g. nasal cradle or nasal pillows) due to its larger size and the positioning and stabilising structure 3300 is configured to provide a larger biasing force accordingly to take up the weight or counteract the drag of the heavier seal-forming structure 3100 while still urging the cushion assembly 3150 into the patient's face with a sufficiently large force to maintain an effective seal, without causing excessive discomfort. Additionally, a full face or oro-nasal seal-forming structure 3100 may be subject to a downward (e.g. inferior) force when the patient relaxes or moves their lower jaw (which may be known as "jaw drop"). The positioning and stabilising structure 3100 may also be configured to account for the effects of jaw drop by counteracting the downwards forces received during jaw drop.

In some forms of the present technology, the positioning and stabilising structure 3300 is configured to interchangeably receive seal-forming structures of different sizes, including relatively small or light seal-forming structures such as a nasal cradle cushion assembly and relatively large or heavy seal-forming structures such as an oro-nasal cushion assembly. The positioning and stabilising structure may comprise a bias mechanism configured to support both types of seal-forming structure, by imparting a biasing force sufficiently strong for either type of seal-forming structure, but not excessive so as to cause discomfort.

In some forms of the technology, the positioning and stabilising structure 3300 is configured to provide a sufficient range of force magnitudes in a plurality of adjustment configurations to maintain an effective seal of either a nasal cradle or a full face mask, without being excessively large so as to cause discomfort.

In some forms of the present technology, the bias mechanism is configured to impart a force on the headgear tubes 3350 or portions thereof that urges the headgear tubing to fit around a patient's head. The bias mechanism may be configured to provide forces with magnitudes within a predetermined range. Such a predetermined range may be limited to magnitudes in which the headgear 3300 is both comfortable and able to maintain a sufficient seal of the seal-forming structure 3100 to the patient's face. The bias mechanism may be configured to urge the seal-forming structure 3100 into sealing contact with the patient's face with a force that is not less than a minimum force required for a sufficient seal. That is, the force may be equal to or greater than a minimum sealing force. The bias mechanism may be configured to urge the headgear tubing 3350 to fit to the patient's head with a force that is not larger than a maximum force considered comfortable by the patient. That is, the force may be less than or equal to a maximum comfort force.

In some forms of the present technology, each headgear tube 3350 comprises a force-extension characteristic which results from a relationship between the extension of the headgear tube 3350 and a force imparted to the headgear tube 3350 by the bias mechanism. Alternatively, or additionally, the force-extension characteristic may result from a relationship between the force imparted to the headgear tube 3350 by the bias mechanism and the extension of the headgear tube 3350. It will be understood that an "extension" refers to a change in overall length of the headgear tubes and does not imply any particular manner in which the change in overall length of the headgear tubes 3350 occurs or the physical structure of the adjustment mechanism.

In certain forms of the present technology, the bias mechanism may provide a biasing force on the headgear tube 3350 which tends to return the headgear tube 3350 or portions thereof to a predetermined length, such as a length prior to adjustment with the adjustment mechanism. In some forms of the technology the bias mechanism imparts a restoring force on the headgear tube 3350.

As described above, the adjustment mechanism 3360 of a patient interface 3000 according to some forms of the present technology allows an adjustment in length of a headgear tube 3350. In some embodiments, such as when there is a relationship between biasing force and the extension of a headgear tube 3350, a first amount of extension of the headgear tube 3350 (e.g. to a first extended length) results in a force provided by the bias mechanism which is equal to or greater than the minimum sealing force. Additionally, a second amount of extension of the headgear tube 3350 (e.g. to a second extended length) may result in a force provided by the bias mechanism which is less than or equal to the maximum comfort force. Furthermore, amounts of extension between the first and second amounts of extension may result in a force imparted by the biasing mechanism that is between the minimum sealing force and the maximum comfort force.

In some forms of the present technology the headgear tubes 3350 may comprise a force-extension characteristic in which, when the headgear tubes 3350 are adjusted to a first amount of extension (e.g. to the extension at which the bias mechanism provides at least the minimum sealing force), the positioning and stabilising structure 3300 accommodates a predetermined minimum head size. Similarly, when the headgear tubes 3350 are adjusted to a second amount of extension (e.g. to the extension at which no more than the maximum comfort force is exerted by the bias mechanism), the positioning and stabilising structure 3300 may accommodate a predetermined maximum head size. At extensions between the first and second amounts of extension the positioning and stabilising structure 3300 may accommodate head sizes between the minimum and maximum predetermined head sizes. The predetermined minimum head size may be, for example, a $5^{th}$ percentile head size and the predetermined maximum head size may be, for example, a $95^{th}$ percentile head size of the particular category of person. It will be understood that other measures/ranges may be used to determine minimum and maximum head sizes accommodated by the positioning and stabilising structure 3300.

FIG. 3I shows a force-extension plot 6000 illustrating a force-extension characteristic 6300 of a headgear tube 3350 of a patient interface 3000 according to one form of the present technology. The force-extension plot 6000 includes a horizontal extension axis 6100 and a vertical force axis 6200 to illustrate the relationship between the length of the headgear tube 3350 and the resulting force imparted by the bias mechanism.

Three extensions of the headgear tube 3350 are indicated on the extension axis 6100: zero extension 6105, a first amount of extension 6110 corresponding to an extension required to accommodate a $5^{th}$ percentile head size (e.g. a predetermined minimum head size), and a second amount of extension 6120 corresponding to an extension required to accommodate a $95^{th}$ percentile head size (e.g. a predetermined maximum head size). Two force magnitudes are indicated on the force axis 6200: a minimum sealing force 6210 and a maximum comfort force 6220.

In this exemplary form of the technology, the headgear tube 3350 comprises a force-extension characteristic 6300 in which the force imparted by the biasing means is greater than the minimum sealing force 6210 and less than the maximum comfort force 6220 throughout the range of extensions between the first amount of extension 6110 and the second amount of extension 6120. That is, across the full range of head sizes that are accommodated, a sufficient seal is able to be maintained without discomfort caused by an excessive biasing force.

It will be understood that in some forms of the technology the relationship between extension and biasing force may not be directly proportional. For example, in some forms of the technology there may be a relatively large increase in force during an initial stage of extension, but only minor or no variation in force in the range of extension required to accommodate minimum and maximum predetermined head sizes. The results of an effective seal without discomfort may be achieved if the magnitude of the force remains between the minimum seal force and the maximum comfort force throughout the range of extension between the minimum head size and maximum head size, regardless of the how force varies within the limits.

8.3.3.5.2 Position of Bias Mechanism

In some forms of the present technology, the bias mechanism acts between seal-forming structure 3100 and connection port 3600. For example, the bias mechanism is comprised of components of the patient interface connected between the seal-forming structure 3100 and connection port 3600 and may urge the seal-forming structure 3100 generally in the direction of the connection port 3600 and/or longitudinally along the length of tubes 3350.

8.3.3.5.3 Form of Bias Mechanism

The bias mechanism may take a number of forms. In some forms of the technology, the bias mechanism is a separate mechanism to the adjustment mechanism that enables adjustment of the positioning and stabilising structure such as those described above. In such forms the adjustment mechanism enables the patient interface to be adjusted to fit a patient's head while the bias mechanism acts to urge the seal against the patient's face. In other forms, the bias mechanism and adjustment mechanism are provided at least in part by the same features of the patient interface and the adjustment and bias described above are different functions performed by said same features.

In some forms of the technology the bias mechanism comprises an elastic or resilient member or assembly. In some forms the elastic or resilient member or assembly is connected between the seal-forming structure 3100 and the connection port 3600, for example it is comprised as part of, or is connected to, the tubes 3350 or the connection assembly between the tubes 3350 and the plenum chamber 3200 and/or the connection assembly between the tubes 3350 and the connection port 3600.

For example, in the form of the technology shown in FIGS. 3A, 3B, 3C, 3D and 3E, the bias mechanism comprises the concertina tube portions 3362. The concertina tube portions 3362 are configured such that they are biased to compressed positions. Consequently the concertina tube portions 3362 act to pull the seal-forming structure 3100 into the patient's face in use.

In some forms of the present technology, there is a relationship between the extension of the concertina tube portions 3362 and a restoring force imparted to the headgear tubes 3350. The restoring force may be tension in the concertina tube portions 3362. The concertina tube portions 3362 may have a force-extension characteristic with similarities to the force-extension characteristic discussed in relation to FIG. 3I.

The concertina tube portions 3362 may be designed to extend to a first amount of extension in which the positioning and stabilising structure 3300 can accommodate a predetermined minimum head size (such as a $5^{th}$ percentile head size) and also to a second amount of extension in which the positioning and stabilising structure 3300 can accommodate a predetermined maximum head size (such as a $95^{th}$ percentile head size). The concertina tube portions 3362 may be designed so that, at a first amount of extension, the tension is greater than a minimum force required to create a suitable seal of the seal-forming structure 3100 to the patient's face. At a second amount of extension, the concertina tube portions 3362 may be designed so that the tension does not exceed a maximum force considered comfortable by the patient. In this way, the positioning and stabilising structure 3300 can accommodate a range of head sizes, creating a sufficient seal across the full range without discomfort caused by excessive force.

In certain forms of the present technology, the concertina tube portions 3362 may comprise a concertina profile which provides the concertina tube portions 3362 with a force-extension characteristic such as discussed above. As shown in FIG. 3G, the concertina tube portions 3362 may comprise walls having a concertina profile having a repeating wave-like pattern with rounded inside troughs and flat outside peaks. The flattened outside peaks provide a smooth flat surface which may comfortably rest against the patient's head. The concertina tube portions 3362 may comprise a plurality of ribs formed in the walls of the headgear tubes 3350 to form the concertina. The ribs may be inwardly extending as shown in FIG. 3G. Alternatively, or additionally, the concertina tube portions 3362 may comprise a plurality of grooves.

The profile of the concertina tube portions 3362 may be varied to achieve a desired force-extension characteristic. For example, the pitch of the ribs (e.g. peaks/troughs of the concertina waveform) may be reduced to provide a more extendible concertina tube portion 3362 (e.g. generally more extension for a given amount of force). Furthermore, the height of the ribs (e.g. the amplitude of the concertina waveform) may be increased to provide a more extendible concertina tube portion 3362. Alternatively, a less extendible concertina tube portion 3362 may be produced by increasing the rib pitch, or by reducing the rib height.

Additionally, or alternatively, a longer concertina tube portion 3362 may be provided to increase extendibility. This may be provided by, for example, increasing the number of ribs formed in the wall of the concertina tube portion 3362.

Additionally, or alternatively, the wall thickness of the concertina tube portion 3362 may be reduced to provide a more extendible concertina tube portion 3362, or increased to provide a stiffer concertina tube portion 3362.

Additionally, or alternatively, the material forming the concertina tube portions 3362 may be selected to assist in providing a predetermined force-extension characteristic. In one form of the technology, the material is 50 durometer silicone. Other materials and/or durometer values may also be selected, such as 40 durometer silicone, for example.

Additionally, or alternatively, a different concertina profile shape may be provided to the concertina tube portion 3362, to achieve a different amount of extension. For example, a concertina tube portion 3362 in which the walls defining the profile are generally more folded together may result in a more extendible concertina tube portion 3362.

The configuration of the concertina tube portion 3362 may vary along its length. In some forms of the present technology, such as the form shown in FIG. 3G, the rib height decreases along the length of the concertina tube portion 3362 in the direction away from the connection port 3600 (e.g. the direction towards the non-adjustable headgear tube section 3363). The rib height may vary between, for example, a range of approximately 0 mm to approximately 6 mm, approximately 0 mm to approximately 5 mm, approximately 0 mm to approximately 4 mm, approximately 1 mm to approximately 5 mm and the like. Alternatively the rib height may be constant and may be, for example, approximately 2 mm, approximately 3 mm, approximately 4 mm and the like. The wall thickness may be substantially constant along the length of the concertina tube portion 3362, or may vary. In some forms of the technology the wall thickness may be between approximately 0.5 mm to approximately 1.2 mm. In some forms, the wall thickness may be between approximately 0.6 mm to approximately 1 mm. In some forms, the wall thickness may be approximately 0.8 mm, or any other like value. In some forms, the rib pitch may be between approximately 3.5 mm to approximately 5 mm. In some forms, the rib pitch may be between approximately 3.8 mm to approximately 4.5 mm. In some forms, the rib pitch may be approximately 4.2 mm, or any like value.

In other forms of the present technology, the shape and configuration of the concertina tube portion 3362 differs from those parameters mentioned above by way of example.

In the form of the technology shown in FIG. 13 the relatively stretchable section of tube 3355 is resiliently or elastically deformable and has a tendency to return to its non-stretched state. Therefore in use the relatively stretchable section of tube 3355 acts to pull the seal-forming structure 3100 into the patient's face. Alternatively tubes 3350 may be completely formed from a resilient material that tends to return to its non-stretched state when stretched.

Another form of the present technology is shown in FIG. 17. In this form, patient interface 3000 comprises one or more elastic sleeves 3340 that cover the tubes 3350. It will be understood that the elastic sleeves 3340 may partly cover the tubes 3350, for example there may be holes in the sleeves 3340 such as will be described below. Alternatively, the headgear tubes may be considered to comprise both the elastic sleeves and inner gas delivery conduits with the elastic sleeves covering the inner gas delivery conduits. Elastic sleeves 3340 may be formed from any elastic, resilient or stretchable material, for example an elastic fabric such as elastane, that has a tendency to return to its natural size and shape when stretched.

Elastic sleeves 3340 cover tubes 3350 that each comprise a concertina tube section 3362. The concertina tube section 3362 may or may not be biased to a compressed position. The concertina tube section 3362 allows the length of tubes 3350 to be adjusted so that the patient interface 3000 fits an individual patient while the elastic sleeves 3340 act to pull the seal-forming structure 3100 of cushion assembly 3150 into the patient's face to enhance the seal.

Elastic sleeves 3340 may comprise a single sheet of elastic material or may be formed from multiple sheets of elastic material connected together, for example sewn or glued together. Alternatively, patient interface 3000 may comprise a plurality of separate elastic sleeves, for example one sleeve may cover each of tubes 3350.

Elastic sleeves 3340 may comprise openings to allow parts of the patient interface to pass through the sleeves. For example, the elastic sleeves may comprise rear or side openings 3342 through which rear headgear straps 3310 connect to tubes 3350. Additionally or alternatively, the sleeves may comprise a top opening 3343 through which the air circuit 4170 connects to connection port 3600, or through which connection port 3600 may protrude. The headgear tubes 3350 may contact the patient's head through the openings 3342.

A concertina tube section 3362 of tube 3350 may be uncomfortable to a patient if it contacts their skin or hair during use. Patients may also find concertina sections unsightly or present the prospect of being uncomfortable to wear even if the concertina does not actually create extra discomfort, either of which may be undesirable. Covering the concertina section 3362 with an elastic sleeve 3340 avoids these problems. An inelastic sleeve may be used in some embodiments to provide the advantage of comfort. The sleeve may be advantageously formed of a soft material that is not uncomfortable if it contacts the patient.

As the elastic sleeve 3340 may be in contact with the patient's hair or skin during use it may easily become dirty from the patient's natural oils. Therefore the elastic sleeve 3340 may be advantageously formed from a material that is easily washed, e.g. fabric. To make it easy for the patient to wash the elastic sleeve 3340 it may be removable from the rest of the patient interface 3000. For example, the sleeve may comprise a mechanism for securing the sleeve on the tubes 3350 that can be disengaged for the sleeve to be removed. For example the elastic sleeve 3340 may wrap around the tubes 3350 and connect to itself by clips, poppers, hook-and-loop material or other suitable fasteners.

In some forms of the technology the elastic sleeve 3340 is formed from a material or textile that helps wick moisture away from the patient's face. This may help to maintain comfort if the patient sweats while wearing the patient interface.

In other forms of the technology, elastic sleeves may cover tubes or other parts of the positioning and stabilising mechanism having other adjustment mechanisms such as those described above. Sleeves may be beneficial in covering mechanisms or components that appear complicated or medical which may deter the patient from wearing the patient interface.

In other forms of the technology, telescopically adjustable headgear tubes may comprise a bias mechanism acting to contract the telescopically movable headgear tube sections, for example a spring.

An advantage of manually adjustable adjustment mechanisms which may also provide a biasing force, such as the adjustment mechanism 3360 shown in FIG. 7C, is the ability to support both relatively heavy and relatively light seal-forming structures in a modular design, i.e. where different types of seal-forming structures can be interchanged. For example, if the cushion assembly 3150 of the embodiment shown in FIG. 7C is replaced with a heavier oro-nasal cushion assembly the patient is able to manually adjust the length of the headgear tubes 3350 to a shorter configuration to counteract the weight of the oro-nasal cushion and prevent the cushion from sagging downwards or being pushed downwards by movement of the patient's lower jaw.

8.3.4 Vent

In one form, the patient interface 3000 includes a vent constructed and arranged to allow for the continuous flow or washout of exhaled gases, e.g. carbon dioxide ($CO_2$) from an interior of the plenum chamber to ambient to reduce the risk of the patient rebreathing such gases. That is, the vent allows the flow of patient exhaled $CO_2$ to an exterior of the patient interface. The vent is sized and shaped to maintain the therapeutic pressure in the plenum chamber.

One form of vent in accordance with the present technology comprises a plurality of holes, for example, about 20 to about 80 holes, or about 40 to about 60 holes, or about 45 to about 55 holes.

The vent may be located in the plenum chamber 3200. Alternatively, the vent may be located in another part of the patient interface, e.g., a tube 3350 fluidly connecting connection port 3600 with the plenum chamber 3200.

8.3.5 Decoupling Structure(s)

In one form the patient interface 3000 includes at least one decoupling structure, for example, a swivel or a ball and socket. The decoupling structure may be arranged at or proximate the connection port 3600 to permit the conduit of the air circuit 4170 to move relative to patient interface 3000 and reduce the risk of destabilising the seal of the seal-forming structure 3100 against the patient's face.

8.3.6 Connection Port

Connection port 3600 allows for connection to the air circuit 4170. In the embodiments of the technology shown in FIGS. 3 and 5-17, for example, the connection port is positioned on top of the patient's head when the patient interface 3000 is being worn. In other embodiments, the connection port is configured to be positioned, in use, proximal a top, side or rear portion of the patient's head. Patient interfaces in which the connection port is not positioned in front of the patient's face may be advantageous as some patient's find a conduit that connects to a patient interface in front of the face to be unsightly and obtrusive. For example, a conduit connecting to a patient interface front of the face may be prone to being tangled up in bedclothes, particularly, if the conduit extends downwardly from the patient interface in use.

8.3.7 Forehead Support

In one form, the patient interface 3000 includes a forehead support for contacting the patient's forehead region to support the patient interface on the patient's head during use and helping to maintain the sealing structure in sealed contact with the patient's face.

8.3.8 Anti-Asphyxia Valve

In some forms of the technology the patient interface 3000 is constructed and arranged to allow a patient to breathe ambient air in the event of a power failure. In one form, the patient interface 3000 includes an anti-asphyxia valve.

8.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

8.4 RPT Device

Figure 4A:
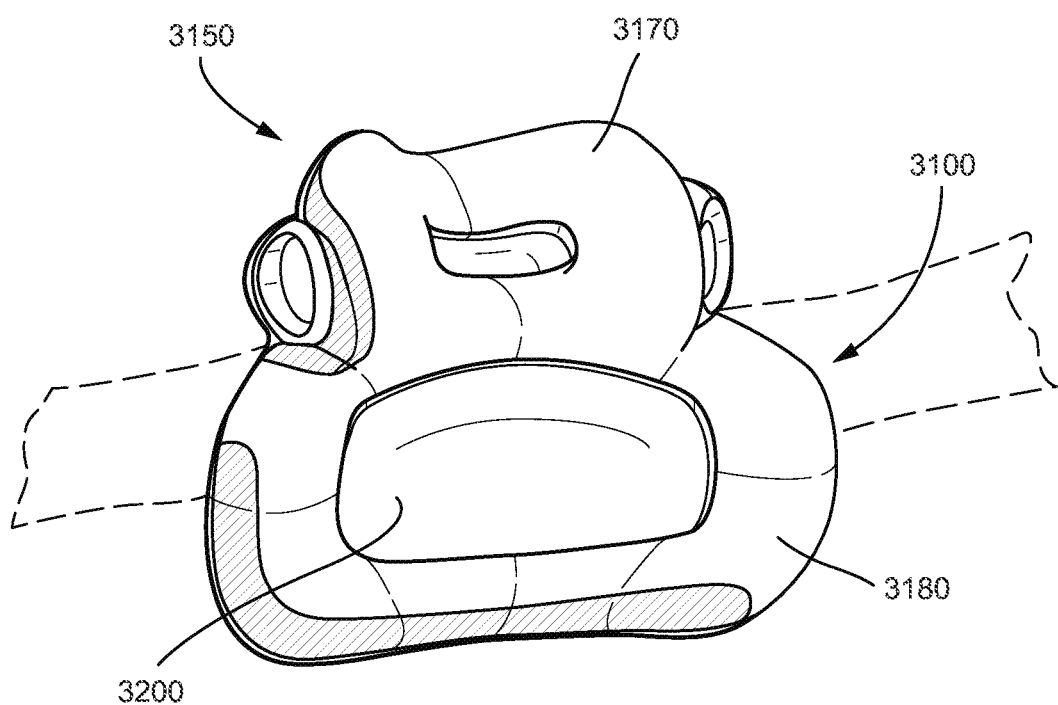
Figure 4B:
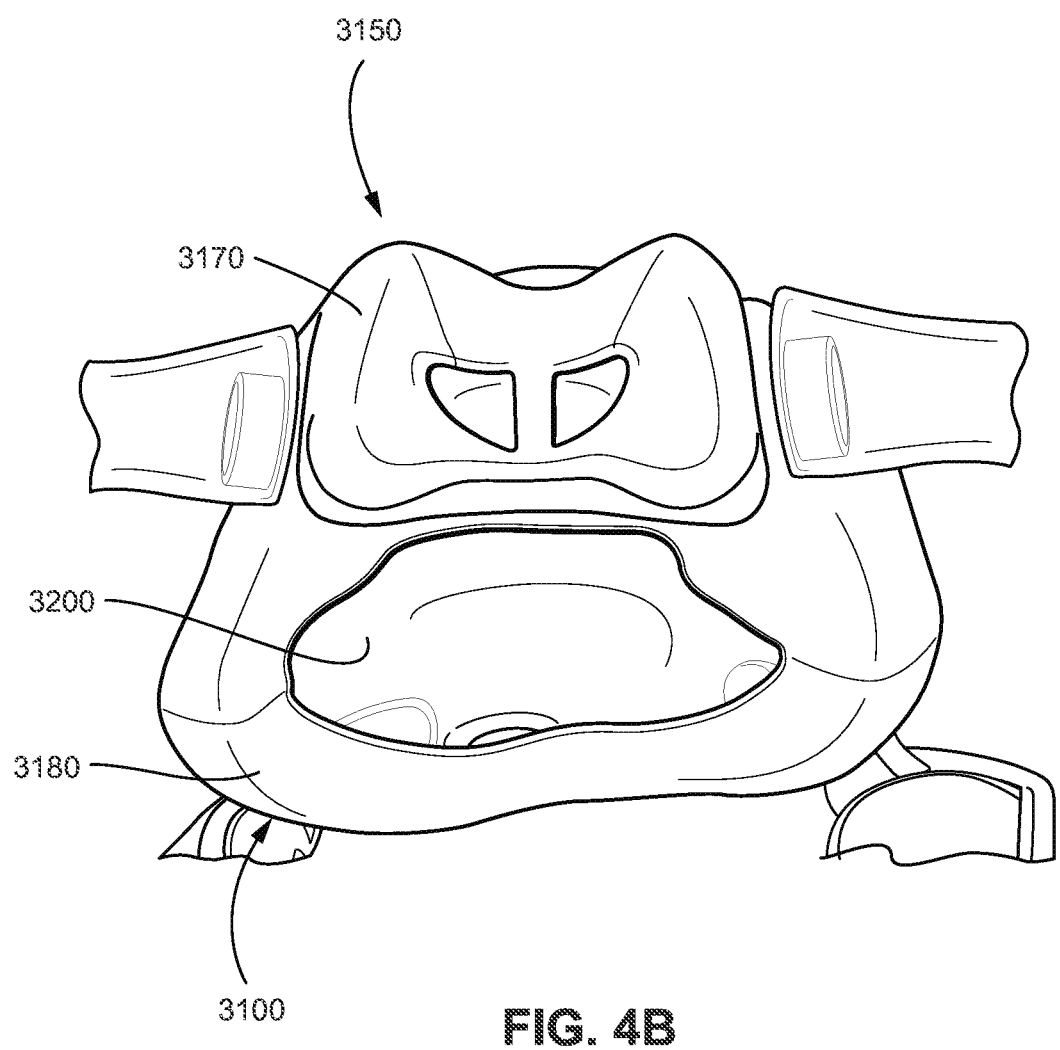
Figure 4C:
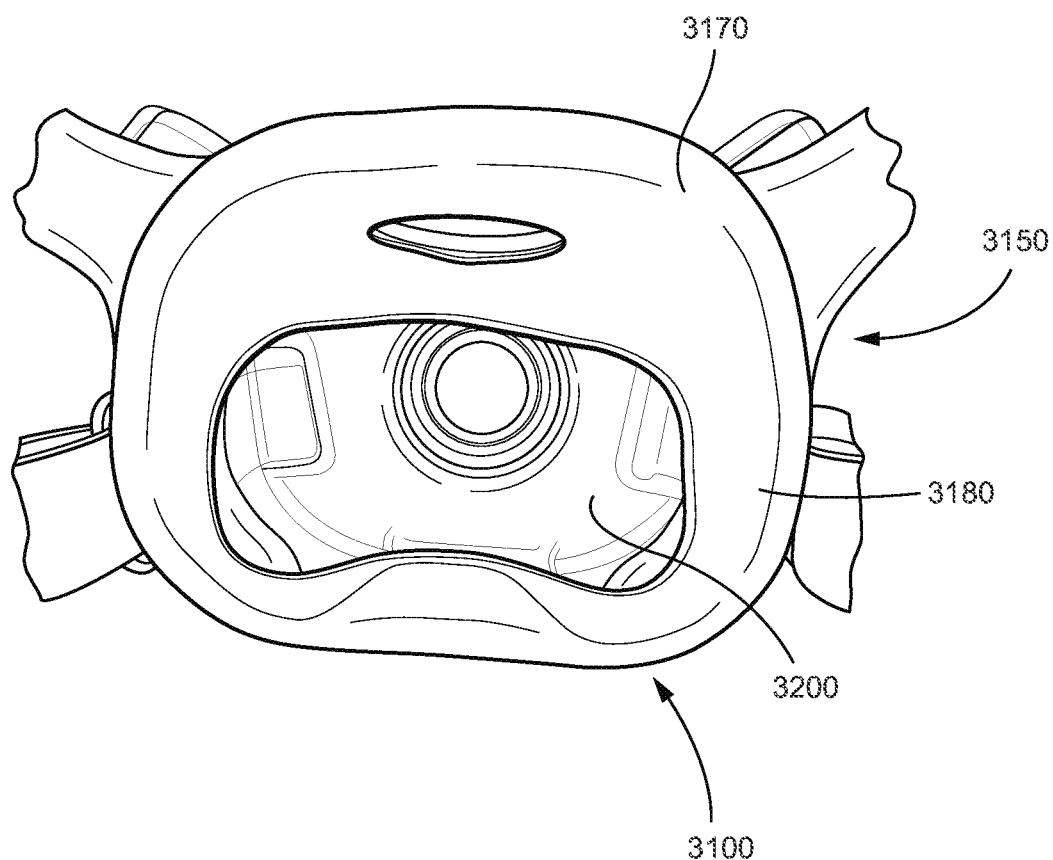
Figure 4D:
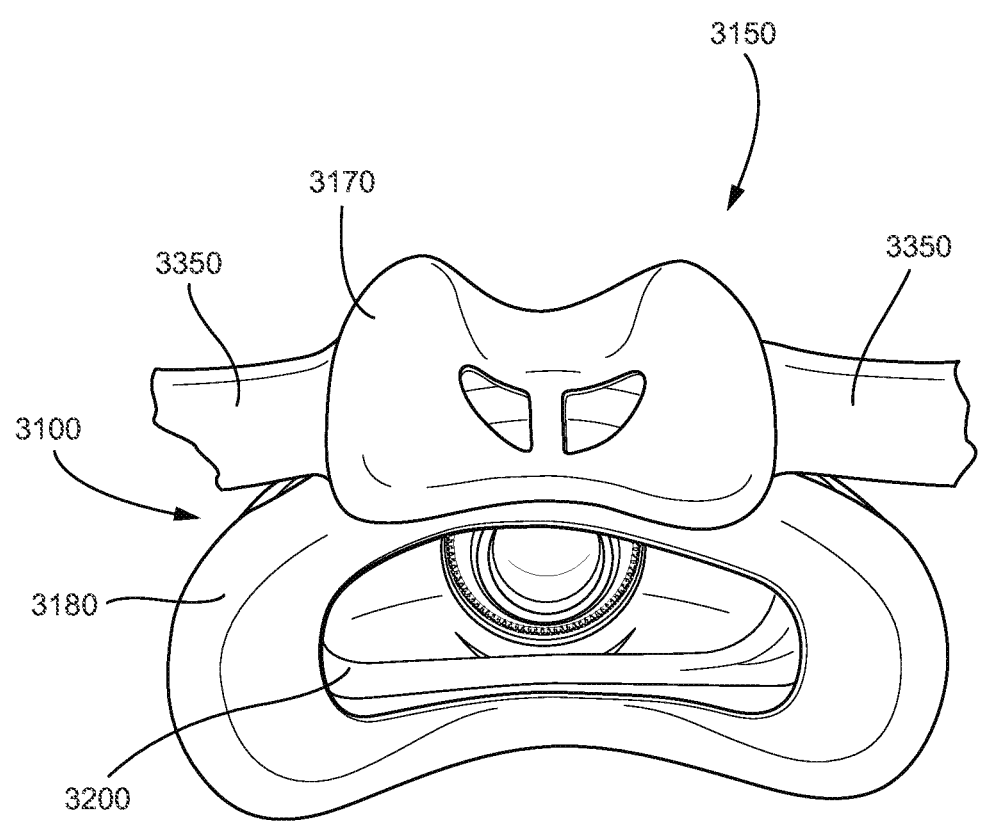
Figure 4E:
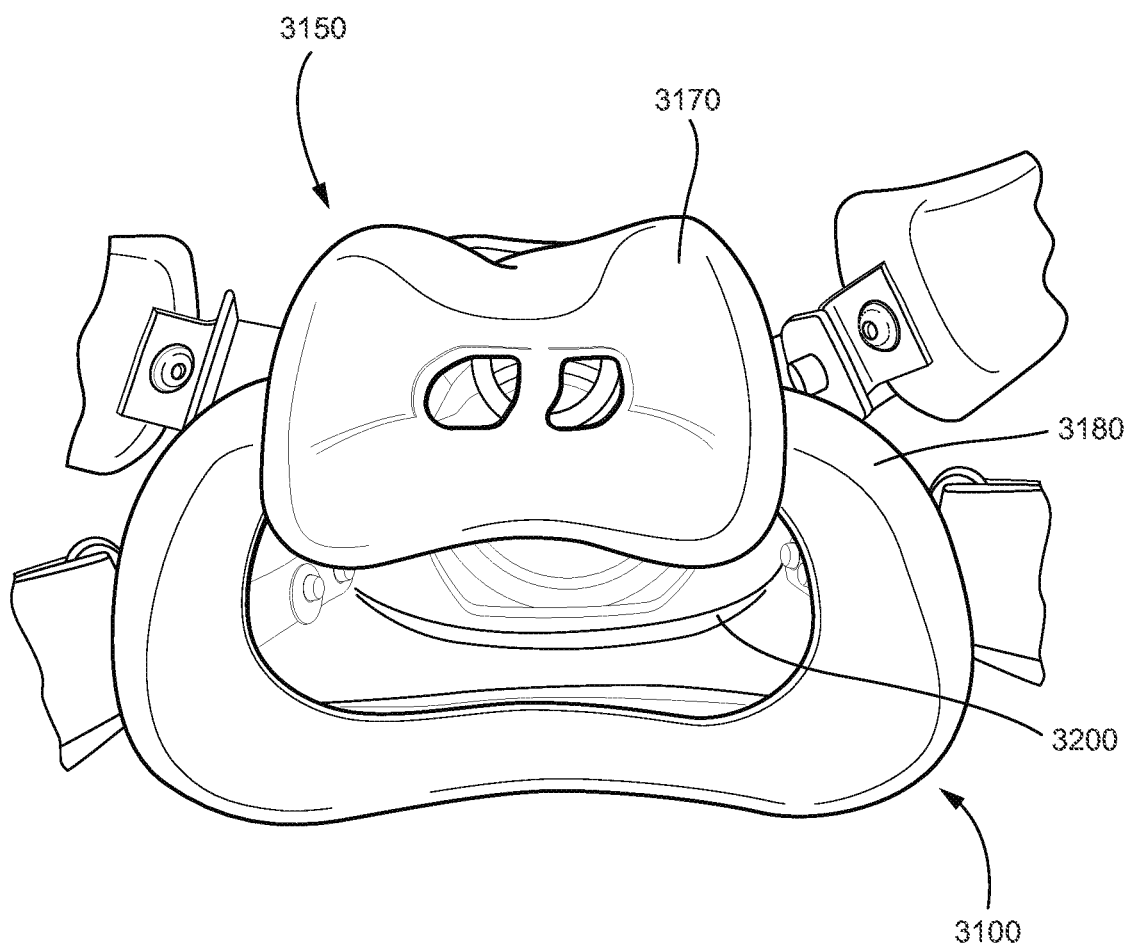

An RPT device 4000 in accordance with one aspect of the present technology (as shown in FIG. 4A) comprises mechanical and pneumatic components 4100, electrical components 4200 and is configured to execute one or more algorithms 4300. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

8.4.1 RPT Device Mechanical & Pneumatic Components

An RPT device may comprise one or more of the following components in an integral unit. In an alternative form, one or more of the following components may be located as respective separate units.

8.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

8.4.1.2 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,14; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

8.4.1.3 Air Circuit

An air circuit 4170 in accordance with an aspect of the present technology is a conduit or a tube constructed and arranged to allow, in use, a flow of air to travel between two components such as the RPT device 4000 and the patient interface 3000.

In particular, the air circuit 4170 may be in fluid connection with the outlet of the RPT device 4000 and the patient interface 3000. The air circuit may be referred to as an air delivery tube or conduit. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

8.5 Humidifier

8.5.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

8.6 Glossary

For the purposes of the present technology disclosure, in certain forms of the present technology, one or more of the following definitions may apply. In other forms of the present technology, alternative definitions may apply.

8.6.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory disease.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

8.6.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

8.6.1.2 Mechanical Properties

Resilience: Ability of a material to absorb energy when deformed elastically and to release the energy upon unloading.

'Resilient': Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

'Floppy' structure or component: A structure or component that will change shape, e.g. bend, when caused to support its own weight, within a relatively short period of time such as 1 second.

'Rigid' structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

8.6.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
  (i) a 30% reduction in patient breathing for at least 10 seconds plus an associated 4% desaturation; or
  (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

8.6.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

8.6.4 Anatomy

8.6.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius): A point on the face between the mouth and supramenton, lying in the median sagittal plane.

Lip, upper (labrale superius): A point on the face between the mouth and nose, lying in the median sagittal plane.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion

8.6.4.2 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

8.6.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

8.6.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilising structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

8.7 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Furthermore, "approximately", "substantially", "about", or any similar term as used herein means +/−5 to +/−10% of the recited value.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

8.8 Reference Signs List

1000 Patient
1100 Bed partner
3000 Patient interface
3000a Patient interface
3000b Patient interface
3000c Patient interface
3100 Sealing or seal-forming structure
3150 Cushion assembly
3170 Nasal seal-forming structure
3180 Oral seal-forming structure
3200 Plenum chamber
3210 Plenum chamber perimeter
3300 Positing and stabilising structure/headgear
3300a Positing and stabilising structure/headgear
3300b Positing and stabilising structure/headgear
3300c Positing and stabilising structure/headgear
3310 Headgear strap
3320 Chin strap
3330 Padded members
3340 Elastic sleeves
3342 Side opening
3343 Top opening
3345 Tab
3347 Rounded edges
3348 Patient contacting side
3349 Non-patient contacting side
3350 Headgear tube
3350a Headgear tubing
3350b Headgear tubing
3350c Headgear tubing
3351 Upper tube member
3352 Tube ends
3353A Upper curved portion
3353B Lower curved portion
3354 Less stretchable tube section
3355 More stretchable tube section
3356 Securing mechanism
3357 First securing member
3358 Second securing member
3360 Adjustment mechanism
3360' Adjustment mechanism
3360a Adjustment mechanism
3360b Adjustment mechanism
3360c Adjustment mechanism
3362 Concertina tube section
3362a Concertina tube section
3362b Concertina tube section
3362c Concertina tube section
3363 Non-adjustable headgear tube section
3363a Non-adjustable headgear tube section
3364 Fold portion
3366 Tube wall fold/rolling fold portion
3368 Adjacent tube portion
3370 First tube portion
3371 First tab
3372 Second tube portion
3373 Second tab
3374 Ribs
3375 Nested concentric tube sections
3375a Nested concentric tube sections
3375b Nested concentric tube sections
3376 Ratchet mechanism
3377 Visual indicator
3377a Small
3377b Medium
3377c Large
3378 Button
3379 Rigidizing members
3380 First threaded portion
3382 Second threaded portion
3383 Pinion
3384 Ring member
3385 Replaceable tube portion
3386 Replacement tube portions
3387 Tube insert member
3390 Strap
3391 Strap adjustment mechanism
3395 Band
3397 Tongue
3398 Grooves
3410 Loop insert member
3411 Replacement loop insert members
3420 Inflatable loop insert member
3600 Connection port
3744 ISO
4000 RPT device
4010 External housing
4012 Upper portion
4014 Portion
4015 Panel
4016 Chassis
4018 Handle
4020 Pneumatic block 4100 Pneumatic components
4110 Air filter
4112 Inlet air filter
4114 Outlet air filter
4122 Inlet muffler
4124 Outlet muffler
4140 Pressure generator
4142 Controllable blower
4144 Brushless DC motor
4170 Air circuit
4200 Electrical components
4202 Printed Circuit Board Assembly (PCBA)
4210 Electrical power supply
4220 Input devices
4230 Central controller
4240 Therapy device controller
4250 Protection circuits
4260 Memory
4270 Transducers
4272 Pressure sensors
4274 Flow rate sensors
4280 Data communication interface
4290 Output devices
4300 Algorithms
5000 Humidifier
5002 Humidifier inlet
5004 Humidifier outlet
5006 Humidifier base
5110 Humidifier reservoir
5130 Humidifier reservoir dock
5240 Heating element
6000 Force-extension plot
6100 Extension axis
6105 Zero extension
6110 First amount of extension
6120 Second amount of extension
6200 Force axis
6210 Minimum sealing force
6220 Maximum comfort force
6300 Force-extension characteristic
7292 Section
7310 Rear strap
7320 Chin strap
7345 Tab
7387 Insert member
7390 Front hoop
7391 Adjustment mechanism
7392 First section
7393 Second section
7394 Link member
7396 Region
7399 Drawstring
7400 Locking mechanism
7401 Release button
7402 Control unit
7404 Mobile phone software application
7406 Cable
7407 Tube connector
7408 Swivel joint
7410 Upper end
7411 Lower end
7412 Single axis
7413 Axis
7600 Connection port
7604 De-coupling mechanism
7608 Superior tube portion
8345 Coupling
8387 Insert member
8400 Locking mechanism
8407 Tube connector
8408 Swivel joint
8410 Upper end
8412 Axis
8413 Axis
8414 Axis
8415 First swivel
8416 Second swivel
8600 Connection port
8602 Central portion
8604 Protrusion
8606 Lower side
8608 Eyelet tab
9350 Tube
9354 Non-stretchable section
9355 Stretchable section
9357 First fastening member
9358 Second fastening member
9408 Swivel joint
9411 Upper ends
9412 Axis
9413 Axis
9414 Axis
9415 First swivel
9416 Second swivel
9600 Connection port
9602 Central portion
10420 Inflatable portion
10500 Start treatment session
10505 Retrieve stored value
10510 Sense pressure in inflatable portion
10515 Compared sensed pressure to stored value
10520 Adjust pressure in inflatable portion
10525 Sense patient apnea
10530 Adjust pressure in inflatable portion
10535 Set new value

The invention claimed is:

1. A positioning and stabilising structure to hold a seal-forming structure in a therapeutically effective position on a head of a patient, the seal-forming structure being constructed and arranged to form a seal with a region of the patient's face surrounding an entrance to the patient's airways for sealed delivery of a flow of air at a therapeutic pressure of at least 4 cmH2O with respect to ambient air pressure throughout the patient's respiratory cycle in use, the positioning and stabilising structure comprising:
a front hoop extending, in use, across the patient's cheek regions and arranged to contact, in use, regions of the patient's head superior to an otobasion superior of the patient's head, the front hoop comprising:
lower portions of two gas delivery tubes fluidly connected to the seal-forming structure, each lower portion of the gas delivery tube extending, in use, across one of the patient's cheek regions, the two gas delivery tubes being on different sides of the patient's head, and
a link connecting the two gas delivery tubes between the lower portions and upper portions of the two gas delivery tubes; and
a rear strap configured, in use, to pass around the back of the patient's head;
a de-coupling mechanism configured to decouple positional adjustment of the upper portions of the gas delivery tubes from movement of the seal-forming structure away from the patient's face in use to enable positional adjustment of the upper portions of the gas delivery tubes on the patient's head; and an adjustment mechanism configured to adjust the front hoop and the rear strap relative to the patient's head, the adjustment mechanism being arranged in a single operation to adjust both the front hoop and the rear strap to enable the positioning and stabilising structure to fit different size heads.

2. The positioning and stabilising structure as claimed in claim 1, wherein the de-coupling mechanism comprises:

the upper portions being bendable and including corrugations and/or concertinas on the upper portions to enable positional adjustment of the upper portions of the two gas delivery tubes on the patient's head in use; and at least one swivel including a connection port configured to connect to an air circuit, the at least one swivel configured to allow relative rotation between the upper portions and the air circuit.

3. The positioning and stabilising structure as claimed in claim 2, wherein the upper portions are positioned superior to an otobasion superior of the patient's head, in use.

4. The positioning and stabilising structure as claimed in claim 3, wherein the at least one swivel rotates about a swivel axis, the swivel axis oriented substantially parallel to an axis along the upper portions.

5. The positioning and stabilising structure as claimed in claim 2, wherein the at least one swivel includes a first swivel and a second swivel configured to rotate relative to the first swivel.

6. The positioning and stabilising structure as claimed in claim 5, wherein the first swivel rotates about a first axis, and the second swivel rotates about a second axis perpendicular to the first axis.

7. The positioning and stabilising structure as claimed in claim 5, wherein the first swivel is rotatable independently of the second swivel.

8. The positioning and stabilising structure as claimed in claim 5, wherein the decoupling mechanism further comprises a tube connector coupled to the two gas delivery tubes, which diverge from the tube connector.

9. The positioning and stabilising structure as claimed in claim 8, wherein the first swivel is connected directly to the tube connector.

10. The positioning and stabilising structure as claimed in claim 8, wherein the tube connector is non-rotatable relative to the two gas delivery tubes, and wherein the first swivel is rotatable relative to the tube connector.

11. The positioning and stabilising structure as claimed in claim 1, wherein the de-coupling mechanism is Y-shaped or V-shaped.

12. The positioning and stabilising structure as claimed in claim 1, wherein the adjustment mechanism is operable to adjust a length of a link member between the lower portions, wherein adjustment of the length adjusts both the front hoop and the rear straps simultaneously.

13. A positioning and stabilising structure to hold a seal-forming structure in a therapeutically effective position on a patient's head, the seal-forming structure being constructed and arranged to form a seal with a region of the patient's face surrounding an entrance to the patient's airways for sealed delivery of a flow of air at a therapeutic pressure of at least 4 cmH$_2$O with respect to ambient air pressure throughout the patient's respiratory cycle in use, the positioning and stabilising structure comprising:

at least one hoop extending, in use, across the patient's cheek regions and arranged to contact, in use, regions of the patient's head superior to an otobasion superior of the patient's head, wherein the at least one hoop comprises:

at least one gas delivery tube to deliver the flow of air to the entrance of a patient's airways via the seal-forming structure, the at least one gas delivery tube being constructed and arranged to overlie, in use, at least a region of the patient's head superior to an otobasion superior of the patient's head; and an adjustment mechanism configured to adjust the at least one hoop to enable the positioning and stabilising structure to fit different size heads, the adjustment mechanism comprises one or more inflatable portions; and a controller and at least one sensor in communication with the controller, the at least one sensor being configured to generate a signal based on whether the patient is experiencing sleep apnea, the controller configured to regulate a volume of air within the one or more inflatable portions based on the signal from the one or more sensors indicating the patient is experiencing apnea.

14. The positioning and stabilising structure according to claim 13, wherein at least one inflatable portion of the one or more inflatable portions forms a patient contacting portion of the hoop and is configured to adjust the position of the at least one gas delivery tube on the patient's head.

15. The positioning and stabilising structure according to claim 13, wherein the one or more inflatable portions adjusts an effective length of the hoop.

16. The positioning and stabilising structure according to claim 15, wherein the at least one inflatable portion is movable between a deflated state and an inflated state, and wherein the deflated state forms a larger effective length than the inflated state.

17. The positioning and stabilising structure according to claim 13, further comprising a retainer disposed in a side of the at least one gas delivery tube for retaining the one or more inflatable portions relative to the at least one gas delivery tube.

18. The positioning and stabilising structure according to claim 17, wherein the retainer is in the form of one or more fasteners fixed to the at least one gas delivery tube.

19. The positioning and stabilising structure according to claim 18, wherein the retainer is in the form of a loop that surrounds the at least one gas delivery tube.

20. The positioning and stabilising structure according to claim 17, wherein the retainer is disposed on an inferior side of the at least one gas delivery tube and a complimentary retainer is disposed on a superior surface of the one or more inflatable portions.

21. The positioning and stabilising structure according to claim 13, wherein the one or more inflatable portions are fixed to the at least one gas delivery tube.

22. The positioning and stabilising structure according to claim 14, wherein the one or more sensors comprises a pressure sensor, a light sensor, and/or a position sensor, and the one or more sensors is configured to determine an inflation state of the one or more inflatable portions.

23. The positioning and stabilising structure according to claim 14, further comprising a valve configured to selectively provide airflow into the one or more inflatable portions.

24. The positioning and stabilising structure according to claim 23, wherein the controller is configured to control a position of the valve.

25. The positioning and stabilising structure according to claim 23, wherein a position of the valve is manually controllable.

* * * * *